(12) United States Patent
Man et al.

(10) Patent No.: US 11,044,907 B2
(45) Date of Patent: *Jun. 29, 2021

(54) INTERACTION BETWEEN ANTIMICROBIAL QUATERNARY COMPOUNDS AND ANIONIC SURFACTANTS

(71) Applicant: Ecolab USA Inc., Saint Paul, MN (US)

(72) Inventors: Victor Fuk-Pong Man, Saint Paul, MN (US); Derrick Richard Anderson, Saint Paul, MN (US)

(73) Assignee: Ecolab USA Inc., Saint Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/546,567

(22) Filed: Aug. 21, 2019

(65) Prior Publication Data

US 2019/0380335 A1 Dec. 19, 2019

Related U.S. Application Data

(63) Continuation of application No. 15/444,987, filed on Feb. 28, 2017, now Pat. No. 10,426,162.

(60) Provisional application No. 62/373,772, filed on Aug. 11, 2016.

(51) Int. Cl.
*A01N 33/12* (2006.01)
*A01N 25/30* (2006.01)

(52) U.S. Cl.
CPC ............ *A01N 33/12* (2013.01); *A01N 25/30* (2013.01)

(58) Field of Classification Search
CPC .......... A01N 33/12; A01N 25/30; A61P 17/00
See application file for complete search history.

(56) References Cited

U.S. PATENT DOCUMENTS

| | | | |
|---|---|---|---|
| 3,920,563 A | 11/1975 | Wixon | |
| 4,647,314 A | 3/1987 | Mullins et al. | |
| 4,847,088 A | 7/1989 | Blank | |
| 5,411,585 A | 5/1995 | Avery et al. | |
| 5,454,984 A | 10/1995 | Graubart et al. | |
| 5,573,710 A | 11/1996 | McDonell | |
| 5,747,108 A | 5/1998 | Farooq et al. | |
| 5,998,358 A | 12/1999 | Herdt et al. | |
| 6,010,996 A * | 1/2000 | Hu | A01N 33/12 510/384 |
| 6,017,561 A * | 1/2000 | Zhou | A01N 33/12 424/486 |
| 6,121,219 A | 9/2000 | Herdt et al. | |
| 6,136,769 A | 10/2000 | Asano et al. | |
| 6,150,320 A | 11/2000 | McDonell et al. | |
| 6,239,092 B1 | 5/2001 | Papasso et al. | |
| 6,303,557 B1 | 10/2001 | Colclough | |
| 6,310,013 B1 | 10/2001 | Lokkesmoe et al. | |
| 6,339,054 B1 * | 1/2002 | Levitt | C09G 1/02 510/241 |
| 6,350,725 B1 | 2/2002 | Levitt et al. | |
| 6,387,870 B1 | 5/2002 | Klaers et al. | |
| 6,475,961 B2 | 11/2002 | Lokkesmoe et al. | |
| 6,482,791 B2 | 11/2002 | Sane et al. | |
| 6,525,005 B1 | 2/2003 | Kravitz et al. | |
| 6,525,014 B1 | 2/2003 | Gorlin et al. | |
| 6,602,350 B2 | 8/2003 | Levitt et al. | |
| 6,627,657 B1 | 9/2003 | Hilgren et al. | |
| 6,632,291 B2 | 10/2003 | Rabon et al. | |
| 6,720,301 B2 | 4/2004 | Gorlin et al. | |
| 6,730,648 B2 | 5/2004 | Gorlin et al. | |
| 6,855,328 B2 | 2/2005 | Hei et al. | |
| 6,864,220 B2 | 3/2005 | Levitt et al. | |
| 6,878,681 B1 | 4/2005 | Gohl et al. | |

(Continued)

FOREIGN PATENT DOCUMENTS

| | | |
|---|---|---|
| CN | 1183268 A | 6/1998 |
| CN | 12762857 A | 4/2006 |

(Continued)

OTHER PUBLICATIONS

Boethling, Robert S., "Environmental Fate and Toxicity in Wastewater Treatment of Quaternary Ammonium Surfactants", Water Res. vol. 18, No. 9, pp. 1061-1076, Feb. 1984.

Burdock, George A., correspondence regarding "Benzalkonium Chloride as a Component of Free N. Clear™ GRAS Notification", 58 pages, dated Sep. 6, 2013.

Rajkowska et al., "Quartemary Ammonium Biocides as Antimicrobial Agents Protecting Historical Wood and Brick," Acta Biochimica Polonica, vol. 63, No. 1/2016, pp. 153-159, Dec. 3, 2015.

Tubajika, Kayimbi M., "Effectiveness of alkyl dimethyl benzyl ammonium chloride in reducing the population of Xanthomonas campestris pv. vesicatoria and Pseudomonas syringae pv. syringae in tomatoes, beans and peppers", Archives of Phytopathology and Plant Protection, 5 pages, pp. 688-697, Jun. 5, 2009.

(Continued)

*Primary Examiner* — Sudhakar Katakam
(74) *Attorney, Agent, or Firm* — McKee, Voorhees & Sease, PLC

(57) ABSTRACT

The invention provides activated or inactivated compositions combining quaternary ammonium compounds and anionic surfactants or acids. The invention further provides activated or inactivated compositions combining quaternary ammonium compounds and anionic chelants or polymers. Activated antimicrobial compositions comprised of a quaternary ammonium compound having less than a C20 chain length, and an anionic carboxylate surfactant having C6-C10 chain length are disclosed. Activated compositions of the invention have a pH of between about 1 and 7 and are substantially free of silanes, sulfates and oxidants. Inactivated antimicrobial compositions comprised of a quaternary ammonium compound having less than a C-20 chain length, and an anionic sulfate or sulfonate surfactant are disclosed. Compositions of the invention have a 10 mole to 1 moles ratio of quaternary ammonium compound to anionic surfactant or about 1 mole to 10 moles ratio. Methods of making and employing the compositions are disclosed.

13 Claims, 29 Drawing Sheets

(56) References Cited

U.S. PATENT DOCUMENTS

| | | |
|---|---|---|
| 6,924,260 B2 | 8/2005 | Aubay |
| 7,482,315 B2 | 1/2009 | Levitt et al. |
| 7,601,681 B2 | 10/2009 | Smets et al. |
| 7,820,594 B2 | 10/2010 | Coleman |
| 7,951,245 B2 | 5/2011 | Levitt et al. |
| 8,003,369 B2 | 8/2011 | Yamaguchi et al. |
| 8,110,537 B2 | 2/2012 | Gohl et al. |
| 8,246,906 B2 | 8/2012 | Hei et al. |
| 8,337,872 B2 | 12/2012 | Fuls et al. |
| 9,034,813 B2 | 5/2015 | Man et al. |
| 9,309,485 B2 | 4/2016 | Hunt, Jr. et al. |
| 9,410,110 B2 | 8/2016 | Man et al. |
| 2003/0228992 A1 | 12/2003 | Smets et al. |
| 2004/0071653 A1 | 4/2004 | Bratescu et al. |
| 2005/0014672 A1 | 1/2005 | Arif |
| 2006/0014655 A1 | 1/2006 | Smets et al. |
| 2006/0128585 A1 | 6/2006 | Adair et al. |
| 2007/0281002 A1 | 12/2007 | Morales et al. |
| 2008/0119527 A1 | 5/2008 | Baldo |
| 2008/0145390 A1 | 6/2008 | Taylor et al. |
| 2009/0149359 A1 | 6/2009 | Hundley et al. |
| 2010/0227930 A1 | 9/2010 | Lusignan |
| 2010/0256025 A1 | 10/2010 | Van Zanten et al. |
| 2011/0195131 A1 | 8/2011 | Bouchard et al. |
| 2011/0262892 A1 | 10/2011 | Aoyagi et al. |
| 2012/0070341 A1 | 3/2012 | Eder et al. |
| 2012/0252716 A1 | 10/2012 | Barnabas et al. |
| 2013/0137618 A1 | 5/2013 | Wood |
| 2013/0210923 A1 | 8/2013 | Zhu |
| 2013/0255729 A1 | 10/2013 | Hodge et al. |
| 2016/0295859 A1 | 10/2016 | Chan et al. |
| 2017/0251663 A1 | 9/2017 | Man et al. |
| 2017/0347644 A1 | 12/2017 | Silvernail et al. |

FOREIGN PATENT DOCUMENTS

| | | |
|---|---|---|
| CN | 102696599 A | 10/2012 |
| CN | 104521959 A | 4/2015 |
| CN | 105129931 A | 12/2015 |
| CN | 105145631 A | 12/2015 |
| CN | 108882703 A | 11/2018 |
| DE | 2530522 A1 | 1/1977 |
| DE | 2936121 A1 | 3/1981 |
| DE | 3503848 A1 | 8/1986 |
| DE | 10060534 A1 | 6/2002 |
| EP | 0180841 A1 | 5/1986 |
| EP | 0593250 A1 | 4/1994 |
| EP | 0639636 A2 | 2/1995 |
| EP | 0799570 A1 | 10/1997 |
| EP | 0843002 A2 | 5/1998 |
| EP | 0843002 A3 | 9/2001 |
| EP | 1277403 A1 | 1/2003 |
| GB | 2172607 A | 9/1986 |
| JP | 61112002 A | 5/1986 |
| JP | 61272298 A | 12/1986 |
| JP | 7256266 A | 10/1995 |
| JP | 8259444 A | 10/1996 |
| JP | 10512015 A | 11/1998 |
| JP | 2000273004 A | 10/2000 |
| JP | 2002146400 A | 5/2002 |
| JP | 2002348593 A | 12/2002 |
| JP | 2006328170 A | 12/2006 |
| JP | 2007119753 A | 5/2007 |
| JP | 2008156521 A | 7/2008 |
| JP | 201037295 A | 2/2010 |
| JP | 201323642 A | 2/2013 |
| JP | 2015507676 A | 3/2015 |
| JP | 2019508498 A | 3/2019 |
| WO | 9427436 A1 | 12/1994 |
| WO | 9728238 A1 | 8/1997 |
| WO | 9844791 A1 | 10/1998 |
| WO | 9845392 A1 | 10/1998 |
| WO | 9907331 A1 | 2/1999 |
| WO | 0042137 A2 | 7/2000 |
| WO | 0049127 A1 | 8/2000 |
| WO | 0119507 A1 | 3/2001 |
| WO | 0194517 A1 | 12/2001 |
| WO | 0221916 A2 | 3/2002 |
| WO | 03053144 A1 | 7/2003 |
| WO | 2008024090 A2 | 2/2008 |
| WO | 2008049616 A1 | 5/2008 |
| WO | 2011083295 A1 | 7/2011 |
| WO | 2015145100 A1 | 10/2015 |
| WO | 2017151552 A1 | 9/2017 |

OTHER PUBLICATIONS

Ecolab USA Inc., PCT/US2017/019906, filed Feb. 28, 2017, "International Search Report" of the Israel Patent Office, 4 pages, dated Jun. 5, 2017.

Ecolab USA Inc., in connection with PCT/US2017/019895 filed Feb. 28, 2017, "The International Search Report and the Written Opinion of the International Searching Authority, or the Declaration", 37 pages, dated Jun. 15, 2017.

Ecolab USA Inc., in connection with PCT/US2017/019880 filed Feb. 28, 2017, "International Search Report", 34 pages, dated Jun. 13, 2017.

Ecolab USA Inc. in connection with PCT/US2017/19840 filed Feb. 28, 2017, "The International Search Report and the Written Opinion of the International Searching Authority, or the Declaration", 16 pages, dated Jun. 8, 2017.

European Patent Office, "Supplementary Partial European Search Report" in connection with EP 17839947, filed Jan. 24, 2019, 9 pages, completed Jan. 23, 2020.

Sütterlin et al., "The toxicity of the quaternary ammonium compound benzalkonium chloride alone and in mixtures with other anionic compounds to bacteria in test systems with Vibrio fischeri and Pseudomonas putida", Ecotoxicology and Environmental Safety, vol. 71, pp. 498-505, 2008.

European Patent Office, "Extended European Search Report", in connection with EP 17839947.3 filed Jan. 24, 2019, 20 pages, dated Jun. 15, 2020.

\* cited by examiner

INTERACTION BETWEEN ANTIMICROBIAL QUATERNARY COMPOUNDS AND ANIONIC SURFACTANTS

CROSS REFERENCE TO RELATED APPLICATIONS

This is a Continuation Application of U.S. Ser. No. 15/444,987, filed Feb. 28, 2017, which is a non-provisional application claiming priority to U.S. Provisional Application No. 62/373,772, filed Aug. 11, 2016, both of which are herein incorporated by reference in their entireties.

FIELD OF THE INVENTION

The present invention relates to antimicrobial compositions, including activated or inactivated antimicrobial compositions. In some embodiments, an antimicrobial quaternary ammonium compound is provided in combination with an anionic surfactant provide a composition having enhanced antimicrobial properties, which may include enhanced surface activity and/or sanitizing efficacy. In other aspects, an antimicrobial quaternary ammonium compound is provided in combination with an anionic polymer or chelant. In particular, the combination provides heightened antimicrobial activity as compared to either the anionic surfactant or the quaternary ammonium compound alone. In other embodiments, an antimicrobial quaternary ammonium compound is provided in combination with an anionic surfactant to provide a composition having inactivated antimicrobial properties. Beneficially, according to the invention an activated or inactivated composition is provided according to a particular application of use.

BACKGROUND OF THE INVENTION

Antimicrobial agents are chemical compositions that are used to prevent microbiological contamination and deterioration of products, materials, mediums (such as water process streams) and systems. Antimicrobial agents and compositions are used, for example, as disinfectants or sanitizers in association with hard surface cleaning, food preparation, animal feed, cooling water, hospitality services, hospital and medical uses, pulp and paper manufacturing, cleaning textiles, and water processing. Of the diverse categories of antimicrobial agents and compositions, quaternary ammonium compounds represent one of the largest of the classes of agents in use. At low concentrations, quaternary ammonium type antimicrobial agents are bacteriostatic, fungistatic, algistatic, sporostatic, and tuberculostatic. At medium concentrations they are bactericidal, fungicidal, algicidal, and viricidal against lipophilic viruses. Quaternary ammonium compounds are known to have difficulty in retaining kill efficacy against gram negative microbes, such as $E.\ coli$, below about 150 ppm and are also inefficient at reduced temperatures and pH. Therefore, it is desirable to boost the antimicrobial activity of a chemical such as a quaternary ammonium compound. It is desirable to boost the antimicrobial activity of such chemicals for us in various applications.

Accordingly, it is an objective of the claimed invention to develop an enhanced antimicrobial quaternary ammonium compound based composition.

It is a further object of the invention to provide a synergistic combination of a quaternary ammonium compound and anionic surfactant providing increased dynamic surface activity (as measured by a reduction in dynamic surface tension).

It is a further object of the invention to provide a synergistic composition of a quaternary ammonium compound and anionic polymers or chelants to provide such improvements and synergistic surface activity.

It is an object of the invention to provide an activated composition, having enhanced and/or synergistic surface activity, having applications of use including, for example, disinfectant and/or sanitizing surfaces, including high level disinfectants for medical instruments, antimicrobial lubricants, laundry cleaning and sanitizing, antimicrobials having enhanced mildness and reduced irritancy, enhanced combination products, third sink applications, and the like.

A further object of the invention is to provide enhanced antimicrobial activity and/or sanitizing activity with a blend of quaternary ammonium compound and anionic surfactant, including overcoming conventional limitations of quaternary ammonium compounds, including conventional requirements for neutral to alkaline pH for performance efficacy, hard water performance limitations requiring increased concentrations and need for higher concentrations of actives for efficacy.

A further aspect of the invention is to provide a sanitizing composition to improve upon the conventional quaternary ammonium compounds which are not very surface active themselves. In an aspect, the enhanced antimicrobial activity and/or sanitizing activity with a blend of quaternary ammonium compound and anionic surfactant, including enhanced wetting in some applications, unexpectedly provide such activity at pH neutral or above (as opposed to acidic pH conventionally employed, such as for 500 ppm water hardness suspension tests). In a further aspect, and as a further benefit of the invention, the compositions provide enhanced mildness and reduced irritation, along with leaving less residue on substrate surfaces.

A further object of the invention is to provide a blend of quaternary ammonium compound and anionic surfactant capable of inactivating antimicrobial and/or sanitizing efficacy by selection of anionic surfactant for the composition.

It is an object of the invention to provide an inactivated composition of the neutralized quaternary ammonium compound and anionic surfactants, having applications of use including, for example, water treatment, quaternary ammonium compound titration kits, recycling of surfactants, and the like.

Other objects, advantages and features of the present invention will become apparent from the following specification taken in conjunction with the accompanying drawings.

BRIEF SUMMARY OF THE INVENTION

The compositions according to the invention provide ability to enhance or inactivate the antimicrobial efficacy of quaternary ammonium compounds. In an aspect, the selected anionic surfactants disclosed herein provide such selection for providing an antimicrobial composition or an inactivated antimicrobial composition. According to an embodiment, anionic surfactants having strong ionic bonds serve to deactivate the antimicrobial efficacy of quaternary ammonium compounds whereas anionic surfactants with weaker ionic bonds provide an enhanced or "activated" antimicrobial efficacy of the quaternary ammonium compounds.

Compositions of the invention provide a quaternary ammonium compound in association with an anionic surfactant. In some embodiments quaternary ammoniums having carbon chains of less than 20 are included in compositions of the invention. Examples of quaternary ammonium compounds useful in the present invention include but are not limited to alkyl dimethyl benzyl ammonium chloride, alkyl dimethyl ethylbenzyl ammonium chloride, octyl decyl dimethyl ammonium chloride, dioctyl dimethyl ammonium chloride, and didecyl dimethyl ammonium chloride to name a few. A single quaternary ammonium or a combination of more than one quaternary ammonium may be included in compositions of the invention. Further examples of quaternary ammonium compounds useful in the present invention include but are not limited to benzethonium chloride, ethyl benzethonium chloride, myristyl trimethyl ammonium chloride, methyl benzethonium chloride, cetalkonium chloride, cetrimonium bromide (CTAB), carnitine, dofanium chloride, tetraethyl ammonium bromide (TEAB), domiphen bromide, benzododecinium bromide, benzoxonium chloride, choline, cocamidopropyl betaine (CAPB), and denatonium.

Compositions of the invention further include anionic surfactants which are selected for a desired antimicrobial or inactivated antimicrobial effect on the quaternary ammonium compound. As described according to the present invention, it has been found that the ability of a combination of quaternary ammonium compound and an anionic surfactant are capable to either enhance or deactivate the antimicrobial efficacy which can be selected based upon its surface activity. That is, if a combination is highly surface active (low surface tension) as compared to another combination, the combination having the highest surface activity may enhance the antimicrobial efficacy of the quaternary ammonium. In contrast, if a combination has lower surface activity (higher surface tension) as compared to another combination, the combination having the low surface activity neutralizes or deactivates the antimicrobial efficacy of the quaternary ammonium.

In certain preferred aspects, a combination of at least one quaternary ammonium compound and a carboxylate-based anionic surfactant provides improved antimicrobial activity compared to either of the components used alone. In preferred aspects, the synergistic combinations increase activity of quaternary ammonium compounds against a microbial load where neither the anionic surfactant nor the quaternary ammonium compound was effective alone. Hence, the compositions set forth possess advantages over existing antimicrobial treating agents and provide improved results. The combinations disclosed herein of an antimicrobial agent together with an anionic surfactant provide better results than when either of the individual components is employed separately. Examples of preferred carboxylate anionic surfactants for enhanced surface activity and antimicrobial efficacy of the quaternary ammonium compounds include carboxylates having a carbon chain of C6-C10. Examples of anionic carboxylate surfactants include organic acids such as hexanoic acid, heptanoic acid, octanoic acid, nonanoic acid, and decanoic acid. Examples of branched chain organic acids include ethylhexyl carboxylate, isononanoic acid, and tridecyl carboxylate. Examples of commercially available surfactants include Marlowet4539 (C9-alcohol polyethylene glycol ether carboxylic acid available from Sasol). In other embodiments, phosphate esters serve to enhance the antimicrobial activity of a quaternary ammonium compound.

Compositions of the invention further include anionic polymer or chelant. In an aspect, the composition is a silane free quaternary ammonium compound having less than a C20 chain length and in combination with an anionic polymer and/or chelant. In some aspects the anionic polymer and/or chelant used in combination with the quaternary ammonium compound is a polyacrylate, acrylamide, carboxylate, phosphinic acid or phosphonate salt, or mixture thereof. In an aspect, the composition has a pH of 3 or less. In a further aspect, the composition is substantially free of an oxidant. In further embodiments, the quaternary ammonium compound used in the compositions of the invention is comprised of a mixture of dialkyl quaternary ammonium and alkyl benzyl quaternary ammonium, and the anionic polymer is a polyacrylate, acrylamide, carboxylate, phosphinic acid or phosphonate salt, or mixture thereof.

In a preferred embodiment the quaternary ammonium compound used in the antimicrobial composition of the invention is comprised of a mixture of dialkyl quaternary ammonium and alkyl benzyl quaternary ammonium and the anionic surfactant is octanoic acid, nonanoic acid or decanoic acid or a mixture thereof.

In other preferred aspects, a combination of at least one quaternary ammonium compound and a sulfate or sulfonate-based anionic surfactant provides inactivated antimicrobial or surface activity of the quaternary ammonium compound. In certain preferred aspects, a combination of at least one quaternary ammonium compound and an anionic surfactant that have a stronger ionic bond deactivates the antimicrobial efficacy of quaternary ammonium compounds. Examples of commercially available sulfate or sulfonated anionic surfactants include X-AES ($C_{12-14}$-$(PO)_{1.6}$-$(EO)_2$-sulfate available from Huntsman Chemical), SLS (sodium lauryl sulfate), and SLES (sodium lauryl ether sulfate).

Methods of employing the compositions are also included in the embodiments of the invention.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive. These and other features, objects, and advantages, of the present invention will become apparent from the following detailed description of the invention.

BRIEF DESCRIPTION OF THE DRAWINGS

FIG. 4A shows evaluations with SLS. FIG. 4B shows evaluations with NAS-FAL. FIG. 4C shows evaluations with EH-S.

Figure 1:
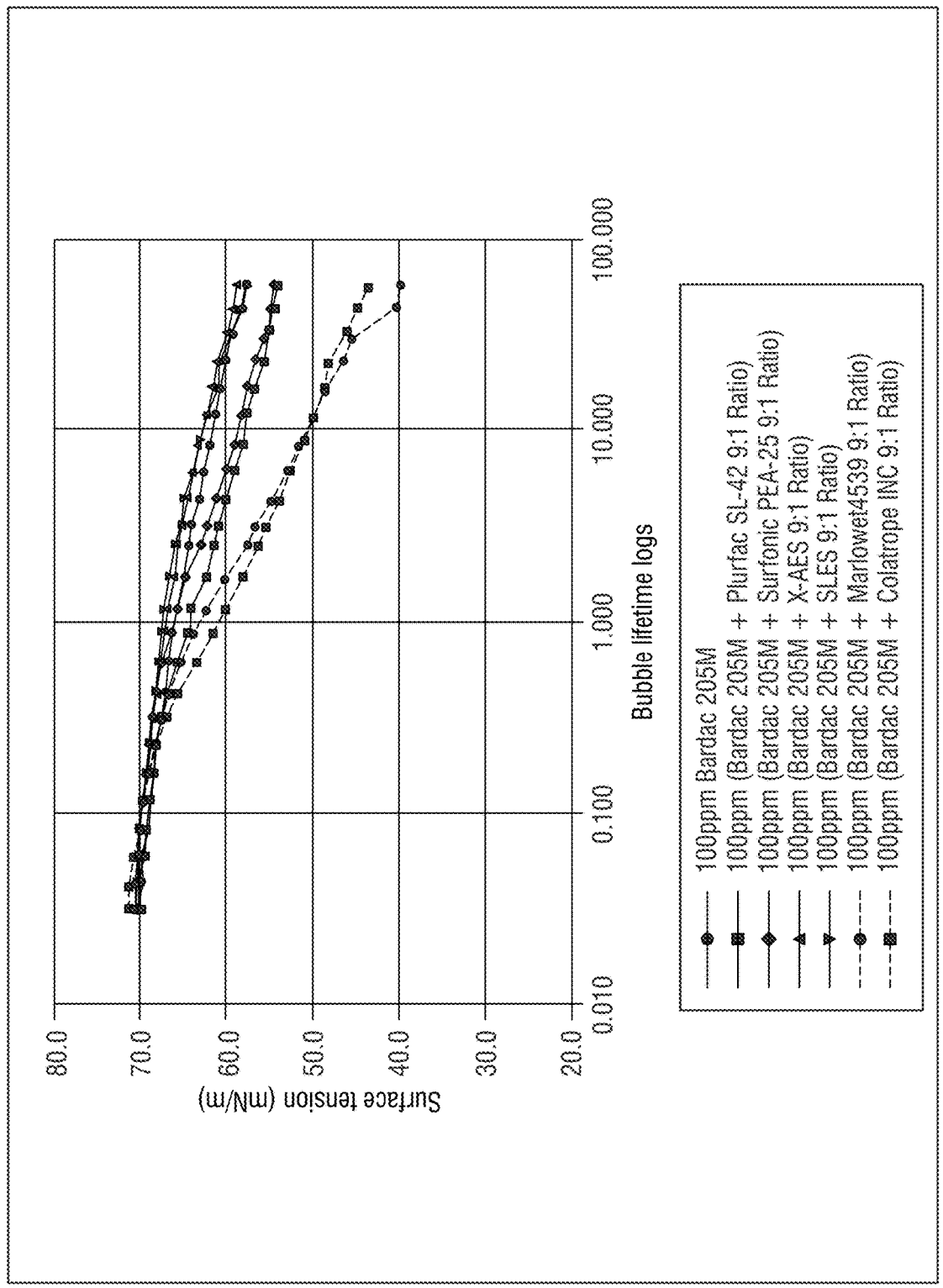
FIG. 1 is a plot showing Dynamic Surface Tension of compositions prepared with a 9:1 mass ratio of quaternary ammonium compound:anionic surfactant as evaluated according to embodiments of the invention.

Various embodiments of the present invention will be described in detail with reference to the drawings, wherein like reference numerals represent like parts throughout the several views. Reference to various embodiments does not limit the scope of the invention. Figures represented herein are not limitations to the various embodiments according to the invention and are presented for exemplary illustration of the invention.

DETAILED DESCRIPTION OF THE INVENTION

The embodiments of this invention are not limited to particular compositions, methods of making and/or methods of employing the same for hard surface cleaning, including antimicrobial and/or sanitizing applications for activated compositions, along with alternative cleaning and uses for inactivated compositions, which can vary and are understood by skilled artisans. So that the invention may be more readily understood, certain terms are first defined. It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers defining the range and include each integer within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

As used herein, the term "about" refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

The term "actives" or "percent actives" or "percent by weight actives" or "actives concentration" are used interchangeably herein and refers to the concentration of those ingredients involved in cleaning expressed as a percentage minus inert ingredients such as water or salts.

As used herein, the term "alkyl" or "alkyl groups" refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups).

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

As used herein, the term "cleaning" refers to a method used to facilitate or aid in soil removal, bleaching, microbial population reduction, and any combination thereof. As used herein, the term "microorganism" refers to any noncellular or unicellular (including colonial) organism. Microorganisms include all prokaryotes. Microorganisms include bacteria (including cyanobacteria), spores, lichens, fungi, protozoa, virinos, viroids, viruses, phages, and some algae. As used herein, the term "microbe" is synonymous with microorganism.

For the purpose of this patent application, successful microbial reduction is achieved when the microbial populations are reduced by at least about 50%, or by significantly more than is achieved by a wash with water. Larger reductions in microbial population provide greater levels of protection.

As used herein, the term "disinfectant" refers to an agent that kills all vegetative cells including most recognized pathogenic microorganisms, using the procedure described in *A.O.A.C. Use Dilution Methods*, Official Methods of Analysis of the Association of Official Analytical Chemists, paragraph 955.14 and applicable sections, 15th Edition, 1990 (EPA Guideline 91-2). As used herein, the term "high level disinfection" or "high level disinfectant" refers to a compound or composition that kills substantially all organisms, except high levels of bacterial spores, and is effected with a chemical germicide cleared for marketing as a sterilant by the Food and Drug Administration. As used herein, the term "intermediate-level disinfection" or "intermediate level disinfectant" refers to a compound or composition that kills mycobacteria, most viruses, and bacteria with a chemical germicide registered as a tuberculocide by the Environmental Protection Agency (EPA). As used herein, the term "low-level disinfection" or "low level disinfectant" refers to a compound or composition that kills some viruses and bacteria with a chemical germicide registered as a hospital disinfectant by the EPA.

As used herein, the phrase "food processing surface" refers to a surface of a tool, a machine, equipment, a structure, a building, or the like that is employed as part of a food processing, preparation, or storage activity. Examples of food processing surfaces include surfaces of food processing or preparation equipment (e.g., slicing, canning, or transport equipment, including flumes), of food processing wares (e.g., utensils, dishware, wash ware, and bar glasses), and of floors, walls, or fixtures of structures in which food processing occurs. Food processing surfaces are found and employed in food anti-spoilage air circulation systems, aseptic packaging sanitizing, food refrigeration and cooler cleaners and sanitizers, ware washing sanitizing, blancher cleaning and sanitizing, food packaging materials, cutting board additives, third-sink sanitizing, beverage chillers and warmers, meat chilling or scalding waters, autodish sanitizers, sanitizing gels, cooling towers, food processing antimicrobial garment sprays, and non-to-low-aqueous food preparation lubricants, oils, and rinse additives.

As used herein, the phrase "food product" includes any food substance that might require treatment with an antimicrobial agent or composition and that is edible with or without further preparation. Food products include meat (e.g. red meat and pork), seafood, poultry, produce (e.g., fruits and vegetables), eggs, living eggs, egg products, ready to eat food, wheat, seeds, roots, tubers, leafs, stems, corns, flowers, sprouts, seasonings, or a combination thereof. The term "produce" refers to food products such as fruits and vegetables and plants or plant-derived materials that are typically sold uncooked and, often, unpackaged, and that can sometimes be eaten raw.

As used herein, the phrase "health care surface" refers to a surface of an instrument, a device, a cart, a cage, furniture, a structure, a building, or the like that is employed as part of a health care activity. Examples of health care surfaces include surfaces of medical or dental instruments, of medical or dental devices, of electronic apparatus employed for monitoring patient health, and of floors, walls, or fixtures of structures in which health care occurs. Health care surfaces are found in hospital, surgical, infirmity, birthing, mortuary, and clinical diagnosis rooms. These surfaces can be those typified as "hard surfaces" (such as walls, floors, bed-pans, etc.), or fabric surfaces, e.g., knit, woven, and non-woven surfaces (such as surgical garments, draperies, bed linens, bandages, etc.), or patient-care equipment (such as respirators, diagnostic equipment, shunts, body scopes, wheel chairs, beds, etc.), or surgical and diagnostic equipment. Health care surfaces include articles and surfaces employed in animal health care.

As used herein, the term "instrument" refers to the various medical or dental instruments or devices that can benefit from cleaning with a composition according to the present invention.

As used herein, the phrases "medical instrument," "dental instrument," "medical device," "dental device," "medical equipment," or "dental equipment" refer to instruments, devices, tools, appliances, apparatus, and equipment used in medicine or dentistry. Such instruments, devices, and equipment can be cold sterilized, soaked or washed and then heat sterilized, or otherwise benefit from cleaning in a composition of the present invention. These various instruments, devices and equipment include, but are not limited to: diagnostic instruments, trays, pans, holders, racks, forceps, scissors, shears, saws (e.g. bone saws and their blades), hemostats, knives, chisels, rongeurs, files, nippers, drills, drill bits, rasps, burrs, spreaders, breakers, elevators, clamps, needle holders, carriers, clips, hooks, gouges, curettes, retractors, straightener, punches, extractors, scoops, keratomes, spatulas, expressors, trocars, dilators, cages, glassware, tubing, catheters, cannulas, plugs, stents, scopes (e.g., endoscopes, stethoscopes, and arthroscopes) and related equipment, and the like, or combinations thereof.

As used herein, the term "microbe" is synonymous with microorganism. For the purpose of this patent application, successful microbial reduction is achieved when the microbial populations are reduced by at least about 50%, or by significantly more than is achieved by a wash with water. Larger reductions in microbial population provide greater levels of protection. Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can affect two kinds of microbial cell damage. The first is a lethal, irreversible action resulting in complete microbial cell destruction or incapacitation. The second type of cell damage is reversible, such that if the organism is rendered free of the agent, it can again multiply. The former is termed microbiocidal and the later, microbiostatic. A sanitizer and a disinfectant are, by definition, agents which provide antimicrobial or microbiocidal activity. In contrast, a preservative is generally described as an inhibitor or microbiostatic composition.

As used herein, the term "microorganism" refers to any noncellular or unicellular (including colonial) organism. Microorganisms include all prokaryotes. Microorganisms include bacteria (including cyanobacteria), spores, lichens, fungi, protozoa, virinos, viroids, viruses, phages, and some algae.

As used herein, the term "sanitizer" refers to an agent that reduces the number of bacterial contaminants to safe levels as judged by public health requirements. In an embodiment, sanitizers for use in this invention will provide at least a 99.999% reduction (5-log order reduction). These reductions can be evaluated using a procedure set out in Germicidal and Detergent Sanitizing Action of Disinfectants, Official Methods of Analysis of the Association of Official Analytical Chemists, paragraph 960.09 and applicable sections, 15th Edition, 1990 (EPA Guideline 91-2). According to this reference a sanitizer should provide a 99.999% reduction (5-log order reduction) within 30 seconds at room temperature, 25±2° C., against several test organisms. According to embodiments of the invention, a sanitizing rinse provides a 99.999% reduction (5-log order reduction) of the desired organisms (including bacterial contaminants) at a use temperature. Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can affect two kinds of microbial cell damage. The first is a lethal, irreversible action resulting in complete microbial cell destruction or incapacitation. The second type of cell damage is reversible, such that if the organism is rendered free of the agent, it can again multiply. The former is termed microbiocidal and the later, microbiostatic. A sanitizer and a disinfectant are, by definition, agents which provide antimicrobial or microbiocidal activity. In contrast, a preservative is generally described as an inhibitor or microbiostatic composition As used herein, the term "substantially free" refers to compositions completely lacking the component or having such a small amount of the component that the component does not affect the performance of the composition. The component may be present as an impurity or as a contaminant and shall be less than 0.5 wt-%. In another embodiment, the amount of the component is less than 0.1 wt-% and in yet another embodiment, the amount of component is less than 0.01 wt-%.

The term "surfactant" as used herein is a compound that contains a lipophilic segment and a hydrophilic segment, which when added to water or solvents, reduces the surface tension of the system.

As used herein, the term "ware" refers to items such as eating and cooking utensils, dishes, and other hard surfaces such as showers, sinks, toilets, bathtubs, countertops, windows, mirrors, transportation vehicles, and floors. As used herein, the term "warewashing" refers to washing, cleaning, or rinsing ware. Ware also refers to items made of plastic. Types of plastics that can be cleaned with the compositions according to the invention include but are not limited to, those that include polycarbonate polymers (PC), acrylonitrile-butadiene-styrene polymers (ABS), and polysulfone polymers (PS). Another exemplary plastic that can be cleaned using the compounds and compositions of the invention include polyethylene terephthalate (PET).

As used herein, the term "waters" includes food process or transport waters. Food process or transport waters include produce transport waters (e.g., as found in flumes, pipe transports, cutters, slicers, blanchers, retort systems, washers, and the like), belt sprays for food transport lines, boot and hand-wash dip-pans, third-sink rinse waters, and the like. Waters also include domestic and recreational waters such as pools, spas, recreational flumes and water slides, fountains, and the like.

As used herein, "weight percent," "wt-%," "percent by weight," "% by weight," and variations thereof refer to the concentration of a substance as the weight of that substance divided by the total weight of the composition and multiplied by 100. It is understood that, as used here, "percent," "%," and the like are intended to be synonymous with "weight percent," "wt-%," etc.

As used herein, the term "water soluble" refers to a composition or a component if it is at least 90 percent soluble in water, at least 95 percent soluble in water, at least 98 percent soluble in water, at least 99 percent soluble in water, or at least 99.9 percent soluble in water.

The methods and compositions of the present invention may comprise, consist essentially of, or consist of the components and ingredients of the present invention as well as other ingredients described herein. As used herein, "consisting essentially of" means that the methods and compositions may include additional steps, components or ingredients, but only if the additional steps, components or ingredients do not materially alter the basic and novel characteristics of the claimed methods and compositions.

Activated Antimicrobial Compositions

According to the invention, the antimicrobial compositions combining at least one quaternary ammonium compound and at least one anionic surfactant provide improved antimicrobial activity than either of the components used alone. In some aspects, the antimicrobial compositions according to the invention beneficially provide synergistic surface activity (reduced dynamic surface tension) and are cost effective. It has further been discovered that combinations of synergistic antimicrobial and/or sanitizing efficacy also serve to reduce the unpleasant smell of certain anionic surfactants (e.g. C6-C10 carboxylated surfactants), such as fatty acids, providing a still further benefit of the compositions of the invention.

In an aspect, the antimicrobial compositions according to the invention comprise, consist of and/or consist essentially of a quaternary ammonium compound and an anionic surfactant and/or anionic acid. In another aspect, the antimicrobial compositions according to the invention comprise, consist of and/or consist essentially of a quaternary ammonium compound having each R group with a C20 or less chain length, and an anionic surfactant having a C10 or less chain length for linear or branched carboxylates. In an aspect the carboxylates may be alkoxylated or unalkoxylated. In another aspect, the antimicrobial compositions according to the invention comprise, consist of and/or consist essentially of a quaternary ammonium compound having each R group with a C20 or less chain length, and an anionic surfactant having a C13 or less chain length for alkoxylated anionic linear or branched carboxylates.

The antimicrobial compositions according to the invention overcome the insufficient surface activity of the quaternary ammonium compounds while providing efficacious antimicrobial and/or sanitizing capabilities. The compositions of quaternary ammonium compound and anionic surfactant become synergistically more surface active and efficacious, which beneficially provide improved performance under stressed conditions. In some aspects, the antimicrobial compositions are efficacious at neutral and/or alkaline pH (as opposed to lower pH range of about 1-5 required for EPA standards used in water hardness suspension testing). Beneficially, the selection of the anionic surfactant and quaternary ammonium compound activate (i.e. cause synergy) the quaternary ammonium compound to provide desired surface activity, including antimicrobial and/or sanitizing activity, as a result of the synergy and improved wettability of the compositions. In an aspect, and without being limited to a particular mechanism of action, the anionic surfactant having a C10 or less chain length provides the activation suitable for providing an antimicrobial composition according to the invention. This combination of quaternary ammonium compound and anionic surfactant having a desired anionic head group and chain length is a non-oxidative approach to enhancing the surface activity of and the antimicrobial efficacy of the quaternary ammonium compound complex in an unexpected manner. Moreover, the antimicrobial compositions provided have an enhanced mildness and reduced irritancy as a result of the neutralization or partial neutralization, as well as result in reduced residue on substrate surfaces.

According to some embodiments, the antimicrobial compositions according to the invention provide surface activation and synergy of the quaternary ammonium compound that are molar ratio dependent. In an aspect, the compositions include approximately a mole to mole ratio of quaternary ammonium compound and anionic surfactant. In other aspects, the compositions include up to about a 10 to about a 1 molar ratio of quaternary ammonium compound and anionic surfactant. In other aspects, the compositions include up to about 1 to about a 10 molar ratio of quaternary ammonium compound and anionic surfactant, or any combination thereof. In another embodiment the antimicrobial compositions are provided with a molar ratio of anionic surfactant to quaternary ammonium of about 1 mole anionic surfactant to about 1 mole of quaternary ammonium compound. In another embodiment the antimicrobial composition is provided with a molar ratio of anionic surfactant to quaternary ammonium compound of about 1.5 mole anionic surfactant to about 1 mole of quaternary ammonium compound. In another embodiment the antimicrobial composition is provided with a molar ratio of anionic surfactant to quaternary ammonium compound of about 1 mole anionic surfactant to about 10 moles of quaternary ammonium compound. In another embodiment the antimicrobial composition is provided with a molar ratio of anionic surfactant to quaternary ammonium compound of about 2 moles anionic surfactant to about 1 mole of quaternary ammonium compound.

Inactivated Antimicrobial Compositions (Inactivation of Antimicrobial QACs)

It has further been discovered that modifications to the antimicrobial compositions described herein can be made to preferentially select the at least one quaternary ammonium compound and at least one anionic surfactant to provide an inactivated composition. According to the invention, some anionic surfactants work to decrease the antimicrobial activity of the quaternary ammonium compound. In an aspect, sulfated and sulfonated anionic surfactants inactivate the antimicrobial activity of quaternary ammonium compounds. It is believed that anionic surfactants with a stronger ionic charge serve to deactivate the antimicrobial efficacy of quaternary ammonium compounds whereas anionic surfactants with a weaker ionic charge serve to enhance or activate the antimicrobial efficacy of quaternary ammonium compounds.

In an aspect, the inactivated antimicrobial compositions according to the invention comprise, consist of and/or consist essentially of a quaternary ammonium compound and an anionic surfactant. In another aspect, the inactivated antimicrobial compositions according to the invention comprise, consist of and/or consist essentially of a quaternary ammonium compound having each R group with a C20 or less chain length, and a sulfate or sulfonate anionic surfactant having an alkyl chain greater than C10 for linear or branched.

The inactivated antimicrobial compositions according to the invention desirably provide decreased surface activity of the quaternary ammonium compound for particular applications of use. Without being bound by theory, the present invention demonstrates that a complex, or ion pair, between a quat and anionic surfactant, because of the charge neutralization, effectively reduces the hydrophilic cross-sectional areas for both surfactants, making stacking in interfaces very favorable. The complex formation is so favorable that it can overcome the cohesive force between fatty acid molecules. According to an aspect of the invention, stronger ionic charge with certain anionic surfactants, such as sulfate or sulfonate anionic surfactants, effectively neutralizes (or partially neutralizes the quaternary ammonium ionic charge) or inactivates the antimicrobial quaternary ammonium compound.

According to some embodiments, the inactivated antimicrobial compositions according to the invention provide decrease surface activation of the quaternary ammonium compound that are molar ratio dependent. In an aspect, the compositions include approximately a mole to mole ratio of quaternary ammonium compound and anionic surfactant. In other aspects, the compositions include up to about a 10 to about a 1 molar ratio of quaternary ammonium compound and anionic surfactant. In other aspects, the compositions include up to about a 1 to about a 10 molar ratio of quaternary ammonium compound and anionic surfactant. In another embodiment the inactivated antimicrobial compositions are provided with a molar ratio of anionic surfactant to quaternary ammonium of about 1 mole anionic surfactant to about 1 mole of quaternary ammonium compound. In another embodiment the inactivated antimicrobial composition is provided with a molar ratio of anionic surfactant to quaternary ammonium compound of about 1.5 mole anionic surfactant to about 1 mole of quaternary ammonium compound. In another embodiment the inactivated antimicrobial composition is provided with a molar ratio of anionic surfactant to quaternary ammonium compound of about 1 mole anionic surfactant to about 10 moles of quaternary ammonium compound. In another embodiment the inactivated antimicrobial composition is provided with a molar ratio of anionic surfactant to quaternary ammonium compound of about 2 moles anionic surfactant to about 1 mole of quaternary ammonium compound.

EXEMPLARY EMBODIMENTS

Exemplary ranges of the activated or inactivated antimicrobial compositions according to the invention in concentrated liquid compositions are shown in Table 1 each in weight percentage.

TABLE 1

| Material | First Exemplary Range wt-% | Second Exemplary Range wt-% | Third Exemplary Range wt-% |
| --- | --- | --- | --- |
| Quaternary ammonium compound | 0.001-75 | 1-50 | 1-30 |
| Anionic surfactant or polymer or chelant | 0.0001-50 | 0.1-30 | 0.1-20 |
| Additional Functional Ingredients | 0-90 | 0-75 | 0-50 |

According to the invention, the concentrated antimicrobial compositions and/or inactivated antimicrobial compositions set forth in Table 1 have any suitable pH for applications of use, including from about 1 to about 12. However, according to aspects of the invention, the diluted use solutions may have acidic or neutral to alkaline pH depending upon a particular application of use thereof, including form about 1 to about 12.

In some aspects, such as applications of a use solution of the antimicrobial compositions and/or inactivated antimicrobial compositions may have a pH from about 1 to about 12. In other aspects, the compositions of the invention have a pH between about 1 and about 7. In other aspects, the compositions of the invention have a pH between about 1 and about 5.5. In still other aspects, the compositions of the invention have a pH between about 1 and about 4. In another embodiment the composition has a pH between about 2 and about 7, between about 3 and about 7, between about 4 and about 7, between about 5 and about 7, between about 6 and about 7. In another embodiment the composition has a pH between about 1 and about 6, between about 1 and about 5, between about 1 and about 4, between about 1 and about 3, between about 1 and about 2. In yet other embodiments the composition has a pH between about 2 and about 6, between about 3 and about 6, between about 4 and about 6, between about 5 and about 6. In yet other embodiments the composition has a pH between about 1 and about 5, between about 2 and about 5, between about 3 and about 5, between about 4 and about 5. In yet other embodiments the composition has a pH between about 1 and about 4, between about 2 and about 4, between about 3 and about 4. Without limiting the scope of invention, the numeric ranges are inclusive of the numbers defining the range and include each integer within the defined range.

Quaternary Ammonium Compound

The antimicrobial compositions and inactivated antimicrobial compositions according to the invention include at least one quaternary ammonium compound. Certain quaternary ammonium compounds are known to have antimicrobial activity. Accordingly, various quaternary ammonium compound with antimicrobial activity can be used in the composition of the invention. In an aspect, the quaternary ammonium compound is an antimicrobial "quat." The term "quaternary ammonium compound" or "quat" generally refers to any composition with the following formula:

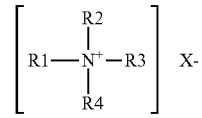

where R1-R4 are alkyl groups that may be alike or different, substituted or unsubstituted, saturated or unsaturated, branched or unbranched, and cyclic or acyclic and may contain ether, ester, or amide linkages; they may be aromatic or substituted aromatic groups. In an aspect, groups R1, R2, R3, and R4 each have less than a C20 chain length. X— is an anionic counterion. The term "anionic counterion" includes any ion that can form a salt with quaternary ammonium. Examples of suitable counterions include halides such as chlorides and bromides, propionates, methosulphates, saccharinates, ethosulphates, hydroxides, acetates, phosphates, carbonates (such as commercially available as Carboquat H, from Lonza), and nitrates. Preferably, the anionic counterion is chloride.

Compositions of the invention provide a quaternary ammonium compound in association with an anionic surfactant. In some embodiments quaternary ammoniums having carbon chains of less than 20 are included in compositions of the invention. Examples of quaternary ammonium compounds useful in the present invention include but are not limited to alkyl dimethyl benzyl ammonium chloride, alkyl dimethyl ethylbenzyl ammonium chloride, octyl decyl dimethyl ammonium chloride, dioctyl dimethyl ammonium chloride, and didecyl dimethyl ammonium chloride to name a few. A single quaternary ammonium or a combination of more than one quaternary ammonium may be included in compositions of the invention. Further examples of quaternary ammonium compounds useful in the present invention include but are not limited to benzethonium chloride, ethyl benzethonium chloride, myristyl trimethyl ammonium chloride, methyl benzethonium chloride, cetalkonium chloride, cetrimonium bromide (CTAB), carnitine, dofanium chloride, tetraethyl ammonium bromide (TEAB), domiphen bromide, benzododecinium bromide, benzoxonium chloride, choline, cocamidopropyl betaine (CAPB), and denatonium.

In some embodiments quaternary ammoniums having carbon chains of less than 20 or C2-C20 are included in compositions of the invention. In other embodiments quaternary ammoniums having carbon chains of C6-C18, C12-C18, C12-C16 and C6-C10 are included in compositions of the invention. Examples of quaternary ammonium compounds useful in the present invention include but are not limited to alkyl dimethyl benzyl ammonium chloride, alkyl dimethyl ethylbenzyl ammonium chloride, octyl decyl dimethyl ammonium chloride, dioctyl dimethyl ammonium chloride, and didecyl dimethyl ammonium chloride to name a few. A single quaternary ammonium or a combination of more than one quaternary ammonium may be included in compositions of the invention. Further examples of quaternary ammonium compounds useful in the present invention include but are not limited to benzethonium chloride, ethylbenzyl alkonium chloride, myristyl trimethyl ammonium chloride, methyl benzethonium chloride, cetalkonium chloride, cetrimonium bromide (CTAB), carnitine, dofanium chloride, tetraethyl ammonium bromide (TEAB), domiphen bromide, benzododecinium bromide, benzoxonium chloride, choline, cocamidopropyl betaine (CAPB), denatonium, and mixtures thereof. In an aspect, combinations of quaternary ammonium compounds are particularly preferred for compositions of the invention, such as for example the commercially-available products Bardac 205/208M.

In some embodiments depending on the nature of the R group, the anion, and the number of quaternary nitrogen atoms present, the antimicrobial quaternary ammonium compounds may be classified into one of the following categories: monoalkyltrimethyl ammonium salts; monoalkyldimethylbenzyl ammonium salts; dialkyldimethyl ammonium salts; heteroaromatic ammonium salts; polysubstituted quaternary ammonium salts; bis-quaternary ammonium salts; and polymeric quaternary ammonium salts. Each category will be discussed herein.

Monoalkyltrimethyl ammonium salts contain one R group that is a long-chain alkyl group, and the remaining R groups are short-chain alkyl groups, such as methyl or ethyl groups. Some non-limiting examples of monoalkyltrimethyl ammonium salts include cetyltrimethylammonium bromide, commercial available under the tradenames Rhodaquat M242C/29 and Dehyquart A; alkyltrimethyl ammonium chloride, commercially available as Arquad 16; alkylaryltrimethyl ammonium chloride; and cetyldimethyl ethylammonium bromide, commercially available as Ammonyx DME.

Monoalkyldimethylbenzyl ammonium salts contain one R group that is a long-chain alkyl group, a second R group that is a benzyl radical, and the two remaining R groups are short-chain alkyl groups, such as methyl or ethyl groups. Monoalkyldimethylbenzyl ammonium salts are generally compatible with nonionic surfactants, detergent builders, perfumes, and other ingredients. Some non-limiting examples of monoalkyldimethylbenzyl ammonium salts include alkyldimethylbenzyl ammonium chlorides, commercially available as Barquat from Lonza Inc.; and benzethonium chloride, commercially available as Lonzagard, from Lonza Inc. Additionally, the monoalkyldimethylbenzyl ammonium salts may be substituted. Non-limiting examples of such salts include dodecyldimethyl-3,4-dichlorobenzyl ammonium chloride. Finally, there are mixtures of alkyldimethylbenzyl and alkyldimethyl substituted benzyl (ethylbenzyl) ammonium chlorides commercially available as BTC 2125M from Stepan Company, and Barquat 4250 from Lonza Inc.

Dialkyldimethyl ammonium salts contain two R groups that are long-chain alkyl groups, and the remaining R groups are short-chain alkyl groups, such as methyl groups. Some non-limiting examples of dialkyldimethyl ammonium salts include didecyldimethyl ammonium halides, commercially available as Bardac 22 from Lonza Inc.; didecyl dimethyl ammonium chloride commercially available as Bardac 2250 from Lonza Inc.; dioctyl dimethyl ammonium chloride, commercially available as Bardac LF and Bardac LF-80 from Lonza Inc.); and octyl decyl dimethyl ammonium chloride sold as a mixture with didecyl and dioctyl dimethyl ammonium chlorides, commercially available as Bardac2050 and 2080 from Lonza Inc.

Heteroaromatic ammonium salts contain one R group that is a long-chain alkyl group, and the remaining R groups are provided by some aromatic system. Accordingly, the quaternary nitrogen to which the R groups are attached is part of an aromatic system such as pyridine, quinoline, or isoquinoline. Some non-limiting examples of heteroaromatic ammonium salts include cetylpyridinium halide, commercially available as Sumquat 6060/CPC from Zeeland Chemical Inc.; 1-[3-chloroalkyl]-3,5,7-triaza-1-azoniaadamantane, commercially available as Dowicil 200 from The Dow Chemical Company; and alkyl-isoquinolinium bromide.

Polysubstituted quaternary ammonium salts are a monoalkyltrimethyl ammonium salt, monoalkyldimethylbenzyl ammonium salt, dialkyldimethyl ammonium salt, or heteroaromatic ammonium salt wherein the anion portion of the molecule is a large, high-molecular weight (MW) organic ion. Some non-limiting examples of polysubstituted quaternary ammonium salts include alkyldimethyl benzyl ammonium saccharinate, and dimethylethylbenzyl ammonium cyclohexylsulfamate.

Bis-quaternary ammonium salts contain two symmetric quaternary ammonium moieties having the general formula:

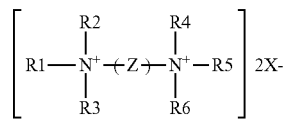

Where the R groups may be long or short chain alkyl, a benzyl radical or provided by an aromatic system. Z is a carbon-hydrogen chain attached to each quaternary nitrogen. Some non-limiting examples of bis-quaternary ammonium salts include 1,10-bis(2-methyl-4-aminoquinolinium chloride)-decane; and 1,6-bis[1-methyl-3-(2,2,6-trimethyl cyclohexyl)-propyldimethylammonium chloride] hexane or triclobisonium chloride.

In an aspect, the quaternary ammonium compound is a medium to long chain alkyl R group, such as from 8 carbons to about 20 carbons, from 8 carbons to about 18 carbons, from about 10 to about 18 carbons, and from about 12 to about 16 carbons, and providing a soluble and good antimicrobial agent.

In an aspect, the quaternary ammonium compound is a short di-alkyl chain quaternary ammonium compound having an R group, such as from 2 carbons to about 12 carbons, from 3 carbons to about 12 carbons, or from 6 carbons to about 12 carbons.

In a preferred aspect, the quaternary ammonium compound is an alkyl benzyl ammonium chloride, a dialkyl benzyl ammonium chloride, a blend of alkyl benzyl ammonium chloride and dialkyl benzyl ammonium chloride, didecyl dimethyl ammonium chloride, dioctyl dimethyl ammonium chloride, a blend of didecyl dimethyl ammonium chloride and dioctyl dimethyl ammonium chloride, or mixtures thereof. In a preferred embodiment the quaternary ammonium compound used in the antimicrobial compositions of the invention is comprised of a mixture of dialkyl quaternary ammonium and alkyl benzyl quaternary ammonium.

In some embodiments, the quaternary ammonium compound is silane free. In preferred embodiments, the antimicrobial composition is provided including a silane free quaternary ammonium compound having less than a C-20 chain length.

In a preferred embodiment, the quaternary ammonium compound may be selected based on its consideration or classification as a food additive. For example, the quaternary ammonium compound may include benzalkonium chloride and is therefore suitable for use in a sanitizing rinse for contact with food products.

According to embodiments of the invention providing antimicrobial compositions, an effective amount of the quaternary ammonium compound is provided in combination with the anionic surfactant to provide synergistic antimicrobial efficacy against a broad spectrum of microbes, including gram negative microbes such as E. coli. Suitable concentrations of the quaternary ammonium compound in such a use solution include at least about 10 ppm, at least about 50 ppm, or at least about 100 ppm, or at least about 150 ppm, or at least about 200 ppm, or at least about 250 ppm, or at least about 300 ppm, or from about 100-500 ppm, or from about 100-300 ppm, or any ranges therein. In some aspects, the activated microbial compositions according to the invention provide efficacy against gram negative conventionally requirement more than 150 ppm quaternary ammonium compounds for any antimicrobial efficacy at concentrations below about 150 ppm, or below about 100 ppm according to the synergy in combination with the anionic surfactants and/or acids. Beneficially, the low actives of the quaternary ammonium compound is a result of the beneficial synergy with the anionic surfactant. Without being limited according to the invention, all ranges recited are inclusive of the numbers defining the range and include each integer within the defined range.

According to embodiments of the invention providing inactivated antimicrobial compositions, an effective amount of the quaternary ammonium compound is provided in combination with the anionic surfactant to provide an inactivated quaternary ammonium composition, such as may be desired not impact the antimicrobial efficacy of a treated system. Suitable concentrations of the quaternary ammonium compound in such a use solution include at least about 0.0001 ppm, at least about 0.001 ppm, or at least about 0.01 ppm, or any ranges therein, or any suitable molar concentration of the inactivating anionic to the quaternary ammonium compound concentration for a particular application of use. Without being limited according to the invention, all ranges recited are inclusive of the numbers defining the range and include each integer within the defined range.

Additional suitable concentrations of the quaternary ammonium compound in a use solution for the antimicrobial compositions and inactivated antimicrobial compositions include between about 1 ppm and about 10,000 ppm, 1 ppm and about 1,000 ppm, 5 ppm and about 400 ppm, 10 ppm and about 400 ppm, 20 ppm and about 400 ppm, 25 ppm and about 400 ppm, 50 ppm and about 400 ppm, 75 ppm and about 400 ppm, or 100 ppm and about 400 ppm. Without being limited according to the invention, all ranges recited are inclusive of the numbers defining the range and include each integer within the defined range.

According to embodiments of the invention, the quaternary ammonium compound may be provided in a concentrated composition in the amount between about 0.001 wt.-%-75 wt.-%, from about 0.1 wt.-%-75 wt.-%, from about 0.01 wt.-%-75 wt.-%, from about 1 wt.-%-75 wt.-%, from about 1 wt.-%-50 wt.-%, from about 1 wt.-%-30 wt.-%, from about 5 wt.-%-30 wt.-%. In addition, without being limited according to the invention, all ranges recited are inclusive of the numbers defining the range and include each integer within the defined range.

Anionic Surfactants

The antimicrobial compositions and/or inactivated antimicrobial compositions according to the invention include at least one anionic surfactant. In other aspects, the antimicrobial compositions and/or inactivated antimicrobial compositions according to the invention include at least two anionic surfactants. Anionic surfactants are categorized as anionics because the charge on the hydrophile is negative; or surfactants in which the hydrophilic section of the molecule carries no charge unless the pH is elevated to pKa or neutrality or above (e.g. carboxylic acids). Carboxylate, sulfonate, sulfate and phosphate are polar (hydrophilic) solubilizing groups found in anionic surfactants.

In an aspect, the anionic surfactant is linear or branched. In an aspect, the linear or branched anionic surfactant is a medium chain surfactant having from 6-20 carbon chain length, or from 6-18 carbon chain length, preferably from 6-12 carbon chain length, and more preferably from 6-10 carbon chain length. In an aspect, the linear or branched, medium chain anionic surfactant is alkoxylated. In an aspect, the linear or branched anionic surfactant is an alkoxylated medium chain surfactant having from 6-18 carbon chain length, preferably from 6-13 carbon chain length, and more preferably from 6-10 carbon. In an aspect, the anionic surfactant is a carboxylate. In an alternative aspect, the anionic surfactant is a weak acid anionic, such as a phosphate ester. In a still further alternative aspect, the anionic surfactant is a sulfonate and/or sulfate. In still further aspect, the anionic surfactant used in combination with the quaternary ammonium is alkoxylated or un-alkoxylated and may be a primary linear chain or branched chain carboxylate.

In an aspect, the anionic surfactant suitable for use in the present compositions to activate the synergy and enhanced surface activity of the quaternary ammonium compound include carboxylates. Anionic carboxylate surfactants suitable for use in the present compositions include carboxylic acids (and salts), such as alkanoic acids (and alkanoates), ester carboxylic acids (e.g. alkyl succinates), ether carboxylic acids, sulfonated fatty acids, such as sulfonated oleic acid, and the like Suitable carboxylic acids include for example decanoic acid, octanoic acid, nonanoic, ethylhexyl acid, and isononanioic acid. Such carboxylates include alkyl ethoxy carboxylates, alkyl aryl ethoxy carboxylates, alkyl polyethoxy polycarboxylate surfactants and soaps (e.g. alkyl carboxyls). Secondary carboxylates useful in the present compositions include those which contain a carboxyl unit connected to a secondary carbon. The secondary carbon can be in a ring structure, e.g. as in p-octyl benzoic acid, or as in alkyl-substituted cyclohexyl carboxylates. The secondary carboxylate surfactants typically contain no ether linkages, no ester linkages and no hydroxyl groups. Further, they typically lack nitrogen atoms in the head-group (amphiphilic portion). Suitable secondary soap surfactants typically contain 11-13 total carbon atoms, although more carbons atoms (e.g., up to 16) can be present. Suitable carboxylates also include acylamino acids (and salts), such as acylgluamates, acyl peptides, sarcosinates (e.g. N-acyl sarcosinates), taurates (e.g. N-acyl taurates and fatty acid amides of methyl tauride), and the like.

Suitable anionic surfactants include alkyl or alkylaryl ethoxy carboxylates of the following formula: R—O—$(CH_2CH_2O)_n(CH_2)_m$—$CO_2X$ in which R is a C8-C22 alkyl group or

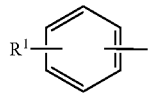

in which R1 is a C4-C16 alkyl group; n is an integer of 1-20; m is an integer of 1-3; and X is a counter ion, such as hydrogen, sodium, potassium, lithium, ammonium, or an amine salt such as monoethanolamine, diethanolamine or triethanolamine. In some embodiments, n is an integer of 4 to 10 and m is 1. In some embodiments, R is a C8-C16 alkyl group. In some embodiments, R is a C12-C14 alkyl group, n is 4, and m is 1.

Such alkyl and alkylaryl ethoxy carboxylates are commercially available. These ethoxy carboxylates are typically available as the acid forms, which can be readily converted to the anionic or salt form.

In an aspect, the carboxylate-based anionic surfactant provides improved antimicrobial activity than either of the components used alone. Examples of preferred activating anionic surfactants include carboxylates having a carbon chain of C6-C10. Examples of anionic carboxylate surfactants include organic acids such as hexanoic acid, heptanoic acid, octanoic acid, nonanoic acid, and decanoic acid. Examples of branched chain organic acids include ethylhexyl carboxylate and tridecyl carboxylate. Examples of commercially available surfactants include Marlowet 4539 (C9-alcohol polyethylene glycol ether carboxylic acid available from Sasol), Emulsogen CNO (C8-alcohol 8 moles polyethylene glycol ether carboxylic acid available from Clariant), and Emulsogen DTC (C13-alcohol 7 moles polyethylene glycol ether carboxylic acid available from Clariant), and others.

In an aspect, the anionic surfactant suitable for use in the present compositions to activate the microbial synergy and enhanced surface activity (as measured by a reduction in dynamic surface tension) of the quaternary ammonium compound further include phosphate esters.

In an aspect, the anionic surfactant suitable for use in the present compositions to inactivate or decrease the surface activity of the quaternary ammonium compound include sulfonates and/or sulfates. In an aspect, the anionic surfactant suitable for use in the present compositions include alkyl ether sulfates, alkyl sulfates, the linear and branched primary and secondary alkyl sulfates, alkyl ethoxysulfates, fatty oleyl glycerol sulfates, alkyl phenol ethylene oxide ether sulfates, the C5-C17 acyl-N—(C1-C4 alkyl) and —N—(C1-C2 hydroxyalkyl) glucamine sulfates, and sulfates of alkylpolysaccharides such as the sulfates of alkylpolyglucoside, and the like. Also included are the alkyl sulfates, alkyl poly(ethyleneoxy) ether sulfates and aromatic poly(ethyleneoxy) sulfates such as the sulfates or condensation products of ethylene oxide and nonyl phenol (usually having 1 to 6 oxyethylene groups per molecule). Anionic sulfonate surfactants suitable for use in the present compositions also include alkyl sulfonates, the linear and branched primary and secondary alkyl sulfonates, and the aromatic sulfonates with or without substituents.

In an aspect, the sulfated and sulfonated anionic surfactants provide decreased or inactivated surface activity of the quaternary ammonium compound. Sulfated and sulfonated anionic surfactants have a stronger ionic bond serve to deactivate the antimicrobial efficacy of quaternary ammonium compounds whereas anionic surfactants with weaker ionic bonds serve to enhance or activate the antimicrobial efficacy of quaternary ammonium compounds. Examples of commercially available sulfate or sulfonated anionic surfactants include X-AES ($C_{12-14}$-$(PO)_{16}$-$(EO)_2$-sulfate available from Huntsman Chemical), SLS (sodium lauryl sulfate), SLES (sodium lauryl ether sulfate), LAS (linear alkyl benzyl sulfonate), and AOS (alpha olefin sulfonate).

As described herein according to the invention, the ability of a combination of quaternary ammonium compound and an anionic surfactant to either enhance or deactivate the antimicrobial efficacy can be predicted based upon its surface activity. That is, if a combination is highly surface active as compared to another combination (which indicates the quaternary ammonium compound is water soluble and therefore available for surface activity and antimicrobial action), the combination having the highest surface activity enhances the antimicrobial efficacy of the quaternary ammonium. In contrast, if a combination has lower surface activity as compared to another combination, the combination having the low surface activity neutralizes or deactivates the antimicrobial efficacy of the quaternary ammonium.

In an aspect of the invention, the antimicrobial efficacy of a composition may be dialed up or down depending upon the anionic surfactant employed. According to the invention, a method of modulating antimicrobial activity of a quaternary ammonium compound is provided.

According to embodiments of the invention providing antimicrobial compositions, an effective amount of the anionic surfactant is provided in combination with the quaternary ammonium compound to provide synergistic antimicrobial efficacy. Suitable concentrations of the anionic surfactant in a use solution include between about 1 ppm and about 5,000 ppm, about 15 ppm and about 2,500 ppm, about 1 ppm and about 1,000 ppm, about 1 ppm and about 100 ppm, about 1 ppm and about 50 ppm, or about 1 ppm and about 5 ppm. Without being limited according to the invention, all ranges recited are inclusive of the numbers defining the range and include each integer within the defined range.

According to other embodiments of the invention providing inactivated antimicrobial compositions, an effective amount of the anionic surfactant is provided in combination with the quaternary ammonium compound to inactivate or decrease antimicrobial efficacy of the quaternary ammonium compound. Suitable concentrations of the anionic surfactant in a use solution include between about 1 ppm and about 5,000 ppm, about 15 ppm and about 2,500 ppm, about 1 ppm and about 1,000 ppm, about 1 ppm and about 100 ppm, about 1 ppm and about 50 ppm, or about 1 ppm and about 25 ppm.

According to embodiments of the invention, the anionic surfactant may be provided in a concentrated composition in the amount between about 0.0001 wt.-%-50 wt.-%, from about 0.001 wt.-%-50 wt.-%, from about 0.01 wt.-%-50 wt.-%, from about 0.1 wt.-%-50 wt.-%, from about 0.1 wt.-%-30 wt.-%, from about 1 wt.-%-30 wt.-%, from about 0.1 wt.-%-20 wt.-%, or from about 1 wt.-%-20 wt.-%. In addition, without being limited according to the invention, all ranges recited are inclusive of the numbers defining the range and include each integer within the defined range. As one skilled in the art will ascertain from the disclosure of the present invention, the concentrations for the anionic surfactant and/or acid in combination with the quaternary ammonium compound will vary dependent upon the type of anionic surfactant (e.g. selected for activation versus inactivation), quaternary ammonium compound concentration (molar ratio) and the additional components in the solution of the composition.

Anionic Polymers and/or Chelants

In some embodiments, the compositions according to the invention include at least one anionic polymer or chelant in combination with the quaternary ammonium compound to provide the surface active complex. In other aspects, the compositions according to the invention include at least two anionic polymers, or an anionic polymer and an anionic surfactant. In other aspects, the compositions according to the invention include at least two anionic chelants, or an anionic polymer and an anionic chelant, or an anionic chelant and an anionic surfactant. Anionic polymers and chelants are categorized as anionics because the charge on the hydrophobe is negative; or surfactants in which the hydrophobic section of the molecule carries no charge unless the pH is elevated to neutrality or above (e.g. carboxylic acids). Carboxylate, sulfonate, sulfate and phosphate are polar (hydrophilic) solubilizing groups found in anionic compounds. Of the cations (counter ions) associated with these polar groups, sodium, lithium and potassium impart water solubility; ammonium and substituted ammonium ions provide both water and oil solubility; and, calcium, barium, and magnesium promote oil solubility.

It is further discovered according to the invention that phosphate esters serve to enhance the surface activity and antimicrobial activity of a quaternary ammonium compound and are therefore suitable for use in the activated compositions. In an aspect, a phosphosuccinate adducts/oligomer (PSO) are particularly well suited for the activated compositions according to the invention.

In an aspect, the anionic polymer or chelant is linear or branched. In an aspect, the linear or branched anionic is a medium chain compound having from 6-18 carbon chain length, preferably from 6-10 carbon chain length, and more preferably from 6-9 carbon chain length. In an aspect, the linear or branched, medium chain anionic is alkoxylated or un-alkoxylated. In an aspect, the anionic polymer or chelant is a carboxylate. In a still further alternative aspect, the anionic polymer or chelant is a sulfonate and/or sulfate.

In an aspect, the anionic polymer or chelant suitable for use in the present compositions include carboxylates. Anionic carboxylate suitable for use in the present compositions include carboxylic acids (and salts), such as alkanoic acids (and alkanoates), ester carboxylic acids (e.g. alkyl succinates), ether carboxylic acids, sulfonated fatty acids, such as sulfonated oleic acid, and the like. Such carboxylates include alkyl ethoxy carboxylates, alkyl aryl ethoxy carboxylates, and alkyl polyethoxy polycarboxylates. Secondary carboxylates useful in the present compositions include those which contain a carboxyl unit connected to a secondary carbon. The secondary carbon can be in a ring structure, e.g. as in p-octyl benzoic acid, or as in alkyl-substituted cyclohexyl carboxylates. The secondary carboxylate surfactants typically contain no ether linkages, no ester linkages and no hydroxyl groups. Further, they typically lack nitrogen atoms in the head-group (amphiphilic portion). Suitable secondary soap surfactants typically contain 11-13 total carbon atoms, although more carbons atoms (e.g., up to 16) can be present. Suitable carboxylates also include acylamino acids (and salts), such as acylgluamates, acyl peptides, sarcosinates (e.g. N-acyl sarcosinates), taurates (e.g. N-acyl taurates and fatty acid amides of methyl tauride), and the like.

In an aspect, the anionic polymer or chelant suitable for use in the present compositions include polycarboxylates. Particularly suitable polycarboxylates include, for example, polyacrylates and acrylamides. Further suitable polycarboxylates include, for example, polyacrylic acid, maleic/olefin copolymer, acrylic/maleic copolymer, polymethacrylic acid, acrylic acid-methacrylic acid copolymers, hydrolyzed polyacrylamide, hydrolyzed polymethacrylamide, hydrolyzed polyamide-methacrylamide copolymers, hydrolyzed polyacrylonitrile, hydrolyzed polymethacrylonitrile, hydrolyzed acrylonitrile-methacrylonitrile copolymers, polymaleic acid, polyfumaric acid, copolymers of acrylic and itaconic acid, phosphino polycarboxylate, acid or salt forms thereof, mixtures thereof, and the like. A suitable commercially available maleic homopolymer is Aquatreat AR-801 (low molecular weight partially neutralized maleic homopolymer). In another aspect, hydrated or water soluble salts or partial salts of these polymers or copolymers such as their respective alkali metal (for example, sodium or potassium) or ammonium salts may also be used. The weight average molecular weight of the polymers is from about 4000 to about 12,000. A suitable commercially available polyacrylic acid polymers is Acusol 445N, available from Rohm & Haas LLC. Preferred polymers include polyacrylic acid, the partial sodium salts of polyacrylic acid or sodium polyacrylate having an average molecular weight within the range of 4000 to 8000.

Suitable anionics include alkyl or alkylaryl ethoxy carboxylates of the following formula: $R-O-(CH_2CH_2O)_n(CH_2)_m-CO_2X$ in which R is a C8-C22 alkyl group or

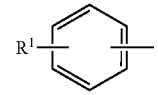

in which $R^1$ is a C4-C16 alkyl group; n is an integer of 1-20; m is an integer of 1-3; and X is a counter ion, such as hydrogen, sodium, potassium, lithium, ammonium, or an amine salt such as monoethanolamine, diethanolamine or triethanolamine. In some embodiments, n is an integer of 4 to 10 and m is 1. In some embodiments, R is a C8-C16 alkyl group. In some embodiments, R is a C12-C14 alkyl group, n is 4, and m is 1.

Such alkyl and alkylaryl ethoxy carboxylates are commercially available. These ethoxy carboxylates are typically available as the acid forms, which can be readily converted to the anionic or salt form.

In an aspect, the anionic polymer or chelant suitable for use in the present compositions include sulfonates and/or sulfates. In an aspect, the anionic suitable for use in the present compositions include alkyl ether sulfates, alkyl sulfates, the linear and branched primary and secondary alkyl sulfates, alkyl ethoxysulfates, fatty oleyl glycerol sulfates, alkyl phenol ethylene oxide ether sulfates, the C5-C17 acyl-N—(C1-C4 alkyl) and —N—(C1-C2 hydroxyalkyl) glucamine sulfates, and sulfates of alkylpolysaccharides such as the sulfates of alkylpolyglucoside, and the like. Also included are the alkyl sulfates, alkyl poly (ethyleneoxy) ether sulfates and aromatic poly(ethyleneoxy) sulfates such as the sulfates or condensation products of ethylene oxide and nonyl phenol (usually having 1 to 6 oxyethylene groups per molecule). Anionic sulfonates suitable for use in the present compositions also include alkyl sulfonates, the linear and branched primary and secondary alkyl sulfonates, and the aromatic sulfonates with or without substituents.

In some embodiments, the compositions of the present invention include one or more anionic chelating agents in combination with the quaternary ammonium compound to provide the surface active complex. Chelating agents include, for example, chelating agents or sequestrants. Suitable sequestrants include, but are not limited to, organic chelating compounds that sequester metal ions in solution, particularly transition metal ions. Such sequestrants include organic amino- or hydroxy-polyphosphonic acid complexing agents (either in acid or soluble salt forms), carboxylic acids (e.g., polymeric polycarboxylate), hydroxycarboxylic acids, aminocarboxylic acids, or heterocyclic carboxylic acids, e.g., pyridine-2, 6-dicarboxylic acid (dipicolinic acid).

Chelants can include sequestrants such as phosphonic acid or phosphonate salt. Suitable phosphonic acids and phosphonate salts include HEDP; ethylenediamine tetrakis methylenephosphonic acid (EDTMP); diethylenetriamine pentakis methylenephosphonic acid (DTPMP); cyclohexane-1,2-tetramethylene phosphonic acid; amino[tri(m-ethylene phosphonic acid)]; (ethylene diamine[tetra methylene-phosphonic acid)]; 2-phosphene butane-1,2,4-tricarboxylic acid; or salts thereof, such as the alkali metal salts, ammonium salts, or alkyloyl amine salts, such as mono, di, or tetra-ethanolamine salts; picolinic, dipicolinic acid or mixtures thereof. In some embodiments, organic phosphonates, e.g, HEDP are included in the compositions of the present invention. Commercially available food additive chelating agents include phosphonates sold under the trade name DEQUEST® including, for example, 1-hydroxyethylidene-1, 1-diphosphonic acid, available from Monsanto Industrial Chemicals Co., St. Louis, Mo., as DEQUEST® 2010; amino(tri(methylenephosphonic acid)), ($N[CH_2PO_3H_2]_3$), available from Monsanto as DEQUEST® 2000; ethylenediamine[tetra(methylenephosphonic acid)] available from Monsanto as DEQUEST® 2041; and 2-phosphonobutane-1,2,4-tricarboxylic acid available from Mobay Chemical Corporation, Inorganic Chemicals Division, Pittsburgh, Pa., as Bayhibit AM.

Chelants can further aminocarboxylic acid type or aminocarboxylates or derivatives. Suitable aminocarboxylic acid type sequestrants include the acids or alkali metal salts thereof, e.g., amino acetates and salts thereof. Suitable aminocarboxylates include N-hydroxyethylaminodiacetic acid; hydroxyethylenediaminetetraacetic acid, nitrilotriacetic acid (NTA); ethylenediaminetetraacetic acid (EDTA); N-hydroxyethyl-ethylenediaminetriacetic acid (HEDTA); diethylenetriaminepentaacetic acid (DTPA); and Alanine-N, N-diacetic acid; and the like; and mixtures thereof. Various biodegradable aminocarboxylate or derivative thereof are suitable for use as chelating agents, including for example, methyl glycine diacetic acid (MGDA) available as Trilon M® from BASF.

An effective amount of the anionic polymer or chelant is provided in combination with the quaternary ammonium compound to provide synergistic antimicrobial and sanitizing efficacy. Suitable concentrations of the anionic polymer or chelant in a formulation composition include from about 0.01 to about 50 wt %, or from about 0.1 to about 50 wt-%. Without being limited according to the invention, all ranges recited are inclusive of the numbers defining the range and include each integer within the defined range. In certain embodiments of the invention, the anionic polymer or chelant may be an acidic compound and therefore may be suitable for use as an acidulant and the polymer or chelant of the present invention, such as for example GLDA and HEDP.

Suitable concentrations of the anionic polymer or chelant in a use solution include between about 1 ppm and about 500 ppm, 5 ppm and about 250 ppm, 10 ppm and about 100 ppm, 20 ppm and about 100 ppm, 25 ppm and about 100 ppm, 10 ppm and about 50 ppm, 20 ppm and about 50 ppm, 25 ppm and about 50 ppm, or about 50 ppm and about 100 ppm. Without being limited according to the invention, all ranges recited are inclusive of the numbers defining the range and include each integer within the defined range.

According to embodiments of the invention, the anionic polymer or chelant may be provided in a concentrated composition in the amount between about 0.0001 wt.-%-50 wt.-%, from about 0.001 wt.-%-50 wt.-%, from about 0.01 wt.-%-50 wt.-%, from about 0.1 wt.-%-50 wt.-%, from about 0.1 wt.-%-30 wt.-%, from about 1 wt.-%-30 wt.-%, from about 0.1 wt.-%-20 wt.-%, or from about 1 wt.-%-20 wt.-%. In addition, without being limited according to the invention, all ranges recited are inclusive of the numbers defining the range and include each integer within the defined range.

Additional Optional Components

The components of the compositions can further be combined with various functional components. In some embodiments, the compositions including the quaternary ammonium compounds and anionic surfactants make up a large amount, or even substantially all of the total weight of the composition. For example, in some embodiments few or no additional functional ingredients are disposed therein. In other embodiments, additional functional ingredients may be included in the compositions. The functional ingredients provide desired properties and functionalities to the compositions. For the purpose of this application, the term "functional ingredient" includes a material that when dispersed or dissolved in the aqueous use solution provides a beneficial property in a particular use. Some particular examples of functional materials are discussed in more detail below, although the particular materials discussed are given by way of example only, and that a broad variety of other functional ingredients may be used.

In some embodiments, the compositions may include additional functional ingredients including, for example, additional surfactants, thickeners and/or viscosity modifiers, solvents, solubility modifiers, humectants, metal protecting agents, stabilizing agents, e.g., chelating agents or sequestrants, corrosion inhibitors, sequestrants and/or chelating agents, solidifying agent, sheeting agents, pH modifying components, including alkalinity and/or acidity sources, aesthetic enhancing agents (i.e., colorants, odorants, or perfumes), other cleaning agents, hydrotropes or couplers, buffers, and the like. Additionally, the compositions can be used in conjunction with one or more conventional cleaning agents, e.g., an alkaline detergent.

According to embodiments of the invention, the various additional functional ingredients may be provided in a composition in the amount from about 0 wt.-%-90 wt.-%, from about 0 wt.-%-75 wt.-%, from about 0 wt.-%-50 wt.-%, from about 0.01 wt.-%-50 wt.-%, from about 0.1 wt.-%-50 wt.-%, from about 1 wt.-%-50 wt.-%, from about 1 wt.-%-30 wt.-%, from about 1 wt.-%-25 wt.-%, or from about 1 wt.-%-20 wt.-%. In addition, without being limited according to the invention, all ranges recited are inclusive of the numbers defining the range and include each integer within the defined range. In certain preferred embodiments, the compositions of the invention do not include certain additional functional ingredients. In an aspect the compositions do not include halides. In an aspect the compositions do not include oxidants.

Alkalinity and/or Acidity Source

In some embodiments, the compositions of the present invention include an alkalinity source and/or acidulant. In a preferred embodiment, the compositions of the present invention include an acidulant. The acidulant can be effective to form a concentrate composition or a use solution with a desired acidic to neutral pH. The acidulant can be effective to form a use composition with pH of about 7, about 6 or less, about 5 or less, about 4, about 4 or less, about 3, about 3 or less, about 2, about 2 or less, or the like. In some embodiments, depending on the anionic surfactant employed in the composition, an acidulant is included in the composition. In an embodiment, an acidulant is employed in combination with linear short chain carboxylates (e.g. pH 3-5) and/or for branched/alkoxylated carboxylates having a broader pH.

In an embodiment, the acidulant includes an inorganic acid. Suitable inorganic acids include, but are not limited to, sulfuric acid, sodium bisulfate, phosphoric acid, nitric acid, and hydrochloric acid. In some embodiments, the acidulant includes an organic acid. Suitable organic acids include, but are not limited to, methane sulfonic acid, ethane sulfonic acid, propane sulfonic acid, butane sulfonic acid, xylene sulfonic acid, benzene sulfonic acid, formic acid, acetic acid, mono, di, or tri-carboxylic acids (succinic, citric), picolinic acid, dipicolinic acid, and mixtures thereof. In some embodiments, the compositions of the present invention are free or substantially free of a phosphorous based acid. In some embodiments, acidulant selected can also function as a stabilizing agent. Thus, the compositions of the present invention can be substantially free of an additional stabilizing agent.

In certain embodiments, the present composition includes about 0 to about 80 wt-% acidulant, about 0.5 wt-% to about 80 wt-% acidulant, about 0.1 to about 50 wt %, about 1 to about 50 wt %, or about 5 to about 30 wt-% acidulant. It is to be understood that all values and ranges between these values and ranges are encompassed by the compositions of the present invention.

Stabilizing Agents

In some embodiments, the compositions of the present invention include one or more stabilizing agents. In some embodiments, an acidic stabilizing agent can be used. Thus, in some embodiments, the compositions of the present invention can be substantially free of an additional acidulant. Suitable stabilizing agents include, for example, chelating agents or sequestrants. Suitable sequestrants include, but are not limited to, organic chelating compounds that sequester metal ions in solution, particularly transition metal ions. Such sequestrants include organic amino- or hydroxy-polyphosphonic acid complexing agents (either in acid or soluble salt forms), carboxylic acids (e.g., polymeric polycarboxylate), hydroxycarboxylic acids, aminocarboxylic acids, or heterocyclic carboxylic acids, e.g., pyridine-2, 6-dicarboxylic acid (dipicolinic acid).

In some embodiments, the compositions of the present invention include dipicolinic acid as a stabilizing agent. Compositions including dipicolinic acid can be formulated to be free or substantially free of phosphorous. It has also been observed that the inclusion of dipicolinic acid in a composition of the present invention aids in achieving the phase stability of the compositions, compared to other conventional stabilizing agents, e.g., 1-hydroxy ethylidene-1,1-diphosphonic acid ($CH_3C(PO_3H_2)_2OH$) (HEDP).

In other embodiments, the sequestrant can be or include phosphonic acid or phosphonate salt. Suitable phosphonic acids and phosphonate salts include HEDP; ethylenediamine tetrakis methylenephosphonic acid (EDTMP); diethylenetri-amine pentakis methylenephosphonic acid (DTPMP); cyclohexane-1,2-tetramethylene phosphonic acid; amino[tri(methylene phosphonic acid)]; (ethylene diamine[tetra methylene-phosphonic acid)]; 2-phosphene butane-1,2,4-tricarboxylic acid; or salts thereof, such as the alkali metal salts, ammonium salts, or alkyloyl amine salts, such as mono, di, or tetra-ethanolamine salts; picolinic, dipicolinic acid or mixtures thereof. In some embodiments, organic phosphonates, e.g, HEDP are included in the compositions of the present invention. Commercially available food additive chelating agents include phosphonates sold under the trade name DEQUEST® including, for example, 1-hydroxyethylidene-1, 1-diphosphonic acid, available from Monsanto Industrial Chemicals Co., St. Louis, Mo., as DEQUEST® 2010; amino(tri(methylenephosphonic acid)), ($N[CH_2PO_3H_2]_3$), available from Monsanto as DEQUEST® 2000; ethylenediamine[tetra(methylenephosphonic acid)] available from Monsanto as DEQUEST® 2041; and 2-phosphonobutane-1,2,4-tricarboxylic acid available from Mobay Chemical Corporation, Inorganic Chemicals Division, Pittsburgh, Pa., as Bayhibit AM.

The sequestrant can be or include aminocarboxylic acid type sequestrant. Suitable aminocarboxylic acid type sequestrants include the acids or alkali metal salts thereof, e.g., amino acetates and salts thereof. Suitable aminocarboxylates include N-hydroxyethylaminodiacetic acid; hydroxyethylenediaminetetraacetic acid, nitrilotriacetic acid (NTA); ethylenediaminetetraacetic acid (EDTA); N-hydroxyethyl-ethylenediaminetriacetic acid (HEDTA); diethylenetriaminepentaacetic acid (DTPA); and Alanine-N,N-diacetic acid; and the like; and mixtures thereof.

The sequestrant can be or include a polycarboxylate. Suitable polycarboxylates include, for example, polyacrylic acid, maleic/olefin copolymer, acrylic/maleic copolymer, polymethacrylic acid, acrylic acid-methacrylic acid copolymers, hydrolyzed polyacrylamide, hydrolyzed polymethacrylamide, hydrolyzed polyamide-methacrylamide copolymers, hydrolyzed polyacrylonitrile, hydrolyzed polymethacrylonitrile, hydrolyzed acrylonitrile-methacrylonitrile copolymers, polymaleic acid, polyfumaric acid, copolymers of acrylic and itaconic acid, phosphino polycarboxylate, acid or salt forms thereof, mixtures thereof, and the like.

In certain embodiments, the present composition includes about 0 to about 10 wt-% stabilizing agent, about 0.01 to about 10 wt-% stabilizing agent, about 0.4 to about 4 wt-% stabilizing agent, about 0.6 to about 3 wt-% stabilizing agent, about 1 to about 2 wt-% stabilizing agent. It is to be understood that all values and ranges within these values and ranges are encompassed by the present invention.

Wetting or Defoaming Agents

Also useful in the compositions of the invention are wetting and defoaming agents. Wetting agents function to increase the surface contact or penetration activity of the antimicrobial composition of the invention. Wetting agents which can be used in the composition of the invention include any of those constituents known within the art to raise the surface activity of the composition of the invention. In aspects of the invention various quaternary ammonium compounds are suitable for the rinse aid and sanitizing rinse aid application without the use of further defoamers in the formulation. In other embodiments employing commercially-available quaternary ammonium compounds, a defoamer is preferred in the composition or in combination with the composition, such as for example compositions employing Bardac 2250, Bardac MB50, and Bardac 205M.

Generally, defoamers which can be used in accordance with the invention preferably include alcohol alkoxylates and EO/PO block copolymers. In some embodiments, the compositions of the present invention can include antifoaming agents or defoamers which are of food grade quality given the application of the method of the invention. To this end, one of the more effective antifoaming agents includes silicones. Silicones such as dimethyl silicone, glycol polysiloxane, methylphenol polysiloxane, trialkyl or tetralkyl silanes, hydrophobic silica defoamers and mixtures thereof can all be used in defoaming applications. Commercial defoamers commonly available include silicones such as Ardefoam® from Armour Industrial Chemical Company which is a silicone bound in an organic emulsion; Foam Kill® or Kresseo® available from Krusable Chemical Company which are silicone and non-silicone type defoamers as well as silicone esters; and Anti-Foam A® and DC-200 from Dow Corning Corporation which are both food grade type silicones among others. These defoamers can be present at a concentration range from about 0.01 wt-% to 20 wt-%, 0.01 wt-% to 20 wt-%, from about 0.01 wt-% to 5 wt-%, or from about 0.01 wt-% to about 1 wt-%.

Thickening or Gelling Agents

The compositions of the present invention can include any of a variety of known thickeners. Suitable thickeners include natural gums such as xanthan gum, guar gum, or other gums from plant mucilage; polysaccharide based thickeners, such as alginates, starches, and cellulosic polymers (e.g., carboxymethyl cellulose); polyacrylates thickeners; and hydrocolloid thickeners, such as pectin. In an embodiment, the thickener does not leave contaminating residue on the surface of an object. For example, the thickeners or gelling agents can be compatible with food or other sensitive products in contact areas. Generally, the concentration of thickener employed in the present compositions or methods will be dictated by the desired viscosity within the final composition. However, as a general guideline, the viscosity enhancer or thickener within the present composition ranges from about 0.1 wt-% to about 5 wt-%, from about 0.1 wt-% to about 1.0 wt-%, or from about 0.1 wt-% to about 0.5 wt-%.

Additional Surfactants

The antimicrobial compositions and/or inactivated antimicrobial compositions according to the invention may include additional surfactants. In a particular aspect, nonionic surfactants are particularly useful for applications of use requiring additional defoaming. In some aspects, a nonionic surfactant may be desired in combination with the compositions of the invention (such as included in a detergent formulation employed in combination therewith). For example, in certain embodiments, such as food soil defoaming applications, a nonionic surfactant may be desirable to preferably include alcohol alkoxylates and EO/PO block copolymers.

Useful nonionic surfactants are generally characterized by the presence of an organic hydrophobic group and an organic hydrophilic group and are typically produced by the condensation of an organic aliphatic, alkyl aromatic or polyoxyalkylene hydrophobic compound with a hydrophilic alkaline oxide moiety which in common practice is ethylene oxide or a polyhydration product thereof, polyethylene glycol. Practically any hydrophobic compound having a hydroxyl, carboxyl, amino, or amido group with a reactive hydrogen atom can be condensed with ethylene oxide, or its polyhydration adducts, or its mixtures with alkoxylenes such as propylene oxide to form a nonionic surface-active agent. The length of the hydrophilic polyoxyalkylene moiety which is condensed with any particular hydrophobic compound can be readily adjusted to yield a water dispersible or water soluble compound having the desired degree of balance between hydrophilic and hydrophobic properties. Useful nonionic surfactants include:

Block polyoxypropylene-polyoxyethylene polymeric compounds based upon propylene glycol, ethylene glycol, glycerol, trimethylolpropane, and ethylenediamine as the initiator reactive hydrogen compound. Examples of polymeric compounds made from a sequential propoxylation and ethoxylation of initiator are commercially available under the trade names Pluronic® and Tetronic® manufactured by BASF Corp. Pluronic® compounds are difunctional (two reactive hydrogens) compounds formed by condensing ethylene oxide with a hydrophobic base formed by the addition of propylene oxide to the two hydroxyl groups of propylene glycol. This hydrophobic portion of the molecule weighs from about 1,000 to about 4,000. Ethylene oxide is then added to sandwich this hydrophobe between hydrophilic groups, controlled by length to constitute from about 10% by weight to about 80% by weight of the final molecule. Tetronic® compounds are tetra-flinctional block copolymers derived from the sequential addition of propylene oxide and ethylene oxide to ethylenediamine. The molecular weight of the propylene oxide hydrotype ranges from about 500 to about 7,000; and, the hydrophile, ethylene oxide, is added to constitute from about 10% by weight to about 80% by weight of the molecule.

Condensation products of one mole of alkyl phenol wherein the alkyl chain, of straight chain or branched chain configuration, or of single or dual alkyl constituent, contains from about 8 to about 18 carbon atoms with from about 3 to about 50 moles of ethylene oxide. The alkyl group can, for example, be represented by diisobutylene, di-amyl, polymerized propylene, iso-octyl, nonyl, and di-nonyl. These surfactants can be polyethylene, polypropylene, and polybutylene oxide condensates of alkyl phenols. Examples of commercial compounds of this chemistry are available on the market under the trade names Igepal® manufactured by Rhodiaand Triton® manufactured by Dow Chemical Company.

Condensation products of one mole of a saturated or unsaturated, straight or branched chain alcohol having from about 6 to about 24 carbon atoms with from about 3 to about 50 moles of ethylene oxide. The alcohol moiety can consist of mixtures of alcohols in the above delineated carbon range or it can consist of an alcohol having a specific number of carbon atoms within this range. Examples of like commercial surfactant are available under the trade names Neodol® manufactured by Shell Chemical Co. and Alfonic® manufactured by Sasol North America Inc.

Condensation products of one mole of saturated or unsaturated, straight or branched chain carboxylic acid having from about 8 to about 18 carbon atoms with from about 6 to about 50 moles of ethylene oxide. The acid moiety can consist of mixtures of acids in the above defined carbon atoms range or it can consist of an acid having a specific number of carbon atoms within the range.

In addition to ethoxylated carboxylic acids, commonly called polyethylene glycol esters, other alkanoic acid esters formed by reaction with glycerides, glycerin, and polyhydric (saccharide or sorbitan/sorbitol) alcohols have application in this invention for specialized embodiments, particularly indirect food additive applications. All of these ester moieties have one or more reactive hydrogen sites on their molecule which can undergo further acylation or ethylene oxide (alkoxide) addition to control the hydrophilicity of these substances. Care must be exercised when adding these fatty esters or acylated carbohydrates to compositions of the present invention containing amylase and/or lipase enzymes because of potential incompatibility.

Examples of nonionic low foaming surfactants include:

Compounds from (1) which are modified, essentially reversed, by adding ethylene oxide to ethylene glycol to provide a hydrophile of designated molecular weight; and, then adding propylene oxide to obtain hydrophobic blocks on the outside (ends) of the molecule. The hydrophobic portion of the molecule weighs from about 1,000 to about 3,100 with the central hydrophile including 10% by weight to about 80% by weight of the final molecule. These reverse Pluronics® are manufactured by BASF Corporation under the trade name Pluronic® R surfactants. Likewise, the Tetronic®R surfactants are produced by BASF Corporation by the sequential addition of ethylene oxide and propylene oxide to ethylenediamine. The hydrophobic portion of the molecule weighs from about 2,100 to about 6,700 with the central hydrophile including 10% by weight to 80% by weight of the final molecule.

Compounds from groups (1), (2), (3) and (4) which are modified by "capping" or "end blocking" the terminal hydroxy group or groups (of multi-functional moieties) to reduce foaming by reaction with a small hydrophobic molecule such as propylene oxide, butylene oxide, benzyl chloride; and, short chain fatty acids, alcohols or alkyl halides containing from 1 to about 5 carbon atoms; and mixtures thereof. Also included are reactants such as thionyl chloride which convert terminal hydroxy groups to a chloride group. Such modifications to the terminal hydroxy group may lead to all-block, block-heteric, heteric-block or all-heteric nonionics.

Additional examples of effective low foaming nonionics include:

The alkylphenoxypolyethoxyalkanols of U.S. Pat. No. 2,903,486 issued Sep. 8, 1959 to Brown et al. and represented by the formula

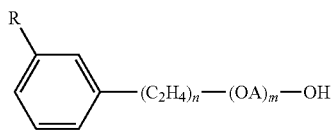

in which R is an alkyl group of 8 to 9 carbon atoms, A is an alkylene chain of 3 to 4 carbon atoms, n is an integer of 7 to 16, and m is an integer of 1 to 10.

The polyalkylene glycol condensates of U.S. Pat. No. 3,048,548 issued Aug. 7, 1962 to Martin et al. having alternating hydrophilic oxyethylene chains and hydrophobic oxypropylene chains where the weight of the terminal hydrophobic chains, the weight of the middle hydrophobic unit and the weight of the linking hydrophilic units each represent about one-third of the condensate.

The defoaming nonionic surfactants disclosed in U.S. Pat. No. 3,382,178 issued May 7, 1968 to Lissant et al. having the general formula $Z[(OR)_nOH]_z$ wherein Z is alkoxylatable material, R is a radical derived from an alkaline oxide which can be ethylene and propylene and n is an integer from, for example, 10 to 2,000 or more and z is an integer determined by the number of reactive oxyalkylatable groups.

The conjugated polyoxyalkylene compounds described in U.S. Pat. No. 2,677,700, issued May 4, 1954 to Jackson et al. corresponding to the formula $Y(C_3H_6O)_n(C_2H_4O)_mH$ wherein Y is the residue of organic compound having from about 1 to 6 carbon atoms and one reactive hydrogen atom, n has an average value of at least about 6.4, as determined by hydroxyl number and m has a value such that the oxyethylene portion constitutes about 10% to about 90% by weight of the molecule.

The conjugated polyoxyalkylene compounds described in U.S. Pat. No. 2,674,619, issued Apr. 6, 1954 to Lundsted et al. having the formula $Y[(C_3H_6On(C_2H_4O)_mH]_x$ wherein Y is the residue of an organic compound having from about 2 to 6 carbon atoms and containing x reactive hydrogen atoms in which x has a value of at least about 2, n has a value such that the molecular weight of the polyoxypropylene hydrophobic base is at least about 900 and m has value such that the oxyethylene content of the molecule is from about 10% to about 90% by weight. Compounds falling within the scope of the definition for Y include, for example, propylene glycol, glycerine, pentaerythritol, trimethylolpropane, ethylenediamine and the like. The oxypropylene chains optionally, but advantageously, contain small amounts of ethylene oxide and the oxyethylene chains also optionally, but advantageously, contain small amounts of propylene oxide.

Additional conjugated polyoxyalkylene surface-active agents which are advantageously used in the compositions of this invention correspond to the formula: $P[(C_3H_6O)_n(C_2H_4O)_mH]_x$ wherein P is the residue of an organic compound having from about 8 to 18 carbon atoms and containing x reactive hydrogen atoms in which x has a value of 1 or 2, n has a value such that the molecular weight of the polyoxyethylene portion is at least about 44 and m has a value such that the oxypropylene content of the molecule is from about 10% to about 90% by weight. In either case the oxypropylene chains may contain optionally, but advantageously, small amounts of ethylene oxide and the oxyethylene chains may contain also optionally, but advantageously, small amounts of propylene oxide.

Polyhydroxy fatty acid amide surfactants suitable for use in the present compositions include those having the structural formula $R_2CON_{R1}Z$ in which: R1 is H, $C_1$-$C_4$ hydrocarbyl, 2-hydroxy ethyl, 2-hydroxy propyl, ethoxy, propoxy group, or a mixture thereof; $R_2$ is a $C_5$-$C_{31}$ hydrocarbyl, which can be straight-chain; and Z is a polyhydroxyhydrocarbyl having a linear hydrocarbyl chain with at least 3 hydroxyls directly connected to the chain, or an alkoxylated derivative (preferably ethoxylated or propoxylated) thereof. Z can be derived from a reducing sugar in a reductive amination reaction; such as a glycityl moiety.

The alkyl ethoxylate condensation products of aliphatic alcohols with from about 0 to about 25 moles of ethylene oxide are suitable for use in the present compositions. The alkyl chain of the aliphatic alcohol can either be straight or branched, primary or secondary, and generally contains from 6 to 22 carbon atoms.

The ethoxylated $C_6$-$C_{18}$ fatty alcohols and $C_6$-$C_{18}$ mixed ethoxylated and propoxylated fatty alcohols are suitable surfactants for use in the present compositions, particularly those that are water soluble. Suitable ethoxylated fatty alcohols include the $C_6$-$C_{18}$ ethoxylated fatty alcohols with a degree of ethoxylation of from 3 to 50.

Suitable nonionic alkyl polysaccharide surfactants, particularly for use in the present compositions include those disclosed in U.S. Pat. No. 4,565,647, Llenado, issued Jan. 21, 1986. These surfactants include a hydrophobic group containing from about 6 to about 30 carbon atoms and a polysaccharide, e.g., a polyglycoside, hydrophilic group containing from about 1.3 to about 10 saccharide units. Any reducing saccharide containing 5 or 6 carbon atoms can be used, e.g., glucose, galactose and galactosyl moieties can be substituted for the glucosyl moieties. (Optionally the hydrophobic group is attached at the 2-, 3-, 4-, etc. positions thus giving a glucose or galactose as opposed to a glucoside or galactoside.) The intersaccharide bonds can be, e.g., between the one position of the additional saccharide units and the 2-, 3-, 4-, and/or 6-positions on the preceding saccharide units.

Fatty acid amide surfactants suitable for use the present compositions include those having the formula: $R_6CON(R_7)_2$ in which $R_6$ is an alkyl group containing from 7 to 21 carbon atoms and each $R_7$ is independently hydrogen, $C_1$-$C_4$ alkyl, $C_1$-$C_4$ hydroxyalkyl, or $—(C_2H_4O)_xH$, where x is in the range of from 1 to 3.

A useful class of non-ionic surfactants include the class defined as alkoxylated amines or, most particularly, alcohol alkoxylated/aminated/alkoxylated surfactants. These non-ionic surfactants may be at least in part represented by the general formulae: $R^{20}$-$(PO)_sN$-$(EO)_tH$, $R^{20}$-$(PO)_sN$-$(EO)_tH(EO)_tH$, and $R^{20}$—$N(EO)_tH$; in which $R^{20}$ is an alkyl, alkenyl or other aliphatic group, or an alkyl-aryl group of from 8 to 20, preferably 12 to 14 carbon atoms, EO is oxyethylene, PO is oxypropylene, s is 1 to 20, preferably 2-5, t is 1-10, preferably 2-5, and u is 1-10, preferably 2-5. Other variations on the scope of these compounds may be represented by the alternative formula: $R^{20}$-$(PO)_V$-$N[(EO)_wH][(EO)_zH]$ in which $R^{20}$ is as defined above, v is 1 to 20 (e.g., 1, 2, 3, or 4 (preferably 2)), and w and z are independently 1-10, preferably 2-5. These compounds are represented commercially by a line of products sold by Huntsman Chemicals as nonionic surfactants. A preferred chemical of this class includes Surfonic® PEA 25 Amine Alkoxylate. Preferred nonionic surfactants for the compositions of the invention include alcohol alkoxylates, EO/PO block copolymers, alkylphenol alkoxylates, and the like.

The treatise *Nonionic Surfactants*, edited by Schick, M. J., Vol. 1 of the Surfactant Science Series, Marcel Dekker, Inc., New York, 1983 is an excellent reference on the wide variety of nonionic compounds generally employed in the practice of the present invention. A typical listing of nonionic classes, and species of these surfactants, is given in U.S. Pat. No. 3,929,678 issued to Laughlin and Heuring on Dec. 30, 1975. Further examples are given in "Surface Active Agents and detergents" (Vol. I and II by Schwartz, Perry and Berch).

Semi-Polar Nonionic Surfactants

The semi-polar type of nonionic surface active agents are another class of nonionic surfactant useful in compositions of the present invention. Generally, semi-polar nonionics are high foamers and foam stabilizers, which can limit their application in CIP systems. However, within compositional embodiments of this invention designed for high foam cleaning methodology, semi-polar nonionics would have immediate utility. The semi-polar nonionic surfactants include the amine oxides, phosphine oxides, sulfoxides and their alkoxylated derivatives.

Amine oxides are tertiary amine oxides corresponding to the general formula:

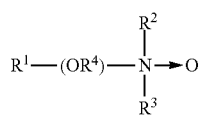

wherein the arrow is a conventional representation of a semi-polar bond; and, $R^1$, $R^2$, and $R^3$ may be aliphatic, aromatic, heterocyclic, alicyclic, or combinations thereof. Generally, for amine oxides of detergent interest, $R^1$ is an alkyl radical of from about 8 to about 24 carbon atoms; $R^2$ and $R^3$ are alkyl or hydroxyalkyl of 1-3 carbon atoms or a mixture thereof; $R^2$ and $R^3$ can be attached to each other, e.g. through an oxygen or nitrogen atom, to form a ring structure; $R^4$ is an alkaline or a hydroxyalkylene group containing 2 to 3 carbon atoms; and n ranges from 0 to about 20.

Useful water soluble amine oxide surfactants are selected from the coconut or tallow alkyl di-(lower alkyl) amine oxides, specific examples of which are dodecyldimethylamine oxide, tridecyldimethylamine oxide, etradecyldimethylamine oxide, pentadecyldimethylamine oxide, hexadecyldimethylamine oxide, heptadecyldimethylamine oxide, octadecyldimethylaine oxide, dodecyldipropylamine oxide, tetradecyldipropylamine oxide, hexadecyldipropylamine oxide, tetradecyldibutylamine oxide, octadecyldibutylamine oxide, bis(2-hydroxyethyl)dodecylamine oxide, bis(2-hydroxyethyl)-3-dodecoxy-1-hydroxypropylamine oxide, dimethyl-(2-hydroxydodecyl)amine oxide, 3,6,9-trioctadecyldimethylamine oxide and 3-dodecoxy-2-hydroxypropyldi-(2-hydroxyethyl)amine oxide.

Useful semi-polar nonionic surfactants also include the water soluble phosphine oxides having the following structure:

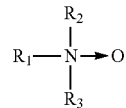

wherein the arrow is a conventional representation of a semi-polar bond; and, $R^1$ is an alkyl, alkenyl or hydroxyalkyl moiety ranging from 10 to about 24 carbon atoms in chain length; and, $R^2$ and $R^3$ are each alkyl moieties separately selected from alkyl or hydroxyalkyl groups containing 1 to 3 carbon atoms.

Examples of useful phosphine oxides include dimethyldecylphosphine oxide, dimethyltetradecylphosphine oxide, methylethyltetradecylphosphone oxide, dimethylhexadecylphosphine oxide, diethyl-2-hydroxyoctyldecylphosphine oxide, bis(2-hydroxyethyl)dodecylphosphine oxide, and bis(hydroxymethyl)tetradecylphosphine oxide.

Semi-polar nonionic surfactants useful herein also include the water soluble sulfoxide compounds which have the structure:

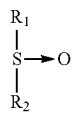

wherein the arrow is a conventional representation of a semi-polar bond; and, $R^1$ is an alkyl or hydroxyalkyl moiety of about 8 to about 28 carbon atoms, from 0 to about 5 ether linkages and from 0 to about 2 hydroxyl substituents; and $R^2$ is an alkyl moiety consisting of alkyl and hydroxyalkyl groups having 1 to 3 carbon atoms.

Useful examples of these sulfoxides include dodecyl methyl sulfoxide; 3-hydroxy tridecyl methyl sulfoxide;

3-methoxy tridecyl methyl sulfoxide; and 3-hydroxy-4-dodecoxybutyl methyl sulfoxide.

Semi-polar nonionic surfactants for the compositions of the invention include dimethyl amine oxides, such as lauryl dimethyl amine oxide, myristyl dimethyl amine oxide, cetyl dimethyl amine oxide, combinations thereof, and the like. Useful water soluble amine oxide surfactants are selected from the octyl, decyl, dodecyl, isododecyl, coconut, or tallow alkyl di-(lower alkyl) amine oxides, specific examples of which are octyldimethylamine oxide, nonyldimethylamine oxide, decyldimethylamine oxide, undecyldimethylamine oxide, dodecyldimethylamine oxide, iso-dodecyldimethyl amine oxide, tridecyldimethylamine oxide, tetradecyldimethylamine oxide, pentadecyldimethylamine oxide, hexadecyldimethylamine oxide, heptadecyldimethylamine oxide, octadecyldimethylaine oxide, dodecyldipropylamine oxide, tetradecyldipropylamine oxide, hexadecyldipropylamine oxide, tetradecyldibutylamine oxide, octadecyldibutylamine oxide, bis(2-hydroxyethyl)dodecylamine oxide, bis(2-hydroxyethyl)-3-dodecoxy-1-hydroxypropylamine oxide, dimethyl-(2-hydroxydodecyl) amine oxide, 3,6,9-trioctadecyldimethylamine oxide and 3-dodecoxy-2-hydroxypropyldi-(2-hydroxyethyl)amine oxide.

Suitable nonionic surfactants suitable for use with the compositions of the present invention include alkoxylated surfactants. Suitable alkoxylated surfactants include EO/PO copolymers, capped EO/PO copolymers, alcohol alkoxylates, capped alcohol alkoxylates, mixtures thereof, or the like. Suitable alkoxylated surfactants for use as solvents include EO/PO block copolymers, such as the Pluronic® and reverse Pluronic® surfactants; alcohol alkoxylates, such as Dehypon® LS-54 (R-$(EO)_5(PO)_4$) and Dehypon® LS-36 (R-$(EO)_3(PO)_6$); and capped alcohol alkoxylates, such as Plurafac® LF221 and Tegoten® EC 11; mixtures thereof, or the like.

Sequestrants

The composition can contain an organic or inorganic sequestrant or mixtures of sequestrants. Organic sequestrants such as sodium citrate, the alkali metal salts of nitrilotriacetic acid (NTA), dicarboxymethyl glutamic acid tetrasodium salt (GLDA), EDTA, alkali metal gluconates, polyelectrolytes such as a polyacrylic acid, and the like can be used herein. The most preferred sequestrants are organic sequestrants such as sodium gluconate due to the compatibility of the sequestrant with the formulation base.

The present invention can also incorporate sequestrants to include materials such as, complex phosphate sequestrants, including sodium tripolyphosphate, sodium hexametaphosphate, and the like, as well as mixtures thereof. Phosphates, the sodium condensed phosphate hardness sequestering agent component functions as a water softener, a cleaner, and a detergent builder. Alkali metal (M) linear and cyclic condensed phosphates commonly have a $M_2O:P_2O_5$ mole ratio of about 1:1 to 2:1 and greater. Typical polyphosphates of this kind are the preferred sodium tripolyphosphate, sodium hexametaphosphate, sodium metaphosphate as well as corresponding potassium salts of these phosphates and mixtures thereof. The particle size of the phosphate is not critical, and any finely divided or granular commercially available product can be employed.

Solidification Agents or Hardening Agents

If it is desirous to prepare compositions of the invention as a solid, a solidification agent may be included into the composition. In some embodiments, the solidification agent can form and/or maintain the composition as a solid rinse aid composition. In other embodiments, the solidification agent can solidify the composition without unacceptably detracting from the eventual release of the active ingredients. The solidification agent can include, for example, an organic or inorganic solid compound having a neutral inert character or making a functional, stabilizing or detersive contribution to the present composition. Suitable solidification agents include solid polyethylene glycol (PEG), solid polypropylene glycol, solid EO/PO block copolymer, amide, urea (also known as carbamide), nonionic surfactant (which can be employed with a coupler), anionic surfactant, starch that has been made water-soluble (e.g., through an acid or alkaline treatment process), cellulose that has been made water-soluble, inorganic agent, poly(maleic anhydride/methyl vinyl ether), polymethacrylic acid, other generally functional or inert materials with high melting points, mixtures thereof, and the like.

Suitable glycol solidification agents include a solid polyethylene glycol or a solid polypropylene glycol, which can, for example, have molecular weight of about 1,400 to about 30,000. In certain embodiments, the solidification agent includes or is solid PEG, for example PEG 1500 up to PEG 20,000. In certain embodiments, the PEG includes PEG 1450, PEG 3350, PEG 4500, PEG 8000, PEG 20,000, and the like. Suitable solid polyethylene glycols are commercially available from Union Carbide under the tradename CARBOWAX.

Suitable amide solidification agents include stearic monoethanolamide, lauric diethanolamide, stearic diethanolamide, stearic monoethanol amide, cocodiethylene amide, an alkylamide, mixtures thereof, and the like. In an embodiment, the present composition can include glycol (e.g., PEG) and amide.

Suitable inorganic solidification agents include phosphate salt (e.g., alkali metal phosphate), sulfate salt (e.g., magnesium sulfate, sodium sulfate or sodium bisulfate), acetate salt (e.g., anhydrous sodium acetate), Borates (e.g., sodium borate), Silicates (e.g., the precipitated or fumed forms (e.g., Sipernat 50® available from Degussa), carbonate salt (e.g., calcium carbonate or carbonate hydrate), other known hydratable compounds, mixtures thereof, and the like. In an embodiment, the inorganic solidification agent can include organic phosphonate compound and carbonate salt, such as an E-Form composition.

In some embodiments, the compositions of the present invention can include any agent or combination of agents that provide a requisite degree of solidification and aqueous solubility can be included in the present compositions. In other embodiments, increasing the concentration of the solidification agent in the present composition can tend to increase the hardness of the composition. In yet other embodiments, decreasing the concentration of solidification agent can tend to loosen or soften the concentrate composition.

In some embodiments, the solidification agent can include any organic or inorganic compound that imparts a solid character to and/or controls the soluble character of the present composition, for example, when placed in an aqueous environment. For example, a solidifying agent can provide controlled dispensing if it has greater aqueous solubility compared to other ingredients in the composition. Urea can be one such solidification agent. By way of further example, for systems that can benefit from less aqueous solubility or a slower rate of dissolution, an organic nonionic or amide hardening agent may be appropriate.

In some embodiments, the compositions of the present invention can include a solidification agent that provides for convenient processing or manufacture of the present composition. For example, the solidification agent can be selected to form a composition that can harden to a solid form under ambient temperatures of about 30 to about 50° C. after mixing ceases and the mixture is dispensed from the mixing system, within about 1 minute to about 3 hours, or about 2 minutes to about 2 hours, or about 5 minutes to about 1 hour.

In an exemplary aspect, a solid rinse aid may include an effective amount of a solidification agent or a hardening agent, as for example, urea which vary the solubility of the composition in an aqueous medium during use such that the rinse aid and/or other active ingredients may be dispensed from the solid composition over an extended period of time. The composition may include a hardening agent in an amount in the range of up to about 50 wt %. In other embodiments, the hardening agent may be present in amount from about 20 wt % to about 40 wt %, or in the range of about 5 to about 15 wt %.

The compositions of the present invention can include solidification agent at any effective amount. The amount of solidification agent included in the present composition can vary according to the type of composition, the ingredients of the composition, the intended use of the composition, the quantity of dispensing solution applied to the solid composition over time during use, the temperature of the dispensing solution, the hardness of the dispensing solution, the physical size of the solid composition, the concentration of the other ingredients, the concentration of the cleaning agent in the composition, and other like factors. Suitable amounts can include about 1 to about 99 wt-%, about 1.5 to about 85 wt-%, about 2 to about 80 wt-%, about 10 to about 45 wt-%, about 15% to about 40 wt-%, about 20% to about 30 wt-%, about 30% to about 70%, about 40% to about 60%, up to about 50 wt-%, about 40% to about 50%.

Additional Exemplary Embodiments

In some aspects, the antimicrobial compositions or inactivated antimicrobial compositions according to the invention may comprise, consist of and/or consist essentially of a quaternary ammonium compound in an amount from about 0.001 wt-% to about 75 wt-%, and an anionic surfactant or anionic polymer/chelant in an amount from about 0.0001 wt-% to about 50 wt-%.

In some aspects, the antimicrobial compositions or inactivated antimicrobial compositions according to the invention may comprise, consist of and/or consist essentially of a quaternary ammonium compound in an amount from about 0.001 wt-% to about 75 wt-%, an anionic surfactant or anionic polymer/chelant in an amount from about 0.0001 wt-% to about 50 wt-%, and at least one additional functional ingredient selected from the group consisting of: an acidulant in an amount from about 0.1 wt-% to about 50 wt-%, a stabilizing agent in an amount from about 0.01 wt-% to about 10 wt-%, a defoamer in an amount from about 0.01 wt-% to about 20 wt-%, a viscosity enhancer or thickener in an amount from about 0.1 wt-% to about 5 wt-%, an additional surfactant in an amount from about 0.01 wt-% to about 50 wt-%, a sequestrant in an amount from about 0.01 wt-% to about 50 wt-%, and a solidification agent in an amount from about 0.01 wt-% to about 50 wt-%.

In some aspects, the antimicrobial compositions or inactivated antimicrobial compositions according to the invention may comprise, consist of and/or consist essentially of a quaternary ammonium compound in an amount from about 0.001 wt-% to about 75 wt-%, an anionic surfactant or anionic polymer/chelant in an amount from about 0.0001 wt-% to about 50 wt-%, and at least two additional functional ingredients selected from the group consisting of: an acidulant in an amount from about 0.1 wt-% to about 50 wt-%, a stabilizing agent in an amount from about 0.01 wt-% to about 10 wt-%, a defoamer in an amount from about 0.01 wt-% to about 20 wt-%, a viscosity enhancer or thickener in an amount from about 0.1 wt-% to about 5 wt-%, an additional surfactant in an amount from about 0.01 wt-% to about 50 wt-%, a sequestrant in an amount from about 0.01 wt-% to about 50 wt-%, and a solidification agent in an amount from about 0.01 wt-% to about 50 wt-%.

In some aspects, the antimicrobial compositions or inactivated antimicrobial compositions according to the invention may comprise, consist of and/or consist essentially of a quaternary ammonium compound in an amount from about 0.001 wt-% to about 75 wt-%, an anionic surfactant or anionic polymer/chelant in an amount from about 0.0001 wt-% to about 50 wt-%, and at least three additional functional ingredients selected from the group consisting of: an acidulant in an amount from about 0.1 wt-% to about 50 wt-%, a stabilizing agent in an amount from about 0.01 wt-% to about 10 wt-%, a defoamer in an amount from about 0.01 wt-% to about 20 wt-%, a viscosity enhancer or thickener in an amount from about 0.1 wt-% to about 5 wt-%, an additional surfactant in an amount from about 0.01 wt-% to about 50 wt-%, a sequestrant in an amount from about 0.01 wt-% to about 50 wt-%, and a solidification agent in an amount from about 0.01 wt-% to about 50 wt-%.

In some aspects, the antimicrobial compositions or inactivated antimicrobial compositions according to the invention may comprise, consist of and/or consist essentially of a quaternary ammonium compound in an amount from about 0.001 wt-% to about 75 wt-%, an anionic surfactant or anionic polymer/chelant in an amount from about 0.0001 wt-% to about 50 wt-%, and at least four additional functional ingredients selected from the group consisting of: an acidulant in an amount from about 0.1 wt-% to about 50 wt-%, a stabilizing agent in an amount from about 0.01 wt-% to about 10 wt-%, a defoamer in an amount from about 0.01 wt-% to about 20 wt-%, a viscosity enhancer or thickener in an amount from about 0.1 wt-% to about 5 wt-%, an additional surfactant in an amount from about 0.01 wt-% to about 50 wt-%, a sequestrant in an amount from about 0.01 wt-% to about 50 wt-%, and a solidification agent in an amount from about 0.01 wt-% to about 50 wt-%.

In some aspects, the antimicrobial compositions or inactivated antimicrobial compositions according to the invention may comprise, consist of and/or consist essentially of a quaternary ammonium compound in an amount from about 0.001 wt-% to about 75 wt-%, an anionic surfactant or anionic polymer/chelant in an amount from about 0.0001 wt-% to about 50 wt-%, and at least five additional functional ingredients selected from the group consisting of: an acidulant in an amount from about 0.1 wt-% to about 50 wt-%, a stabilizing agent in an amount from about 0.01 wt-% to about 10 wt-%, a defoamer in an amount from about 0.01 wt-% to about 20 wt-%, a viscosity enhancer or thickener in an amount from about 0.1 wt-% to about 5 wt-%, an additional surfactant in an amount from about 0.01 wt-% to about 50 wt-%, a sequestrant in an amount from about 0.01 wt-% to about 50 wt-%, and a solidification agent in an amount from about 0.01 wt-% to about 50 wt-%.

In some aspects, the antimicrobial compositions or inactivated antimicrobial compositions according to the invention may comprise, consist of and/or consist essentially of a quaternary ammonium compound in an amount from about 0.001 wt-% to about 75 wt-%, an anionic surfactant or anionic polymer/chelant in an amount from about 0.0001 wt-% to about 50 wt-%, and at least six additional functional ingredients selected from the group consisting of: an acidulant in an amount from about 0.1 wt-% to about 50 wt-%, a stabilizing agent in an amount from about 0.01 wt-% to about 10 wt-%, a defoamer in an amount from about 0.01 wt-% to about 20 wt-%, a viscosity enhancer or thickener in an amount from about 0.1 wt-% to about 5 wt-%, an additional surfactant in an amount from about 0.01 wt-% to about 50 wt-%, a sequestrant in an amount from about 0.01 wt-% to about 50 wt-%, and a solidification agent in an amount from about 0.01 wt-% to about 50 wt-%.

In some aspects, the antimicrobial compositions or inactivated antimicrobial compositions according to the invention may comprise, consist of and/or consist essentially of a quaternary ammonium compound in an amount from about 0.001 wt-% to about 75 wt-%, an anionic surfactant or anionic polymer/chelant in an amount from about 0.0001 wt-% to about 50 wt-%, an acidulant in an amount from about 0.1 wt-% to about 50 wt-%, a stabilizing agent in an amount from about 0.01 wt-% to about 10 wt-%, a defoamer in an amount from about 0.01 wt-% to about 20 wt-%, a viscosity enhancer or thickener in an amount from about 0.1 wt-% to about 5 wt-%, an additional surfactant in an amount from about 0.01 wt-% to about 50 wt-%, a sequestrant in an amount from about 0.01 wt-% to about 50 wt-%, and a solidification agent in an amount from about 0.01 wt-% to about 50 wt-%.

In some aspects, the antimicrobial compositions or inactivated antimicrobial compositions according to the invention may comprise, consist of and/or consist essentially of a quaternary ammonium compound in an amount from about 0.001 wt-% to about 75 wt-%, an anionic surfactant or anionic polymer/chelant in an amount from about 0.0001 wt-% to about 50 wt-%, and at least one additional functional ingredient selected from the group consisting of: additional surfactants, thickeners and/or viscosity modifiers, solvents, solubility modifiers, humectants, metal protecting agents, corrosion inhibitors, sequestrants and/or chelating agents, solidifying agent, sheeting agents, pH modifying components, including alkalinity and/or acidity sources, aesthetic enhancing agents (i.e., colorants, odorants, or perfumes), other cleaning agents, hydrotropes or couplers, buffers, and the like in an amount from about 0.01 wt-% to about 50 wt-%.

In some aspects, the antimicrobial compositions or inactivated antimicrobial compositions according to the invention may comprise, consist of and/or consist essentially of a quaternary ammonium compound in an amount from about 0.001 wt-% to about 75 wt-%, an anionic surfactant or anionic polymer/chelant in an amount from about 0.0001 wt-% to about 50 wt-%, and at least two additional functional ingredients selected from the group consisting of: additional surfactants, thickeners and/or viscosity modifiers, solvents, solubility modifiers, humectants, metal protecting agents, corrosion inhibitors, sequestrants and/or chelating agents, solidifying agent, sheeting agents, pH modifying components, including alkalinity and/or acidity sources, aesthetic enhancing agents (i.e., colorants, odorants, or perfumes), other cleaning agents, hydrotropes or couplers, buffers, and the like in an amount from about 0.01 wt-% to about 50 wt-%.

In some aspects, the antimicrobial compositions or inactivated antimicrobial compositions according to the invention may comprise, consist of and/or consist essentially of a quaternary ammonium compound in an amount from about 0.001 wt-% to about 75 wt-%, an anionic surfactant or anionic polymer/chelant in an amount from about 0.0001 wt-% to about 50 wt-%, and at least three additional functional ingredients selected from the group consisting of: additional surfactants, thickeners and/or viscosity modifiers, solvents, solubility modifiers, humectants, metal protecting agents, corrosion inhibitors, sequestrants and/or chelating agents, solidifying agent, sheeting agents, pH modifying components, including alkalinity and/or acidity sources, aesthetic enhancing agents (i.e., colorants, odorants, or perfumes), other cleaning agents, hydrotropes or couplers, buffers, and the like in an amount from about 0.01 wt-% to about 50 wt-%.

In some aspects, the antimicrobial compositions or inactivated antimicrobial compositions according to the invention may comprise, consist of and/or consist essentially of a quaternary ammonium compound in an amount from about 0.001 wt-% to about 75 wt-%, an anionic surfactant or anionic polymer/chelant in an amount from about 0.0001 wt-% to about 50 wt-%, and at least four additional functional ingredients selected from the group consisting of: additional surfactants, thickeners and/or viscosity modifiers, solvents, solubility modifiers, humectants, metal protecting agents, corrosion inhibitors, sequestrants and/or chelating agents, solidifying agent, sheeting agents, pH modifying components, including alkalinity and/or acidity sources, aesthetic enhancing agents (i.e., colorants, odorants, or perfumes), other cleaning agents, hydrotropes or couplers, buffers, and the like in an amount from about 0.01 wt-% to about 50 wt-%.

In some aspects, the antimicrobial compositions or inactivated antimicrobial compositions according to the invention may comprise, consist of and/or consist essentially of a quaternary ammonium compound in an amount from about 0.001 wt-% to about 75 wt-%, an anionic surfactant or anionic polymer/chelant in an amount from about 0.0001 wt-% to about 50 wt-%, and at least five additional functional ingredients selected from the group consisting of: additional surfactants, thickeners and/or viscosity modifiers, solvents, solubility modifiers, humectants, metal protecting agents, corrosion inhibitors, sequestrants and/or chelating agents, solidifying agent, sheeting agents, pH modifying components, including alkalinity and/or acidity sources, aesthetic enhancing agents (i.e., colorants, odorants, or perfumes), other cleaning agents, hydrotropes or couplers, buffers, and the like in an amount from about 0.01 wt-% to about 50 wt-%.

Solubilizing Fatty Acids

A method of solubilizing a fatty acid is included. In an exemplary application, solubilizing a fatty acid is particularly useful for the solubilization and therefore removal of a fatty acid soil (cohesive energy). The method includes providing a carboxylic fatty acid and solubilizing it with a quaternary ammonium. Such method results in a composition having heightened antimicrobial activities. In an embodiment a mole:mole ratio of fatty acid to quaternary ammonium compound is used to solubilize the fatty acid. In a further embodiment, the solubilizing of a fatty acid includes approximately a mole to mole ratio of quaternary ammonium compound and fatty acid. In other aspects, the compositions include up to about a 10 to about a 1 molar ratio of quaternary ammonium compound and fatty acid. In other aspects, the compositions include up to about 1 to about a 10 molar ratio of quaternary ammonium compound and fatty acid, or any combination thereof. In another embodiment the compositions are provided with a molar ratio of fatty acid to quaternary ammonium of about 1 mole fatty acid to about 1 mole of quaternary ammonium compound. In another embodiment the composition is provided with a molar ratio of fatty acid to quaternary ammonium compound of about 1.5 mole fatty acid to about 1 mole of quaternary ammonium compound. In another embodiment the composition is provided with a molar ratio of fatty acid to quaternary ammonium compound of about 1 mole fatty acid to about 10 moles of quaternary ammonium compound. In another embodiment the composition is provided with a molar ratio of fatty acid to quaternary ammonium compound of about 2 moles fatty acid to about 1 mole of quaternary ammonium compound.

Without being limited to a particular mechanism of action, when it is said that the fatty acid is solubilized it is meant that the combination including the fatty acid is soluble in water. A composition is said to be "water soluble" if it is at least 90 percent soluble in water, at least 95 percent soluble in water, at least 98 percent soluble in water, at least 99 percent soluble in water, and at least 99.9 percent soluble in water.

Use Compositions

The activated antimicrobial compositions and inactivated compositions of the present invention may include concentrate compositions and use compositions, or may be diluted to form use compositions. For example, a concentrate composition can be diluted, for example with water, to form a use composition. In general, a concentrate refers to a composition that is intended to be diluted, such as with water to provide a use solution that contacts a surface and/or product in need of treatment to provide the desired surface activity. The antimicrobial compositions or inactivated antimicrobial compositions that contact the surface and/or product in need of treatment can be referred to as a concentrate or a use composition (or use solution) dependent upon the formulation employed in methods according to the invention. It should be understood that the concentration of the quaternary ammonium compound and anionic surfactants in the composition will vary depending on whether the composition is provided as a concentrate or as a use solution. In an embodiment, a concentrate composition can be diluted to a use solution before applying to an object. The concentrate can be marketed and an end user can dilute the concentrate with water or an aqueous diluent to a use solution.

Compositions of the invention can be formulated and sold for use as is, or as solvent concentrates. If desired, such concentrates can be used full-strength as antimicrobial agents. However, the concentrates typically will be diluted with a fluid (e.g., water) that subsequently forms the dilute phase or a use solution. Preferably, the concentrate forms a single phase before such dilution and remains so while stored in the container in which it will be sold. When combined with water or other desired diluting fluid at an appropriate dilution level and subjected to mild agitation (e.g., by stirring or pumping the composition), some compositions of the invention will form a pseudo-stable dispersion, and other compositions of the invention will form a clear or quasi-stable solution or dispersion. If a pseudo-stable composition is formed, then the composition preferably remains in the pseudo-stable state for a sufficiently long period so that the composition can be applied to a surface before the onset of phase separation. The pseudo-stable state need only last for a few seconds when suitably rapid application techniques such as spraying are employed, or when agitation during application is employed. The pseudo-stable state desirably lasts for at least one minute or more after mixing and while the composition is stored in a suitable vessel, and preferably lasts for five minutes or more after mixing. Often normal refilling or replenishment of the applicator (e.g., by dipping the applicator in the composition) will provide sufficient agitation to preserve the pseudo-stable state of the composition during application.

A use solution may be prepared from the concentrate by diluting the concentrate with water at a dilution ratio that provides a use solution having desired sanitizing and/or other antimicrobial properties. The water that is used to dilute the concentrate to form the use composition can be referred to as water of dilution or a diluent, and can vary from one location to another. The typical dilution factor is between approximately 1 and approximately 10,000 but will depend on factors including water hardness, the amount of soil to be removed and the like. In an embodiment, the concentrate is diluted at a ratio of between about 1:10 and about 1:10,000 concentrate to water. Particularly, the concentrate is diluted at a ratio of between about 1:100 and about 1:5,000 concentrate to water. More particularly, the concentrate is diluted at a ratio of between about 1:250 and about 1:2,000 concentrate to water.

In preferred embodiments the present invention includes concentrate compositions and use compositions. In an embodiment, a concentrate composition can be diluted to a use solution before applying to an object. The concentrate can be marketed and an end user can dilute the concentrate with water or an aqueous diluent to a use solution. The level of active components in the concentrate composition is dependent on the intended dilution factor and the desired activity of the antimicrobial composition. Generally, a dilution of about 1 fluid ounce to about 10 gallons of water to about 10 fluid ounces to about 1 gallon of water is used for aqueous compositions of the present invention. In some embodiments, higher use dilutions can be employed if elevated use temperature (greater than 25° C.) or extended exposure time (greater than 30 seconds) can be employed. In the typical use locus, the concentrate is diluted with a major proportion of water using commonly available tap or service water mixing the materials at a dilution ratio of about 3 to about 40 ounces of concentrate per 100 gallons of water.

In some embodiments, the concentrated compositions can be diluted at a dilution ratio of about 0.1 g/L to about 100 g/L concentrate to diluent, about 0.5 g/L to about 10.0 g/L concentrate to diluent, about 1.0 g/L to about 4.0 g/L concentrate to diluent, or about 1.0 g/L to about 2.0 g/L concentrate to diluent.

In other embodiments, a use composition can include about 0.01 to about 10 wt-% of a concentrate composition and about 90 to about 99.99 wt-% diluent; or about 0.1 to about 1 wt-% of a concentrate composition and about 99 to about 99.9 wt-% diluent.

Amounts of an ingredient in a use composition can be calculated from the amounts listed above for concentrate compositions and these dilution factors. In some embodiments, the concentrated compositions of the present invention are diluted such that the quaternary ammonium component is present at from about 10 ppm to about 100 ppm, or about 50 ppm to about 400 ppm. In other embodiments, the concentrated compositions of the present invention are diluted such that the quaternary ammonium component is present at about 20 ppm or more, about 40 ppm or more, about 60 ppm or more, about 80 ppm or more, about 100 ppm or more, about 500 ppm, about 1000 ppm, or about 10,000 to about 20,000 ppm. It is to be understood that all values and ranges between these values and ranges are encompassed by the present invention.

A variety of fluids can be used as the diluting solvent, including water in its liquid form; steam; condensed gases and other supercritical fluids (e.g., $CO_2$); perchloroethylene;

oils such as silicone oils (e.g., siloxanes), gear oils, transaxle oils, mineral oils or vegetable oils; and carboxylic esters such as methyl soyate. Mixtures of diluting solvents can be used if desired. Preferably, the diluting solvent consists essentially of or consists of water in its liquid form. The remainder of this specification will primarily discuss the use of water in its liquid form as the diluting solvent, it being understood that other suitable fluids could be added to or substituted for water in its liquid form if desired.

In an embodiment of the invention, the concentrated compositions and use compositions maintain their sanitizing efficacy while being tolerant to water conditions, or are independent of water conditions such as water hardness. According to embodiments of the invention, compositions are tolerant of water conditions of about 0 parts per million (ppm) to about 500 ppm (about 0 to about 30 grains per gallon) water hardness without impacting sanitizing efficacy according to embodiments of the invention. As referred to herein, the ppm of water hardness refers to ppm of calcium, magnesium and other metals which may be found in the water and contributing to the hardness level.

Manufacturing Methods

Compositions of the invention are prepared by addition of materials. The anionic surfactant is added to the quaternary ammonium. The quaternary ammonium compound readily couples the more hydrophobic organic acid into solution with minimal or no agitation.

In an aspect, the addition of materials is provided in a mole to mole ratio of quaternary ammonium and anionic surfactant up to about a 10:about 1 molar ratio. In an embodiment the ratio of quaternary ammonium to anionic surfactant is about mole to mole.

In some aspects, the compositions according to the invention can be made by combining the components in an aqueous diluent using commonly available containers and blending apparatus. Beneficially, no special manufacturing equipment is required for making the compositions employing the quaternary ammonium compounds and the anionic surfactants. A preferred method for manufacturing the cleaning composition of the invention includes introducing the components into a stirred production vessel.

The antimicrobial compositions and/or inactivated antimicrobial compositions according to the invention can be provided in single use or multiple use compositions. In a preferred aspect, the composition is a concentrated liquid or solid composition. Various solids can be employed according to the invention and without limiting the scope of the invention. It should be understood that compositions and methods embodying the invention are suitable for preparing a variety of solid compositions, as for example, a cast, extruded, pressed, molded or formed solid pellet, block, tablet, and the like. In some embodiments, the solid composition can be formed to have a weight of 50 grams or less, while in other embodiments, the solid composition can be formed to have a weight of 50 grams or greater, 500 grams or greater, or 1 kilogram or greater.

Methods Employing Antimicrobial Compositions of the Invention

The present invention includes methods of using the antimicrobial compositions of the present invention for various applications. The invention includes a method for reducing a microbial population, a method for reducing the population of a microorganism on skin and a method for treating a disease of skin. These methods can operate on an article, surface, in a body or stream of water or a gas, or the like, by contacting the article, surface, body, or stream with a composition of the invention. Contacting can include any of numerous methods for applying a composition of the invention, such as spraying the compositions, immersing the article in compositions, foam or gel treating the article with the compounds or composition, or a combination thereof.

In some embodiments, the compositions of the present invention include killing one or more of the pathogenic bacteria associated with health care surfaces and environments including, but not limited to, *Salmonella typhimurium*, *Staphylococcus aureus*, methicillin resistant *Staphylococcus aureus*, *Salmonella choleraesuris*, *Pseudomonas aeruginosa*, *Escherichia coli*, mycobacteria, yeast, and mold. The compositions of the invention have activity against a wide variety of microorganisms such as Gram positive (for example, *Listeria monocytogenes* or *Staphylococcus aureus*) and Gram negative (for example, *Escherichia coli* or *Pseudomonas aeruginosa*) bacteria, yeast, molds, bacterial spores, viruses, etc. The compounds and compositions of the present invention, as described above, have activity against a wide variety of human pathogens. The present compounds and compositions can kill a wide variety of microorganisms on a food processing surface, on the surface of a food product, in water used for washing or processing of food product, on a health care surface, or in a health care environment.

The present methods can be used to achieve any suitable reduction of the microbial population in and/or on the target or the treated target composition. In some embodiments, the present methods can be used to reduce the microbial population in and/or on the target or the treated target composition by at least one log 10. In other embodiments, the present methods can be used to reduce the microbial population in and/or on the target or the treated target composition by at least two log 10. In still other embodiments, the present methods can be used to reduce the microbial population in and/or on the target or the treated target composition by at least three log 10. In still other embodiments, the present methods can be used to reduce the microbial population in and/or on the target or the treated target composition by at least five log 10. Without limiting the scope of invention, the numeric ranges are inclusive of the numbers defining the range and include each integer within the defined range.

The compositions of the invention can be used for a variety of domestic or industrial applications, e.g., to reduce microbial or viral populations on a surface or object or in a body or stream of water. The compounds can be applied in a variety of areas including kitchens, bathrooms, factories, hospitals, dental offices and food plants, and can be applied to a variety of hard or soft surfaces having smooth, irregular or porous topography. Suitable hard surfaces include, for example, architectural surfaces (e.g., floors, walls, windows, sinks, tables, counters and signs); eating utensils; hard-surface medical or surgical instruments and devices; and hard-surface packaging. Such hard surfaces can be made from a variety of materials including, for example, ceramic, metal, glass, wood or hard plastic. Suitable soft surfaces include, for example paper; filter media; hospital and surgical linens and garments; soft-surface medical or surgical instruments and devices; and soft-surface packaging. Such soft surfaces can be made from a variety of materials including, for example, paper, fiber, woven or nonwoven fabric, soft plastics and elastomers. The compositions of the invention can also be applied to soft surfaces such as food and skin (e.g., a hand). The present compounds can be employed as a foaming or non-foaming environmental sanitizer or disinfectant.

The compositions of the invention can be included in products such as sterilants, sanitizers, disinfectants, preservatives, deodorizers, antiseptics, fungicides, germicides, sporicides, virucides, detergents, bleaches, hard surface cleaners, hand soaps, waterless hand sanitizers, lubricants, rinse aids, 2-in-1 and/or 3-in-1 products, such as insecticide/cleaner/sanitizer, 3-sink applications, and pre- or post-surgical scrubs.

The compositions can also be used in veterinary products such as mammalian skin treatments or in products for sanitizing or disinfecting animal enclosures, pens, watering stations, and veterinary treatment areas such as inspection tables and operation rooms. The present compositions can be employed in an antimicrobial foot bath for livestock or people.

In some aspects, the compositions of the present invention can be employed for reducing the population of pathogenic microorganisms, such as pathogens of humans, animals, and the like. The compounds exhibit activity against pathogens including fungi, molds, bacteria, spores, and viruses, for example, *S. aureus, E. coli, Streptococci, Legionella, Pseudomonas aeruginosa*, mycobacteria, tuberculosis, phages, or the like. Such pathogens can cause a variety of diseases and disorders, including mastitis or other mammalian milking diseases, tuberculosis, and the like. Compositions of the present invention can reduce the population of microorganisms on skin or other external or mucosal surfaces of an animal. In addition, the present compounds can kill pathogenic microorganisms that spread through transfer by water, air, or a surface substrate. The compositions need only be applied to the skin, other external or mucosal surfaces of an animal water, air, or surface.

The antimicrobial compositions can also be used on foods and plant species to reduce surface microbial populations; used at manufacturing or processing sites handling such foods and plant species; or used to treat process waters around such sites. For example, the compounds can be used on food transport lines (e.g., as belt sprays); boot and hand-wash dip-pans; food storage facilities; anti-spoilage air circulation systems; refrigeration and cooler equipment; beverage chillers and warmers, blanchers, cutting boards, third sink areas, and meat chillers or scalding devices. The compositions of the invention can be used to treat produce transport waters such as those found in flumes, pipe transports, cutters, slicers, blanchers, retort systems, washers, and the like. Particular foodstuffs that can be treated with compounds of the invention include eggs, meats, seeds, leaves, fruits and vegetables. Particular plant surfaces include both harvested and growing leaves, roots, seeds, skins or shells, stems, stalks, tubers, corms, fruit, and the like.

In some aspects, the compositions of the present invention are useful in the cleaning or sanitizing of containers, processing facilities, or equipment in the food service or food processing industries. The compositions have particular value for use on food packaging materials and equipment, and especially for cold or hot aseptic packaging. Examples of process facilities in which the compound of the invention can be employed include a milk line dairy, a continuous brewing system, food processing lines such as pumpable food systems and beverage lines, etc. Food service wares can be disinfected with the compound of the invention. For example, the compounds can also be used on or in ware wash machines, low temperature ware wash machines, dishware, bottle washers, bottle chillers, warmers, third sink washers, cutting areas (e.g., water knives, slicers, cutters and saws) and egg washers. Particular treatable surfaces include packaging such as cartons, bottles, films and resins; dish ware such as glasses, plates, utensils, pots and pans; ware wash and low temperature ware wash machines; exposed food preparation area surfaces such as sinks, counters, tables, floors and walls; processing equipment such as tanks, vats, lines, pumps and hoses (e.g., dairy processing equipment for processing milk, cheese, ice cream and other dairy products); and transportation vehicles. Containers include glass bottles, PVC or polyolefin film sacks, cans, polyester, PEN or PET bottles of various volumes (100 ml to 2 liters, etc.), one gallon milk containers, paper board juice or milk containers, etc.

Compositions of the present invention can also be employed by dipping food processing equipment into the use solution, soaking the equipment for a time sufficient to sanitize the equipment, and wiping or draining excess solution off the equipment, The compound may be further employed by spraying or wiping food processing surfaces with the use solution, keeping the surfaces wet for a time sufficient to sanitize the surfaces, and removing excess solution by wiping, draining vertically, vacuuming, etc.

Compositions of the present invention may also be used in a method of sanitizing hard surfaces such as institutional type equipment, utensils, dishes, health care equipment or tools, instruments and other hard surfaces.

The antimicrobial compositions can be applied to microbes or to soiled or cleaned surfaces using a variety of methods. These methods can operate on an object, surface, in a body or stream of water or a gas, or the like, by contacting the object, surface, body, or stream with a compound of the invention. Contacting can include any of numerous methods for applying a compound, such as spraying the compound, immersing the object in the compound, foam or gel treating the object with the compound, or a combination thereof.

A concentrate or use concentration of a compound of the present invention can be applied to or brought into contact with an object by any conventional method or apparatus for applying an antimicrobial or cleaning compound to an object. For example, the object can be wiped with, sprayed with, foamed on, and/or immersed in the compound, or a use solution made from the composition. The composition can be sprayed, foamed, or wiped onto a surface; the composition can be caused to flow over the surface, or the surface can be dipped into the composition. Contacting can be manual or by machine. Food processing surfaces, food products, food processing or transport waters, and the like can be treated with liquid, foam, gel, aerosol, gas, wax, solid, or powdered stabilized compounds according to the invention, or solutions containing these compounds.

The various methods of treatment according to the invention can include the use of any suitable level of the quaternary ammonium compound and anionic surfactant. In some embodiments, the treated target composition comprises from about 1 ppm to about 1000 ppm of the quaternary ammonium compound when diluted for use. In further embodiments, the treated target composition comprises from about 1 ppm and about 500 ppm, 5 ppm and about 400 ppm, 10 ppm and about 100 ppm, 20 ppm and about 100 ppm, 25 ppm and about 100 ppm, 10 ppm and about 75 ppm, 20 ppm and about 75 ppm, 25 ppm and about 75 ppm, or about 50 ppm of the quaternary ammonium compound when diluted for use. In some embodiments, the treated target composition comprises from about 1 ppm to about 1000 ppm of the anionic surfactant in a use solution. In further embodiments, the treated target composition comprises from about 1 ppm and about 500 ppm, 5 ppm and about 250 ppm, 10 ppm and about 100 ppm, 20 ppm and about 100 ppm, 25 ppm and about 100 ppm, 10 ppm and about 50 ppm, 20 ppm and about 50 ppm, 25 ppm and about 50 ppm, or about 50 ppm and about 100 ppm of the anionic surfactant when diluted for use.

In an aspect, the methods of the invention include generating a use solution from the concentrated solid or liquid compositions of the invention. A use solution may be prepared from the concentrate by diluting the concentrate with water at a dilution ratio that provides a use solution having desired sanitizing and/or other antimicrobial properties. The water that is used to dilute the concentrate to form the use composition can be referred to as water of dilution or a diluent, and can vary from one location to another. The typical dilution factor is between approximately 1 and approximately 10,000. In an embodiment, the concentrate is diluted at a ratio of between about 1:10 and about 1:10,000 concentrate to water. Particularly, the concentrate is diluted at a ratio of between about 1:100 and about 1:5,000 concentrate to water. More particularly, the concentrate is diluted at a ratio of between about 1:250 and about 1:2,000 concentrate to water.

In an aspect, a concentrated antimicrobial composition is diluted to use solution concentration of about 0.001% (wt/vol.) to about 10% (wt/vol.), or from about 0.001% (wt/vol.) to about 5% (wt/vol.), or from about 0.001% (wt/vol.) to about 2% (wt/vol.), or from about 0.01% (wt/vol.) to about 1% (wt/vol.). Without limiting the scope of invention, the numeric ranges are inclusive of the numbers defining the range and include each integer within the defined range.

Compositions of the invention can be formulated and sold for use as is, or as solvent or solid concentrates. If desired, such concentrates can be used full-strength as sanitizing rinse compositions. However, the concentrates typically will be diluted with a fluid (e.g., water) that subsequently forms the dilute phase or a use solution. Preferably, the concentrate forms a single phase before such dilution and remains so while stored in the container in which it will be sold. When combined with water or other desired diluting fluid at an appropriate dilution level and subjected to mild agitation (e.g., by stirring or pumping the composition), some compositions of the invention will form a pseudo-stable dispersion, and other compositions of the invention will form a clear or quasi-stable solution or dispersion. If a pseudo-stable composition is formed, then the composition preferably remains in the pseudo-stable state for a sufficiently long period so that the composition can be applied to a surface before the onset of phase separation. The pseudo-stable state need only last for a few seconds when suitably rapid application techniques such as spraying are employed, or when agitation during application is employed. The pseudo-stable state desirably lasts for at least one minute or more after mixing and while the composition is stored in a suitable vessel, and preferably lasts for five minutes or more after mixing. Often normal refilling or replenishment of the applicator (e.g., by dipping the applicator in the composition) will provide sufficient agitation to preserve the pseudo-stable state of the composition during application.

The various applications of use described herein provide the quaternary ammonium compound and anionic surfactant compositions to a surface and/or water source. Beneficially, the compositions of the invention are fast-acting. However, the present methods require a certain minimal contact time of the compositions with the surface or product in need of treatment for occurrence of sufficient antimicrobial effect. The contact time can vary with concentration of the use compositions, method of applying the use compositions, temperature of the use compositions, pH of the use compositions, amount of the surface or product to be treated, amount of soil or substrates on/in the surface or product to be treated, or the like. The contact or exposure time can be about 15 seconds, at least about 15 seconds, about 30 seconds or greater than 30 seconds. In some embodiments, the exposure time is about 1 to 5 minutes. In other embodiments, the exposure time is a few minutes to hours. In other embodiments, the exposure time is a few hours to days. The contact time will further vary based upon the use concentration of actives of compositions according to the invention.

Scale/Mineral Removal

The activated quaternary ammonium compound and anionic surfactant (or polymer/chelant) compositions of the invention are further suitable for use in various applications and methods in need of treating or preventing scaling, including hard water/mineral scale control on surfaces. In a preferred embodiment, the anionic polymer or chelant provides a surface active material suitable for concentrating at an interface to provide beneficial scale mineral removal. In addition, the methods of the invention are well suited for controlling water hardness buildup on a plurality of surfaces. The methods of the invention prevent moderate to heavy accumulation of hardness and/or the redeposition of soils on treated substrate surfaces which beneficially improving the aesthetic appearance of the surface. In certain embodiments, surfaces in need of hard water scale accumulation prevention, include for example, plastics, metal and/or glass surfaces.

In a beneficial aspect of the invention, the methods of the invention reduce the formation, precipitation and/or deposition of hard water scale, such as calcium carbonate, on hard surfaces contacted by the activated compositions. In an embodiment, the activated compositions are employed for the prevention of formation, precipitation and/or deposition of hard water scale on articles such as glasses, plates, silverware, etc. The activated compositions are effective at removing and/or preventing hard water scale accumulation and/or preventing the redeposition of soils in various applications, such as warewashing applications, using a variety of water sources, including hard water. In addition, the activated compositions are suitable for use at temperature ranges typically used in industrial warewashing applications, including for example from about 150° F. to about 165° F. during washing steps and from about 170° F. to about 185° F. during rinsing steps.

In addition, the methods of use of the activated compositions according to the present invention are also suitable for CIP and/or COP processes to replace the use of bulk detergents leaving hard water residues on treated surfaces. The methods of use may be desirable in additional applications where industrial standards are focused on the quality of the treated surface, such that the prevention of hard water scale accumulation provided by the activated compositions of the invention are desirable. Such applications may include, but are not limited to, vehicle care, industrial, hospital and textile care.

Additional examples of applications of use for the activated compositions include, for example, alkaline detergents effective as grill and oven cleaners, ware wash detergents, laundry detergents, laundry presoaks, drain cleaners, hard surface cleaners, surgical instrument cleaners, transportation vehicle cleaning, vehicle cleaners, dish wash presoaks, dish wash detergents, beverage machine cleaners, concrete cleaners, building exterior cleaners, metal cleaners, floor finish strippers, degreasers and burned-on soil removers. In a variety of these applications, cleaning compositions having a very high alkalinity are most desirable and efficacious; however, the damage caused by hard water scale accumulation is undesirable.

In general, the various applications of use can be employed by dipping, spraying, submerging or otherwise contacting the surface with a use solution for a time sufficient, including from a few seconds to a few minutes, or longer. The methods may further include wiping or draining excess solution from the surface.

Destaining

The activated quaternary ammonium compound and anionic surfactant (or polymer/chelant) compositions of the invention are further suitable for use in various applications and methods in need of destaining. In general, the compositions can be used for destaining by dipping, spraying, submerging or otherwise contacting the surface with a use solution for a time sufficient, including from a few seconds to a few minutes, or longer and wiping or draining excess solution off the equipment. The compositions of the present invention may be further employed by spraying or wiping food processing surfaces with the use solution, keeping the surfaces wet for a time sufficient to sanitize the surfaces, and removing excess solution by wiping, draining vertically, vacuuming, etc.

The activate compositions obtained according to the present invention may also be used in a method of destaining various hard surfaces such as institutional type equipment, utensils, dishes, health care equipment or tools, and other hard surfaces.

Laundry Applications

In some aspects, the compounds and compositions can also be employed in sanitizing articles, e.g., textiles, which have become contaminated. In further aspects, the compounds and compositions can also be employed in cleaning and disinfecting articles, e.g., textiles. The articles are contacted with the compounds of the invention at use temperatures in the range of about 4° C. to 80° C., for a period of time effective to sanitize, disinfect, and/or sterilize the articles. In some embodiments, the compositions of the present invention can be used to sanitize articles at a temperature of about 30° C. to about 50° C. or about 40° C. For example, in some embodiments, the compositions of the present invention can be injected into the wash or rinse water of a laundry machine and contacted with contaminated fabric for a time sufficient to sanitize the fabric. In some embodiments, the contaminated fabric is contacted with the compounds and compositions of the present invention for about 5 to about 30 minutes. Excess solution can then be removed by rinsing or centrifuging the fabric.

The compositions of the present invention can be used alone to treat the articles, e.g., textiles, or can be used in conjunction with conventional detergents suitable for the articles to be treated. The compositions of the invention can be used with conventional detergents in a variety of ways, for example, the compositions of the invention can be formulated with a conventional detergent. In other embodiments, the compositions of the invention can be used to treat the article as a separate additive from a conventional detergent. When used as a separate additive, the compounds and compositions of the present invention can contact the article to be treated at any time. For example, the compositions of the invention can contact the article before, after, or substantially simultaneously as the articles are contacted with the selected detergent.

In some embodiments, when used as a sanitizing/disinfecting agent for a laundry application, compounds of the present invention will be present in a composition at about 5 ppm to about 1000 ppm. In other embodiments, when used as a sanitizing/disinfecting agent for a laundry application, a compound or mixture of compounds of the present invention will be present in a composition at about 25 ppm to about 100 ppm. In other embodiments, when used as a sanitizing/disinfecting agent in a laundry application, a compound or mixture thereof of the present invention will be present at about 20, about 40, about 60, or about 80 ppm.

Methods Employing Inactivated Antimicrobial Compositions of the Invention

Water Treatment Applications

The inactivated compositions can be used for a variety of purposes, including for example treating water sources and water treatment applications. In various applications, water sources and waste sources contain residual antimicrobial agents, including quaternary ammonium compounds.

In an embodiment, the inactivated compositions can be utilized for water treatment methods connected to a water main of a house or business. The inactivated compositions can be employed in line before the hot water heater, or after the hot water heater. In other aspects, the present invention provides inactivated compositions for use in a cleaning process.

In other embodiments once the water has been treated, the treated water is provided to an automatic washing machine, e.g., an automatic ware washing or dishwashing machine, a vehicle washing system, an instrument washer, a clean in place system, a food processing cleaning system, a bottle washer, and an automatic laundry washing machine, from the treated water delivery line of the apparatus. Alternatively, the treated water may be used in a manual washing system. Any automatic or manual washing machine that would benefit from the use of water treated in accordance with the methods of the present invention can be used. The treated water is then combined with a detersive composition in the washing machine to provide a use composition. Any detersive composition can be used in the system of the present invention, for example, a cleaning composition, a rinse agent composition or a drying agent composition. The articles to be cleaned are then contacted with the use solution in the automatic washing machine such that they are cleaned.

The water treatment methods and systems of the present invention can be used in a variety of industrial and domestic applications. The water treatment methods and systems can be employed in a residential setting or in a commercial setting, e.g., in a restaurant, hotel, hospital. For example, a water treatment method, system, or apparatus of the present invention can be used in: ware washing applications, e.g., washing eating and cooking utensils and other hard surfaces such as showers, sinks, toilets, bathtubs, countertops, windows, mirrors, and floors; in laundry applications, e.g., to treat water used in an automatic textile washing machine at the pre-treatment, washing, souring, softening, and/or rinsing stages; in vehicle care applications, e.g., to treat water used for pre-rinsing, e.g., an alkaline presoak and/or low pH presoak, washing, polishing, and rinsing a vehicle; industrial applications, e.g., cooling towers, boilers, industrial equipment including heat exchangers; in food service applications, e.g., to treat water lines for coffee and tea brewers, espresso machines, ice machines, pasta cookers, water heaters, steamers and/or proofers; in healthcare instrument care applications, e.g., soaking, cleaning, and/or rinsing surgical instruments, treating feedwater to autoclave sterilizers; and in feedwater for various applications such as humidifiers, hot tubs, and swimming pools In some embodiments, the water treatment methods can be applied at the point of use. That is, a water treatment method, system, or apparatus can be applied to a water source upstream of an application such as a washing system. In some embodiments, the water treatment is applied immediately prior to the desired end use of the water source. For example, an apparatus of the present invention could be employed to a water line connected to a household or restaurant appliance, e.g., a coffee maker, an espresso machine, an ice machine. An apparatus employing the methods of the present invention may be located in a washing system. For example, it can also be included as part of an appliance which uses a water source, e.g., a water treatment system built into an automatic or manual washing system, a coffee maker, an ice machine, or any other system which may benefit from the use of treated water.

In various applications the anionic surfactants disclosed according to the invention can be dosed directly to the water sources or waste sources which comprise residual quaternary ammonium compounds. The application of the anionic surfactants according to the invention can be utilized to inactivate the quaternary ammonium compounds in the water source or waste streams, which could otherwise negatively interfere with or disrupt bacteria or other compounds therein. Accordingly, it can be desired to inactivate the quaternary ammonium compounds in the water source or waste streams with an in situ inactivation of the antimicrobial compositions.

Kits for Applications of Use

According to various applications of the compositions according to the invention a kit may be provided for dosing a composition according to the invention, including either inactivating or activating a quaternary ammonium composition. In a particular application, the inactivated compositions may be provided by employing a kit according to embodiments of the invention. A kit for dosing and/or providing an inactivating quaternary ammonium composition according to the invention may comprise, consist of and/or consist essentially of a quaternary ammonium compound and an anionic surfactant (and/or chelant and/or polymer). Alternatively, the kits may comprise, consist of and/or consist essentially of an anionic surfactant (and/or chelant and/or polymer) for dosing with a quaternary ammonium compound in an application of use. The kit may further comprise a measuring means and/or a dosing means.

In an aspect, a kit is employed for the dosing of a suitable amount of an anionic surfactant (and/or chelant and/or polymer) to inactivate a quaternary ammonium compound. In an aspect, it may be desirable to dose or provide a surface and/or antimicrobial-inactivating amount of the anionic surfactant (and/or chelant and/or polymer). In embodiments it is desirable to lower surface activity (higher surface tension) as compared to another combination of anionic surfactant (and/or chelant and/or polymer) and a quaternary ammonium compound, such that the low surface activity neutralizes or deactivates the antimicrobial efficacy of the quaternary ammonium compound.

According to some embodiments of employing a kit, a composition and/or system having a quaternary ammonium compound is dosed a molar ratio dependent amount of the anionic surfactant (and/or chelant and/or polymer). In an aspect, the compositions include approximately a mole to mole ratio of quaternary ammonium compound and anionic surfactant. In other aspects, the compositions include up to about a 10 to about a 1 molar ratio of quaternary ammonium compound and anionic surfactant. In other aspects, the compositions include up to about 1 to about a 10 molar ratio of quaternary ammonium compound and anionic surfactant, or any combination thereof. In another embodiment the antimicrobial compositions are provided with a molar ratio of anionic surfactant to quaternary ammonium of about 1 mole anionic surfactant to about 1 mole of quaternary ammonium compound. In another embodiment the antimicrobial composition is provided with a molar ratio of anionic surfactant to quaternary ammonium compound of about 1.5 mole anionic surfactant to about 1 mole of quaternary ammonium compound. In another embodiment the antimicrobial composition is provided with a molar ratio of anionic surfactant to quaternary ammonium compound of about 1 mole anionic surfactant to about 10 moles of quaternary ammonium compound. In another embodiment the antimicrobial composition is provided with a molar ratio of anionic surfactant to quaternary ammonium compound of about 2 moles anionic surfactant to about 1 mole of quaternary ammonium compound. In each embodiment, the kit provides the mole ratio to inactivate the quaternary ammonium compound.

The kit may further comprise additional elements. For example, a kit may also include instructions for use of the inactivated compositions. Instructions included in kits can be affixed to packaging material or can be included as a package insert. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD, DVD), and the like. As used herein, the term "instructions" can include the address of an internet site that provides the instructions. The various components of the kit optionally are provided in suitable containers as necessary, e.g., a bottle, jar or vial.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

BARDAC 2250 R and 2280 R as used in the Examples herein are available from Lonza, Inc. and are each twin chain dimethyl ammonium chlorides. Bardac 2250 R includes 50 wt % didecyl dimethyl ammonium chloride, 10 wt % ethyl alcohol, and 40 wt. % water. Bardac 2280 R includes 80 wt % didecyl dimethyl ammonium chloride, 10 wt. % ethyl alcohol, and 10 wt. % water. Various other commercially-available quaternary ammonium compounds and structures of the raw materials are outlined in Table 2.

TABLE 2

| Raw Material | Chemical Structure |
|---|---|
| Uniquat QAC-50 | Alkyl Benzyl ammonium chloride |
| Bardac 205M | Blend: Dialkyl/Alkyl Benzyl ammonium chloride |

TABLE 2-continued

| Raw Material | Chemical Structure |
| --- | --- |
| Bardac 2250 | Didecyl (C10) dimethyl ammonium chloride |
| Bardac 2050 | Blend: Didecyl/dioctyl dimethyl ammonium chloride |
| Bardac LF80 | Dioctyl (C8) dimethyl ammonium chloride |
| Acusol 445 | 4500 MW homopolyacrylate |
| PSO | phosphosuccinate adducts/oligomer |
| AQUATREAT ® AR 801 | low molecular weight partially neutralized maleic homopolymer |
| Dequest 2000 | amino tri methylene phosphonic acid scale inhibitor |
| Trilon M | methyl glycine diacetic acid (MGDA) |
| GLDA | glutamic acid-N,N-diacetic acid |
| Surfonic 12-6 | decyl/lauryl alcohol ethoxylate with 6 EO |

Example 1

Dynamic Surface Tension of Bardac 205M and Anionic Surfactant

The SITA science line t60 measures the dynamic surface tension of liquids up to the semi-static range. Air bubbles are generated from a capillary with known radius. The bubble pressure is measured as a function of bubble life time, which can be correlated to the surface tension according to the Young-Laplace equation. Dynamic surface tension provides insight in to the dynamic behavior of surfactants and other surface active compounds under dynamic conditions, i.e. how quick surfactants can reach a surface. The dynamic surface tension behavior of surfactants is particularly important in applications where a quick response of surfactant is required, for example, in short rinse cycles of automated dishwashing.

Apparatus and Materials
1. SITA T60 (Sita Messtechnik, Germany)
2. Oil bath with stir bar
3. Heating and stirring plate
4. Glass beakers
5. Glass vials (20 mL)

The SITA science line t60 was calibrated with DI water. Clean water samples after calibration should have a surface tension of 72.0±1.0 mN/m (depending on the quality and temperature). Following calibration, the SITA was programmed to take readings at the desired time intervals (i.e., 0.3, 1.6, 3.0, 9.1 seconds). In order to determine the effects on the surface activity of a 9:1 mass ratio of quaternary ammonium compound with an anionic surfactant the following compositions were prepared.

Bardac 205M is a commercially available quaternary ammonium compound from Lonza having 20 wt. % active alkyl dimethyl benzyl ammonium chloride, 15 wt. % octyl decyl dimethyl ammonium chloride, 6 wt. % dioctyl dimethyl ammonium chloride, and 9 wt. % dodecyl dimethyl ammonium chloride. Bardac 205M quaternary ammonium compound blend further includes inert ingredients of 10 wt. % ethyl alcohol and 40 wt. % water. The samples of this Example were prepared using 100 ppm Bardac205M. The Bardac 205M was combined each with Plurafac SL-42 (a comparative nonionic surfactant—ethoxylated, propoxylated C6 to C10 extended chain surfactant anionic surfactant available from BASF), Surfonic PEA (an amine surfactant-neutral or cationic depending upon pH—comparative ethoxylated ether amine available from Huntsman Chemical), X-AES (anionic surfactant $C_{12-14}$-$(PO)_{16}$-$(EO)_2$-sulfate available from Huntsman Chemical), SLES (anionic surfactant—sodium lauryl ether sulfate), and Marlowet4539 (C9-alcohol polyethylene glycol ether carboxylic acid available from Sasol) at a 9:1 mass ratio.

10-15 mL were transferred into 20 mL vials and immersed in a heated oil bath to 72° C. (160° F.)±2° C. The samples were equilibrated for 10-15 minutes. The samples were individually removed from the oil bath and tested in the SITA. After each sample was tested the SITA's cleaning procedure was run, then the surface tension of DI water was checked to ensure the SITA was adequately clean. If the DI water measurements were not within 72.0±1.0 mN/m, then the cleaning procedure was run again. The surface tension (mN/m) versus bubble life time at 160° F. was recorded and the experimental data is provided in FIG. 1.

The results shown in FIG. 1 provide that an increase in dynamic surface activity is observed for most of the quaternary ammonium-anionic surfactant blends tested. As referred to throughout the Examples, an increase in dynamic surface activity is shown by a decrease in surface tension over the course of the bubble lifetime depicted in the figures. Specifically, Bardac 205M+Marlowet4539 and Bardac 205M+Colatrope INC displayed a significant increase in surface activity compared to Bardac 205M alone. Interestingly, the quat-nonionic surfactant blends, Bardac 205M+Plurafac SL-42 and Bardac 205M+Surfonic PEA, displayed only mild synergy. Whereas, the Bardac 205M with either X-AES or SLES (both of which are longer alkyl alkoxylated sulfates) do not display the synergistic boost in surface activity observed with the other quat-anionic surfactant blends.

Example 2

Dynamic Surface Tension of Bardac 205M and Anionic Sulfate Surfactant Blends

To further examine the surface activity of a mole:mole ratio of quaternary ammonium compound with different anionic sulfate surfactants, the procedure described in Example 1 was followed. Bardac 205M as described above was combined each with SLS (sodium lauryl sulfate), SLES (sodium lauryl ether sulfate), X-AES ($C_{12-14}$-$(PO)_{16}$-$(EO)_2$-sulfate available from Huntsman Chemical), and Stepanol EH-S(Sodium 2-ETHYL HEXYL SULFATE available from Stepan) at a mole:mole ratio. The results are provided in FIG. 2.

Figure 2:
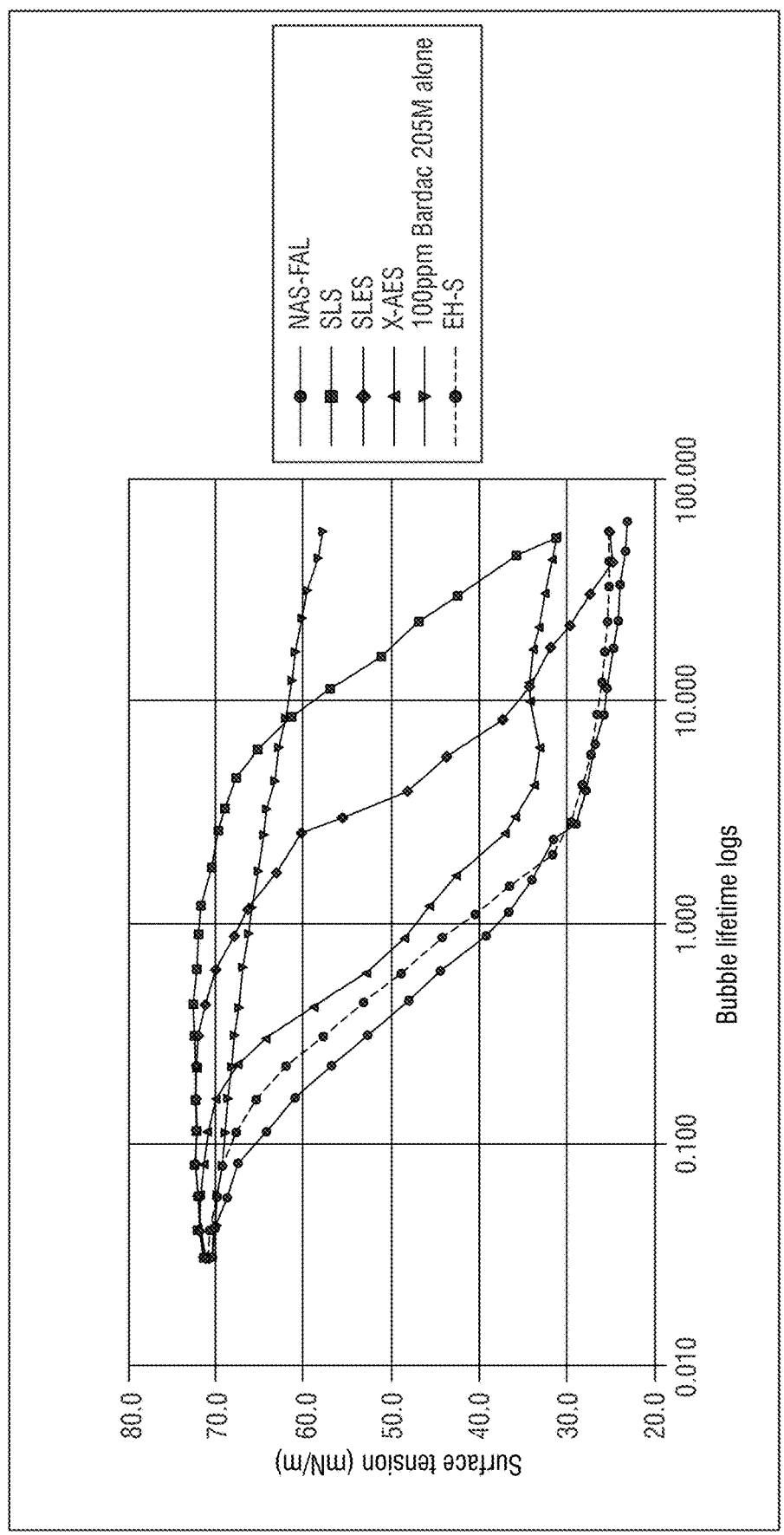
FIG. 2 is a plot showing Dynamic Surface Tension of compositions prepared with a mole:mole ratio of quaternary ammonium compound:anionic sulfate surfactant.

The results shown in FIG. 2 demonstrate that the combinations exhibit chain length dependent surface activity as compared to the quaternary ammonium compound (Bardac 205M) alone (at this molar ratio). For example, Bardac 205M in combination with EH-S or X-AES or NAS-FAL all showed a rapid increase in surface activity. Whereas, the Bardac 205M, SLS or SLES blends resulted in an overall increase in surface activity compared to Bardac 205M alone, but displayed slower dynamics compared to the other blends tested, illustrating an inactivation of antimicrobial activity.

Quaternary ammonium compounds themselves are known to have superb micro efficacy, however, they are not very surface active material. When the quaternary ammonium compounds are paired with a suitable anionic surfactant, the combination is more surface active than the two individuals. The synergy in antimicrobial efficacy activation correlates quite well with dynamic surface tension synergy. Without being bound by theory, we believe that a complex, or ion pair, between a quat and anionic surfactant, because of the charge neutralization, has very similar effective cross-sectional areas for both the hydrophile and hydrophobe, making stacking in interfaces very favorable, unless they are not soluble any more. The complex formation is so favorable that it can overcome the cohesive force between fatty acid molecules.

Example 3

Dynamic Surface Tension of Mole-Mole Ratio Bardac 205M with Anionic Carboxylate Surfactants The dynamic surface tension of a mole:mole ratio of quaternary ammonium compound with different anionic carboxylate surfactants were tested following the procedure of Example 1. The following solutions were prepared: Bardac 205M at a concentration of 100 ppm as described above was combined each with 48 ppm ethylhexoic acid, 52 ppm Colatrope INC (sodium alkanoate available from Colonial Chemical Inc.), 48 ppm octanoic acid, 116 ppm Marolwet4539 SLS (C9-alcohol polyethylene glycol ether carboxylic acid available from Sasol), 56 ppm decanoic acid, and 65 ppm lauric acid at a mole:mole ratio. These data are provided in FIG. 3.

Figure 3A:
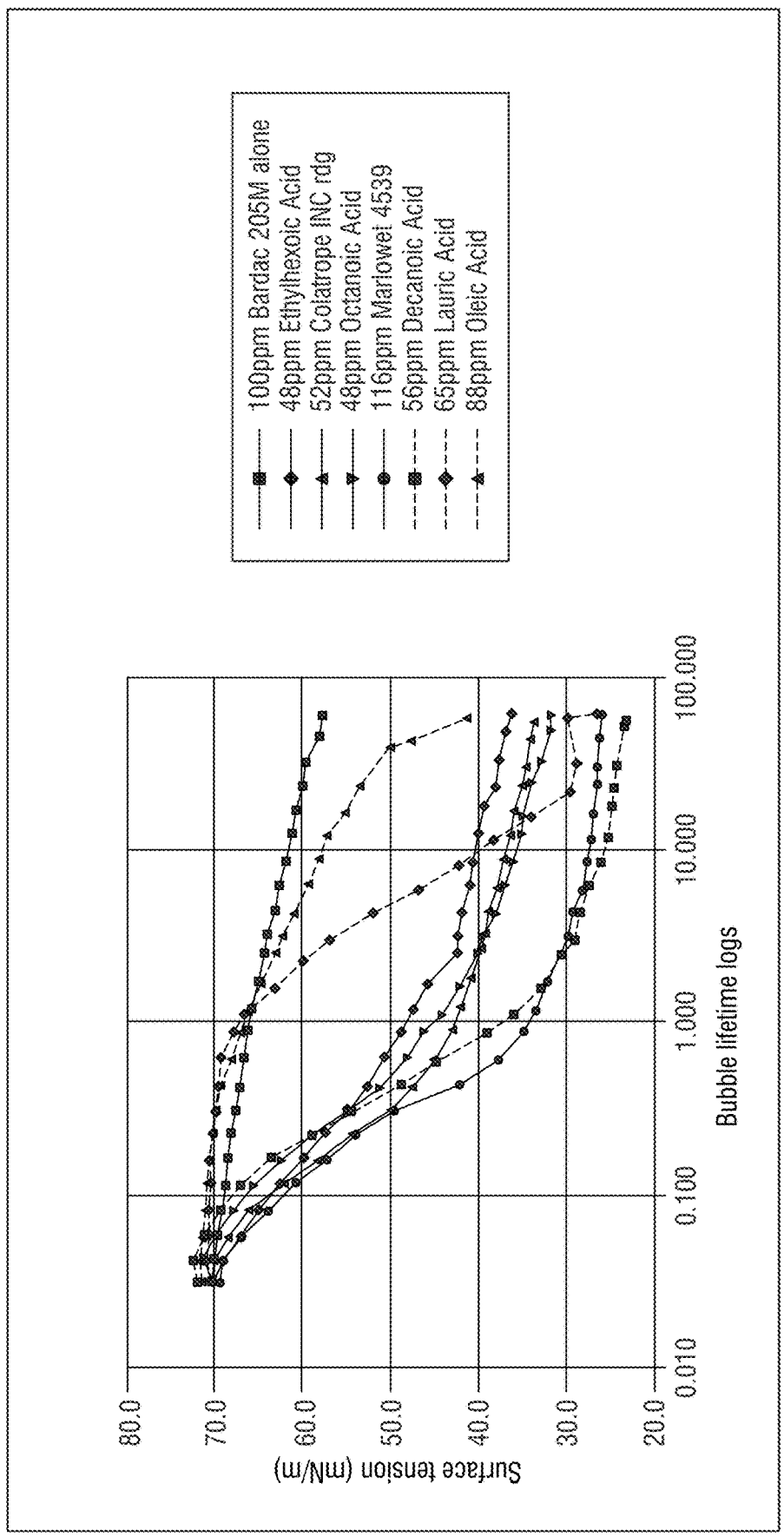
FIG. 3A is a plot showing Dynamic Surface Tension of compositions prepared with a mole:mole ratio of Bardac 205M quaternary ammonium compound:anionic carboxylate surfactants as evaluated according to embodiments of the invention.
Figure 3B:
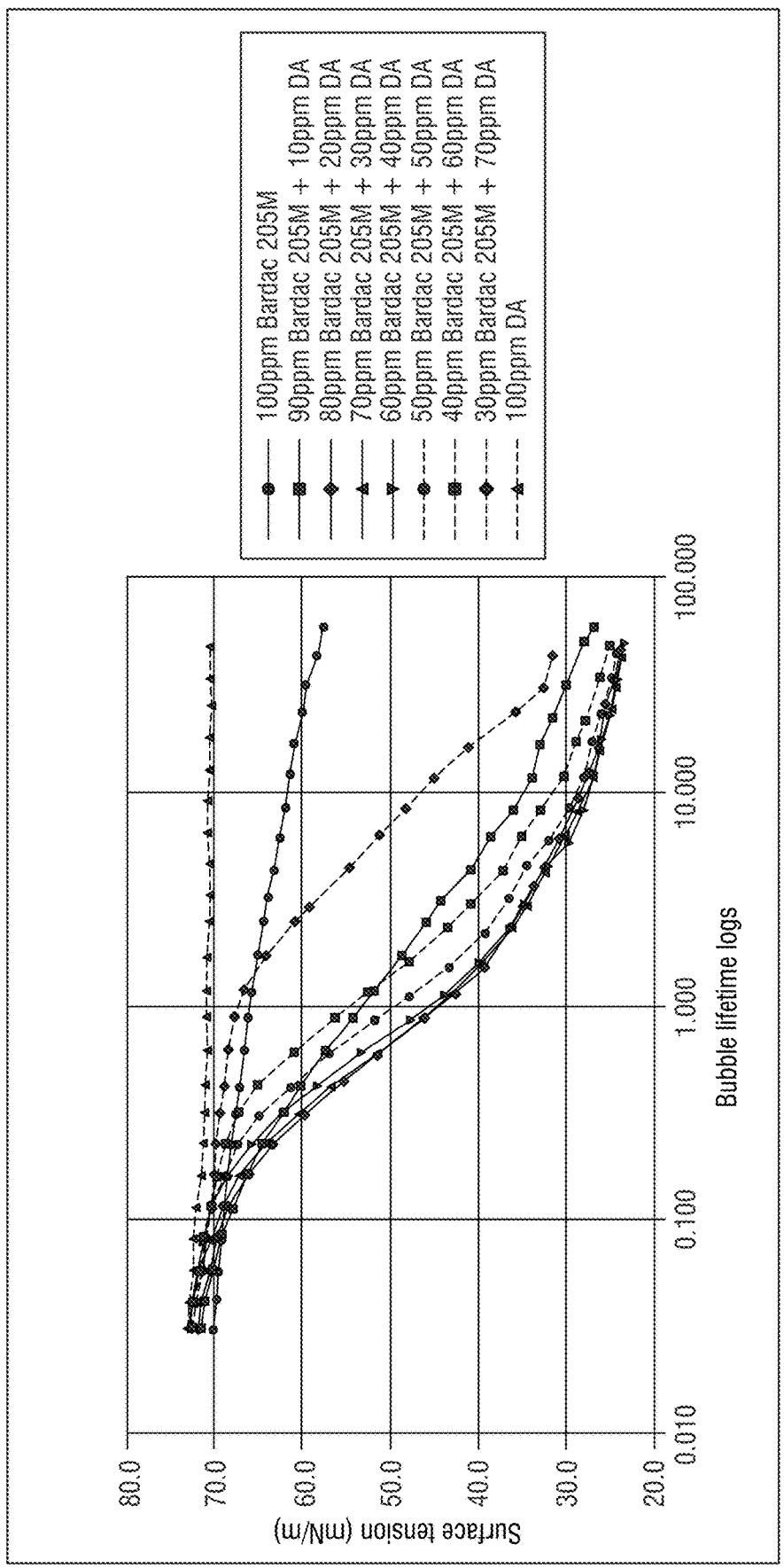
FIG. 3B is a graphical depiction of the Dynamic Surface Tension of Bardac 205M and varying concentrations of Decanoic acid as described in Example 3.

The results shown in FIG. 3A demonstrate that the combinations of carboxylated anionic surfactants and quaternary ammonium compounds have reduced surface activity as compared to the quaternary ammonium compound (Bardac 205M) alone. The combination of Bardac 205M with decanoic acid appears to be particularly suitable at increasing the dynamic surface activity compared to Bardac 205M alone. As can be seen in FIG. 3A, ethylhexoic acid, Colatrope INC, octanoic acid, Marolwet4539 SLS, decanoic acid, Lauric acid, and Oleic acid are all capable of increasing the surface activity, to variable extents, compared to Bardac 205M alone.

Further dynamic surface tension analysis was preformed using the above procedure. The following solutions were prepared: Bardac 205M at a concentration of 100 ppm as described above was combined with Decanoic acid at varying concentrations (10 ppm, 20 ppm, 30 ppm, 40 ppm, 50 ppm, 60 ppm, and 70 ppm) or 100 ppm Decanoate alone. The results are provided in FIG. 3B.

As can be seen by these results, Decanoate alone and Bardac 205M alone, display limited surface activity. However, when each is combined a dramatic increase in surface activity is observed. Furthermore, the observed increase in surface activity of the quat-decanoic acid blend occurs in a dose-dependent manner. That is, the observed synergistic trend occurs as a function of anionic surfactant concentration.

Beneficially, the medium chain length carboxylated anionic surfactants show especially unusual interaction with the quat. In a preferred aspect of the invention, decanoic acid is employed in the antimicrobial compositions. Decanoic acid is a solid material at room temperature with extremely low solubility yet it dissolves freely with the (slightly acidic) quat with no addition of any alkalinity. Also, in a wide range of pH, the complex formed has very similar strong surface activity providing an unexpected result. As shown the surface activity is independent of pH.

Example 4

Dynamic Surface Tension of Bardac 205M and Anionic Sulfate Surfactant Combinations The surface tension of a mole:mole ratio of quaternary ammonium compound with different sulfate based anionic surfactants were examined following the procedure outlined in Example 1. The following solutions were prepared. Bardac 205M at a concentration of 100 ppm as described above was combined each with 84 ppm SLS (sodium lauryl sulfate), NAS-FAL (sodium n-octanesulfonate), and Stepanol EH-S(Sodium 2-ethyl hexyl sulfate available from Stepan) at a mole:mole ratio. These data are provided in FIGS. 4A, 4B, and 4C respectively.

Figure 4A:
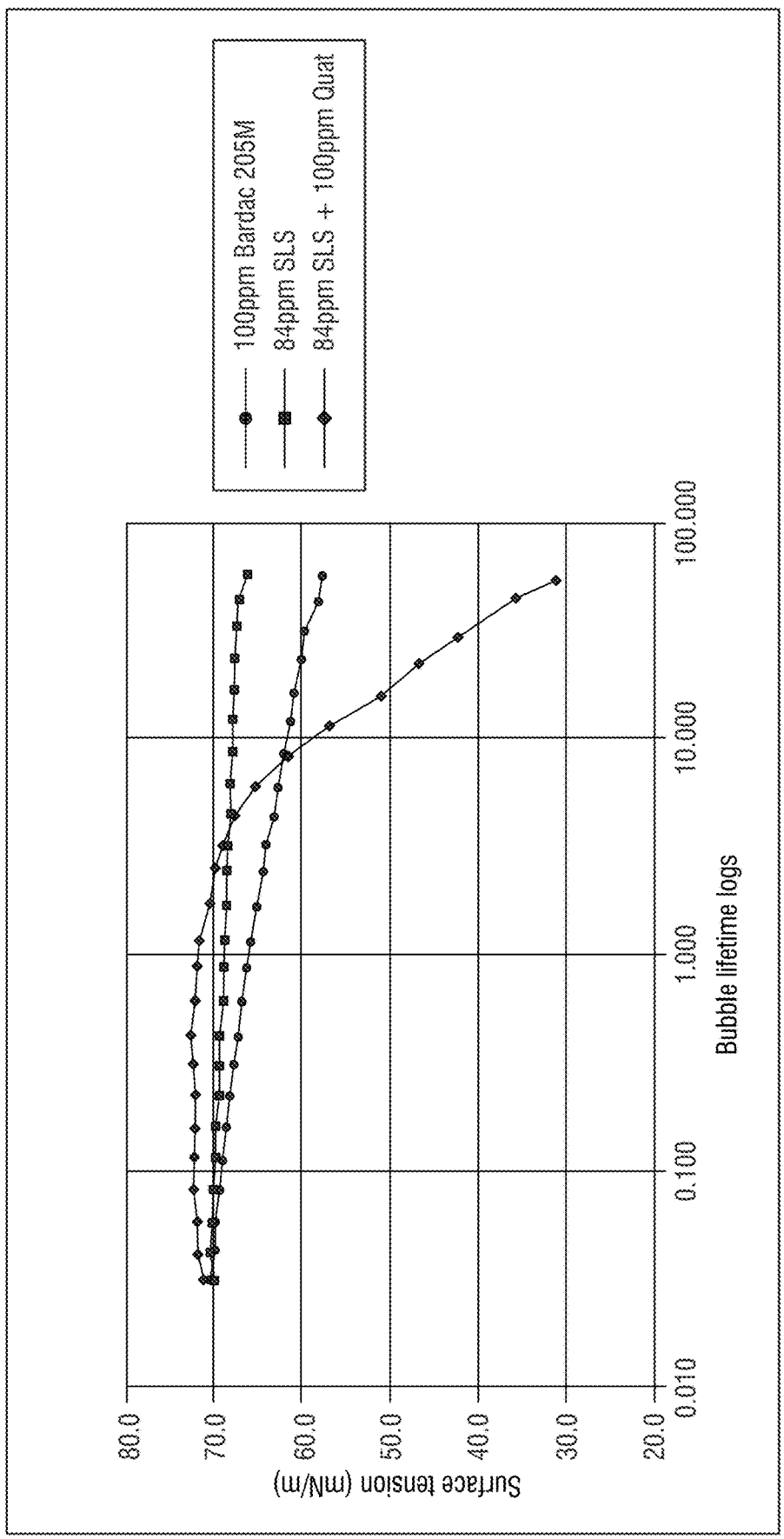
FIG. 4A-4C depict plots comparing Dynamic Surface Tension of compositions prepared with quaternary ammonium compound interaction with various sulfate based anionic surfactants against compositions prepared with quaternary ammonium compound with a carboxylate anionic surfactant.

The results shown in FIG. 4A demonstrate that the mole:mole combination of sodium lauryl sulfate with quaternary ammonium Bardac 205M displays a reduced dynamic surface tension, as compared to either the quaternary ammonium compound or the anionic surfactant alone. Interestingly, when viewed in combination with the results of FIG. 4B and FIG. 4C, the blend of Bardac 205M+SLS shows a slower decrease in surface tension over the first half of the bubble lifetime and then rapid decrease in surface tension over the second half of the experiment.

Figure 4B:
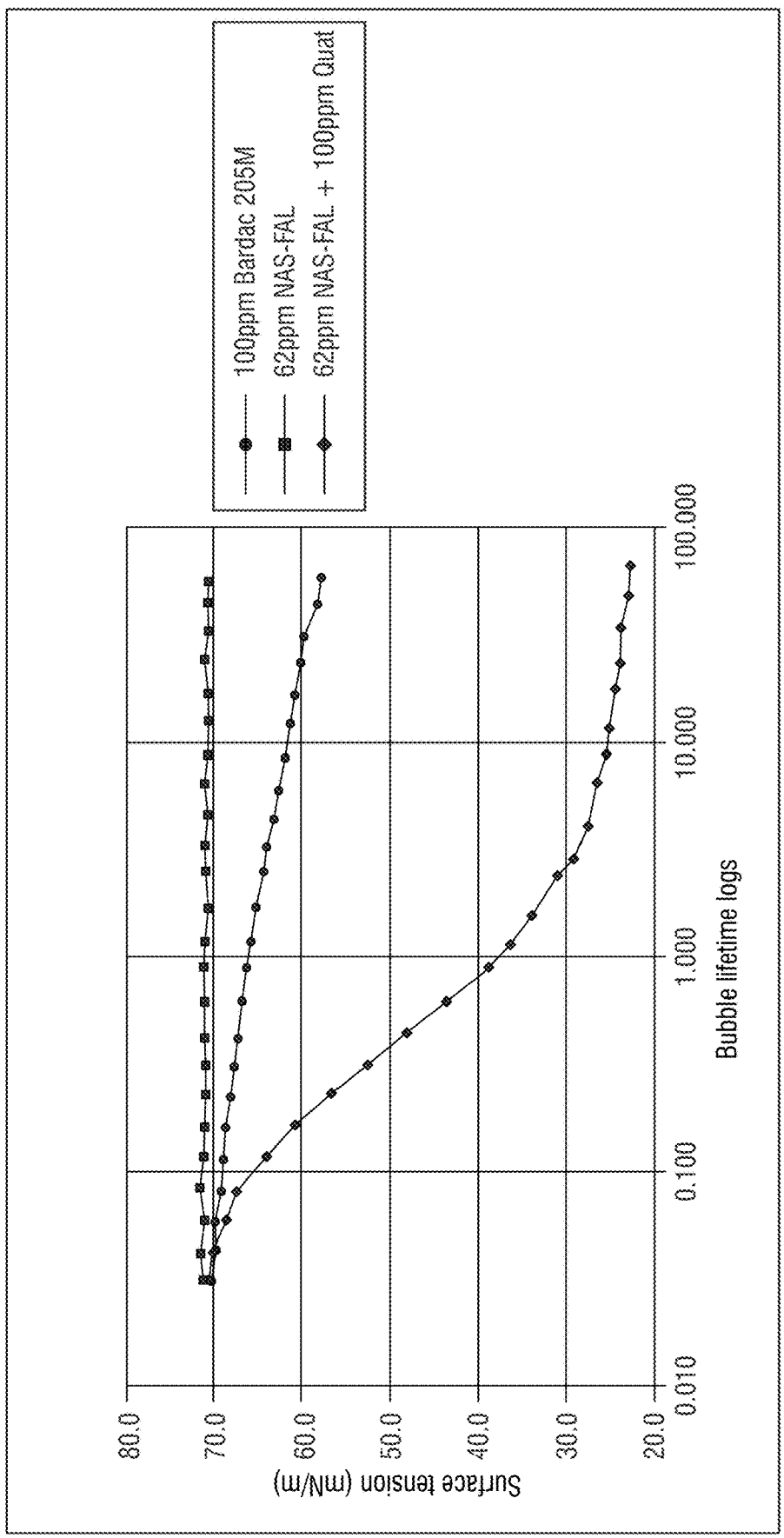

The results shown in FIG. 4B are consistent with the results of FIG. 4A. and demonstrate that the mole:mole combination of sodium n-octanesulfonate with quaternary ammonium Bardac 205M shows a synergistic trend in regards to reduced surface tension as compared to either the quaternary ammonium compound or the anionic surfactant alone. In contrast to the results of FIG. 4A, a rapid decrease in surface tension is observed.

Figure 4C:
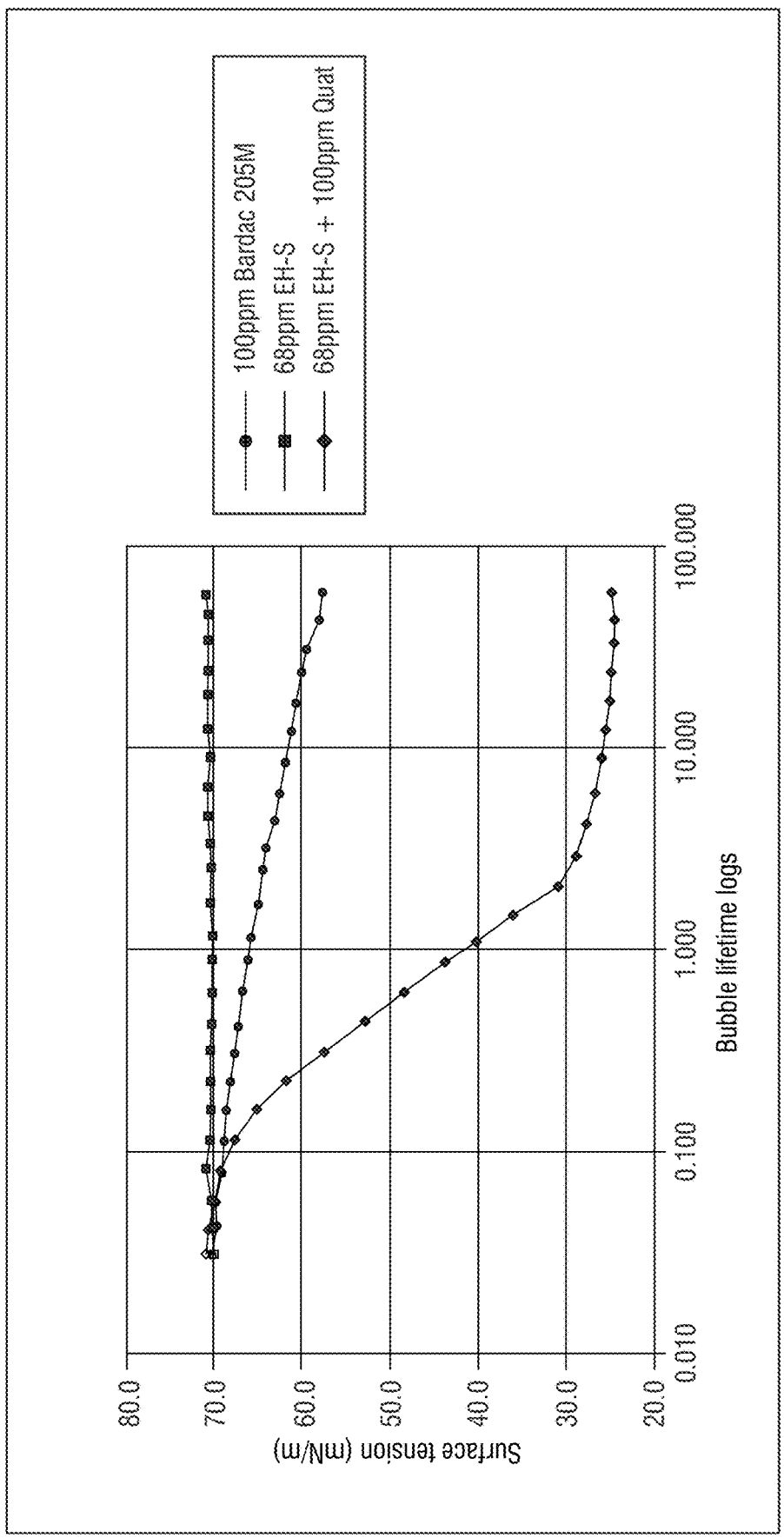

The results shown in FIG. 4C are consistent with the observations seen in FIGS. 4A and 4B. As can be seen in FIG. 4C the mole:mole combination of sodium 2-ethyl hexyl sulfate with quaternary ammonium Bardac 205M also displays a synergistic reduction of surface tension as compared to either the quaternary ammonium compound or the anionic surfactant alone. Furthermore, the dynamic decrease in surface tension observed in FIG. 4C is similar to the dynamics shown in FIG. 4B.

Example 5

Quaternary Ammonium-Anionic Surfactant Compound pH Study

Figure 5A:
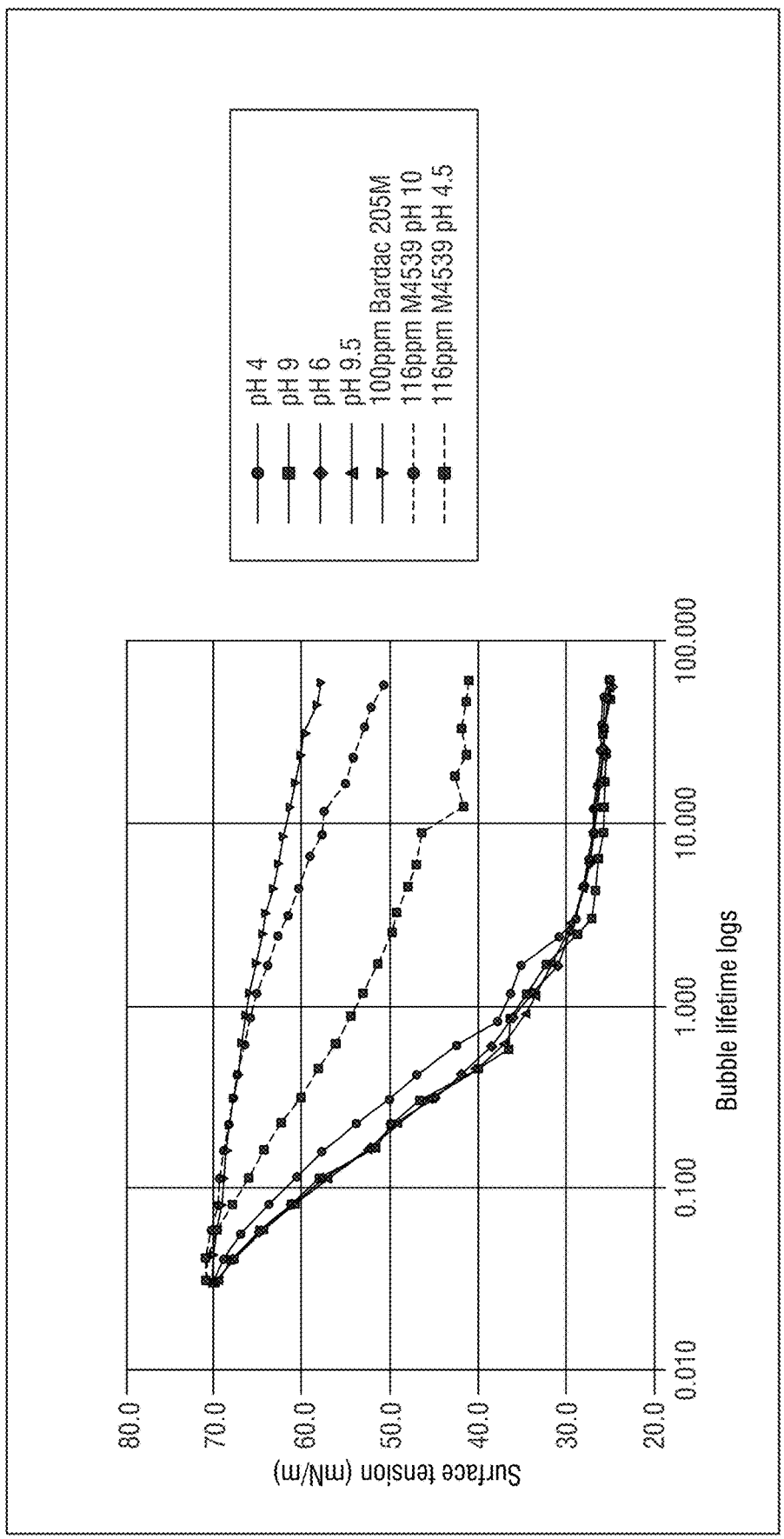
FIG. 5A is a plot showing the pH of compositions prepared with quaternary ammonium compound and carboxylate based anionic surfactants on a molar ratio basis as evaluated according to an embodiment of the invention.

In order to determine the effects of pH on the observed synergistic boost in surface activity between the mole:mole ratio of quaternary ammonium compound and carboxylate based anionic surfactant the procedure outlined in Example 1 was used except the solutions were prepared at various pH. Bardac 205M quaternary ammonium was combined with Marlowet 4539 (C9-alcohol polyethylene glycol ether carboxylic acid available from Sasol) on a mole:mole basis. The pH of the combination was adjusted using HCl and the surface tension of the combination at pH 4.0, 6.0, 9.0, and 9.5 and plotted for comparison against 100 ppm Bardac 205M and 116 ppm Marlowet 4539. The results are provided in FIG. 5A.

The data demonstrates the observed synergy between Bardac 205M and Marlowet 4539 is maintained at various pH. The surface tension of the solutions of Bardac 205M in combination with Marlowet 4539 decrease at comparable rates regardless of pH. Whereas pH does appear to influence the surface tension of Marlowet 4539 solutions alone, as the solution with a pH of 4.5 was more surface active compared to the solution at a pH of 10.0.

Figure 5B:
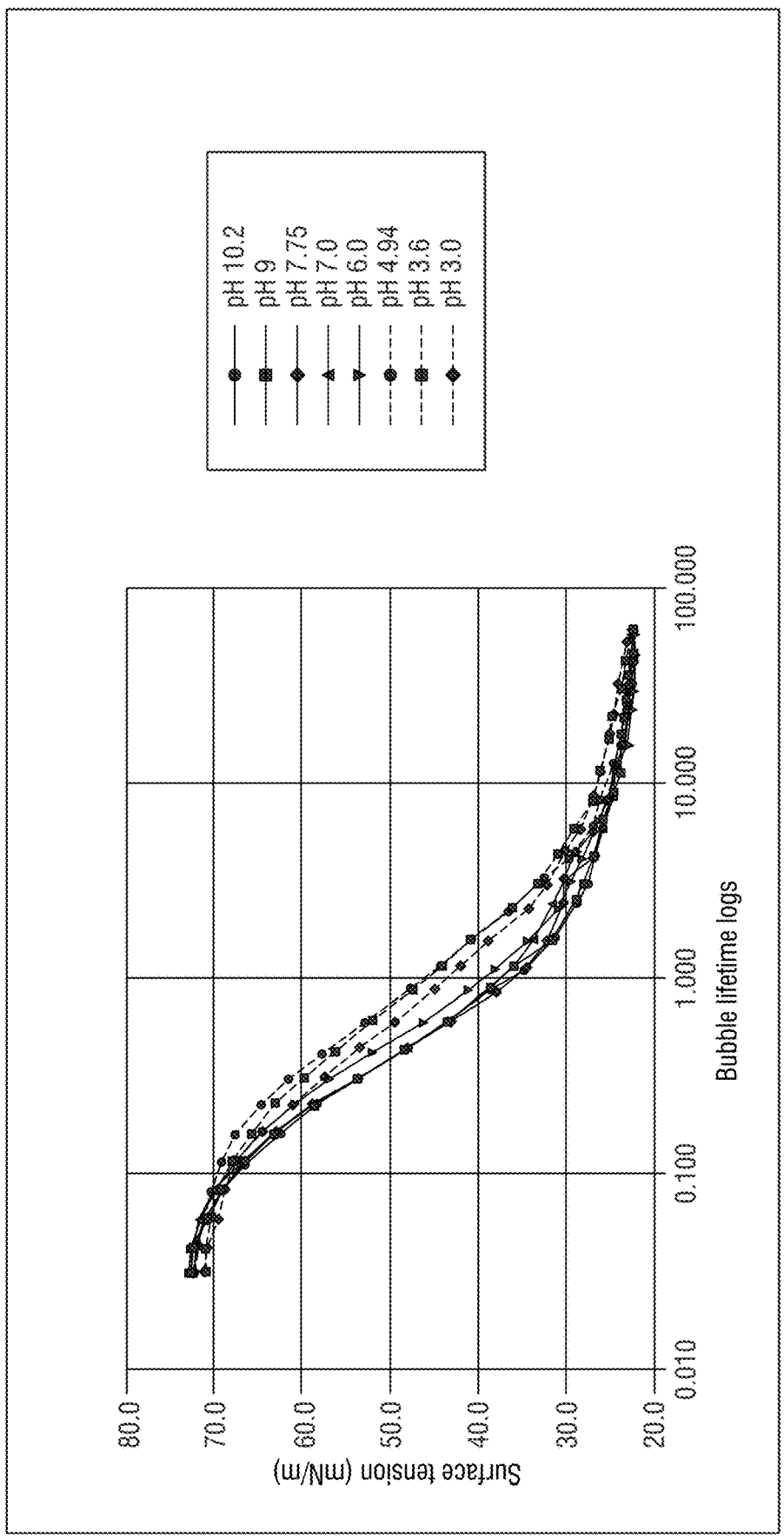
FIG. 5B is a plot showing the pH of compositions prepared with quaternary ammonium compound and carboxylate based anionic surfactants on a molar ratio basis as evaluated according to embodiments of the invention.

Further examination on the effect of pH on the dynamic surface tension of a combination of mole:mole ratio of 100 ppm Bardac 205M quaternary ammonium compound and 56 ppm decanoic acid were examined as described above. The pH of the combination was adjusted and the dynamic surface tension of the combination was observed at pH 3.6, 4.94, 6, 7, 7.75, 9, and 10.2. The results are provided in FIG. 5B showing the dynamic surface tension of the mole:mole combination of quaternary ammonium and decanoic acid was independent of pH. Thus, the dynamic surface tension did not vary even though the pH changed. An observation consistent with the data shown in FIG. 5A.

Example 6

Antimicrobial Efficacy of Quaternary-Anionic Surfactant Compositions

Figure 6A:
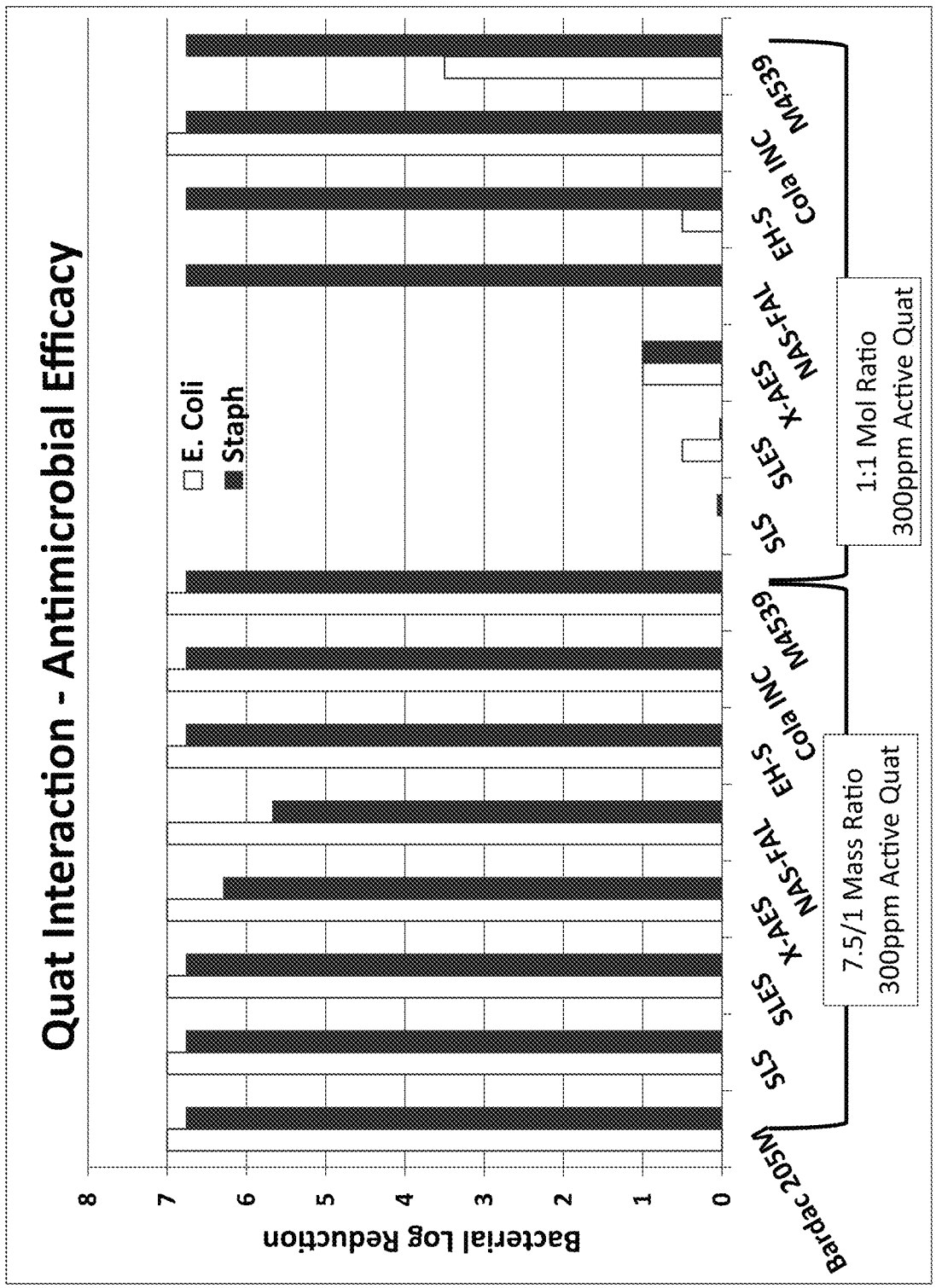
FIG. 6A is a plot illustrating the antimicrobial efficacy of compositions of the invention against *Escherichia coli* and *Staphylococcus aureus* at distinct molar ratios as evaluated according to embodiments of the invention.

The antimicrobial efficacy of a quaternary ammonium compound in association with an anionic surfactant is shown in FIG. 6A utilizing an antimicrobial suspension test. The combinations include a 7.5 to 1 mass ratio of 300 ppm active Bardac 205M combined with each of SLS, SLES, X-AES, NAS-FAL, Ethylhexyl-Sulfate (EH-S), Colatrope INC, and M4539. The same anionic surfactants were combined with 300 ppm Bardac 205M in a mole to mole ratio. Bardac 205M is commercially available from Lonza having 20 wt. % active alkyl dimethyl benzyl ammonium chloride, 15 wt. % octyl decyl dimethyl ammonium chloride, 6 wt. % dioctyl dimethyl ammonium chloride, and 9 wt. % dodecyl dimethyl ammonium chloride. Bardac 205M quaternary ammonium compound blend further includes inert ingredients of 10 wt. % ethyl alcohol and 40 wt. % water.

The results shown in FIG. 6A demonstrate that the 7.5/1 mass ratio of Bardac 205M to SLS, SLES, X-AES, EH-S and M4539 provided the highest log reduction of bacteria for *E. coli*. The combined Bardac 205M with SLS, SLES and X-AES also provided good antimicrobial efficacy against *Staphylococcus*. Additionally, the data analyzing the mole: mole ratio of Bardac 205M provide the Cola INC and M4539 combinations display the highest log reduction for *E. coli*. The combination of Bardac 205M with NAS-FAL, EH-S, Colatrope INC and M4539 also provided good antimicrobial efficacy against *Staphylococcus*. While quaternary ammonium compositions alone are known to be very good antimicrobial agents, however quaternary ammonium compounds are not very surface active compositions limiting their usefulness as surface active agents, such as sanitizing agents. These results show that the antimicrobial efficacy is maintained in quaternary ammonium-anionic surfactant compositions, while the surface activity of the combinations are greatly enhanced compared to quaternary ammonium compounds alone (see FIGS. 1-4C).

Figure 6B:
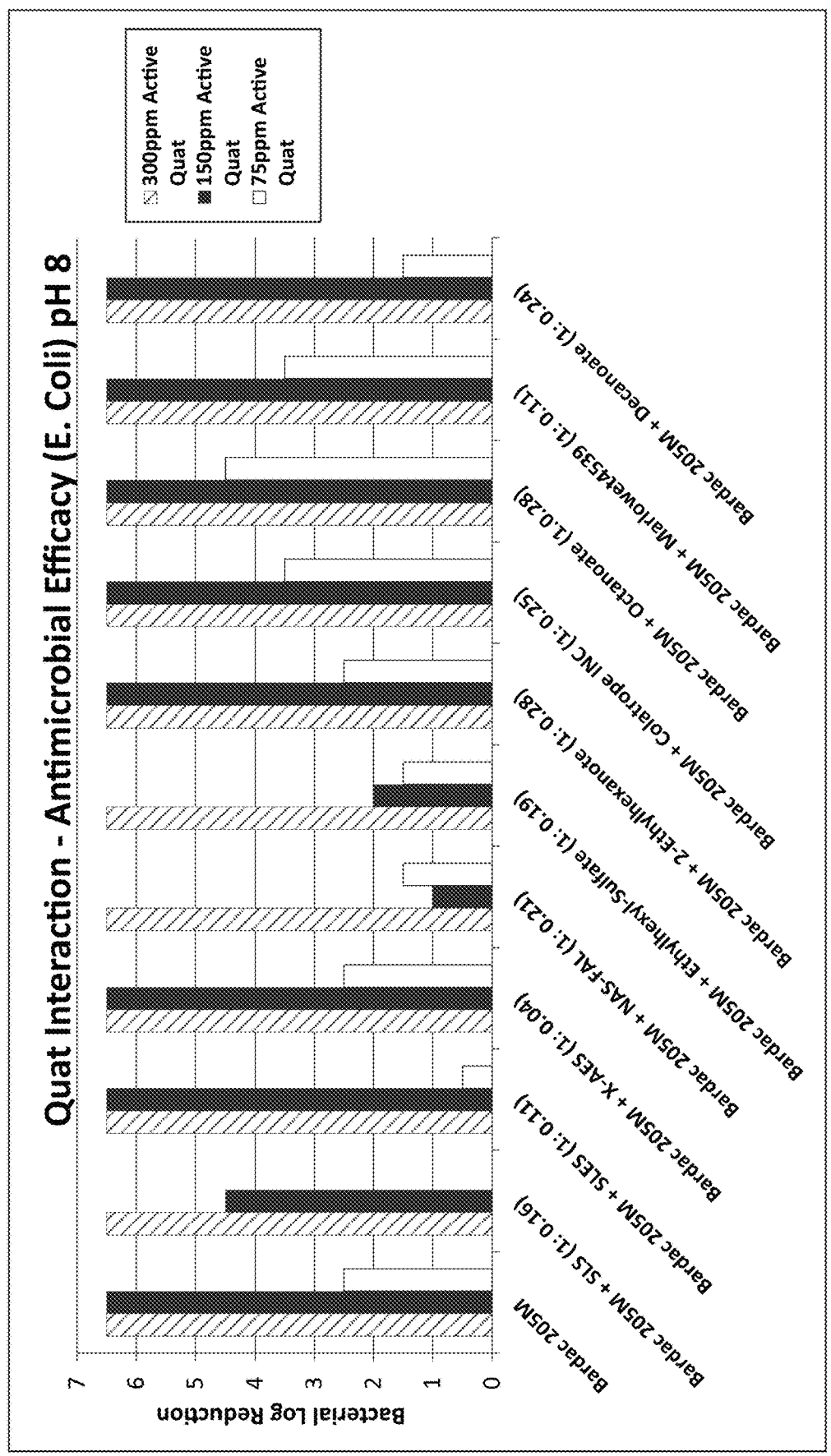
FIG. 6B is a plot illustrating the antimicrobial efficacy of compositions of the invention prepared with a quaternary ammonium:anionic surfactant ratio of 7.5:1 mass ratio with 300 ppm, 150 ppm and 75 ppm Bardac 205M as evaluated according to embodiments of the invention.

Further examination of the antimicrobial efficacy of a quaternary ammonium compound in association with an anionic surfactant at pH 8.0 was performed as described above. The combinations include a 7.5 to 1 mass ratio of 300 ppm, 150 ppm, and 75 ppm active Bardac 205M combined with each of SLS, SLES, X-AES, NAS-FAL, Ethylhexyl-Sulfate (EH-S), 2-Ethylhexanote, Colatrope INC, Octanoate, Marlowet4539, and Decanoate. Bardac 205M is commercially available from Lonza which composition is as described above. The results are provided in FIG. 6B.

The results demonstrate that the 7.5/1 mass ratio of Bardac 205M to SLS, SLES, X-AES, NAS-FAL, Ethylhexyl-Sulfate, 2-Ethylhexanote, Colatrope INC, Octanoate, Marlowet4539, and Decanoate provided the highest log reduction of bacteria at 300 ppm of the quaternary ammonium compound. The combined Bardac 205M with SLES and X-AES, 2-Ethylhexanoate, Colatrope INC, Octanoate, Marlowet4539, and Decanoate also provided good antimicrobial efficacy at 150 ppm quaternary ammonium compound.

Example 7

Antimicrobial Efficacy of Quaternary-Anionic Surfactant Compositions

Figure 7:
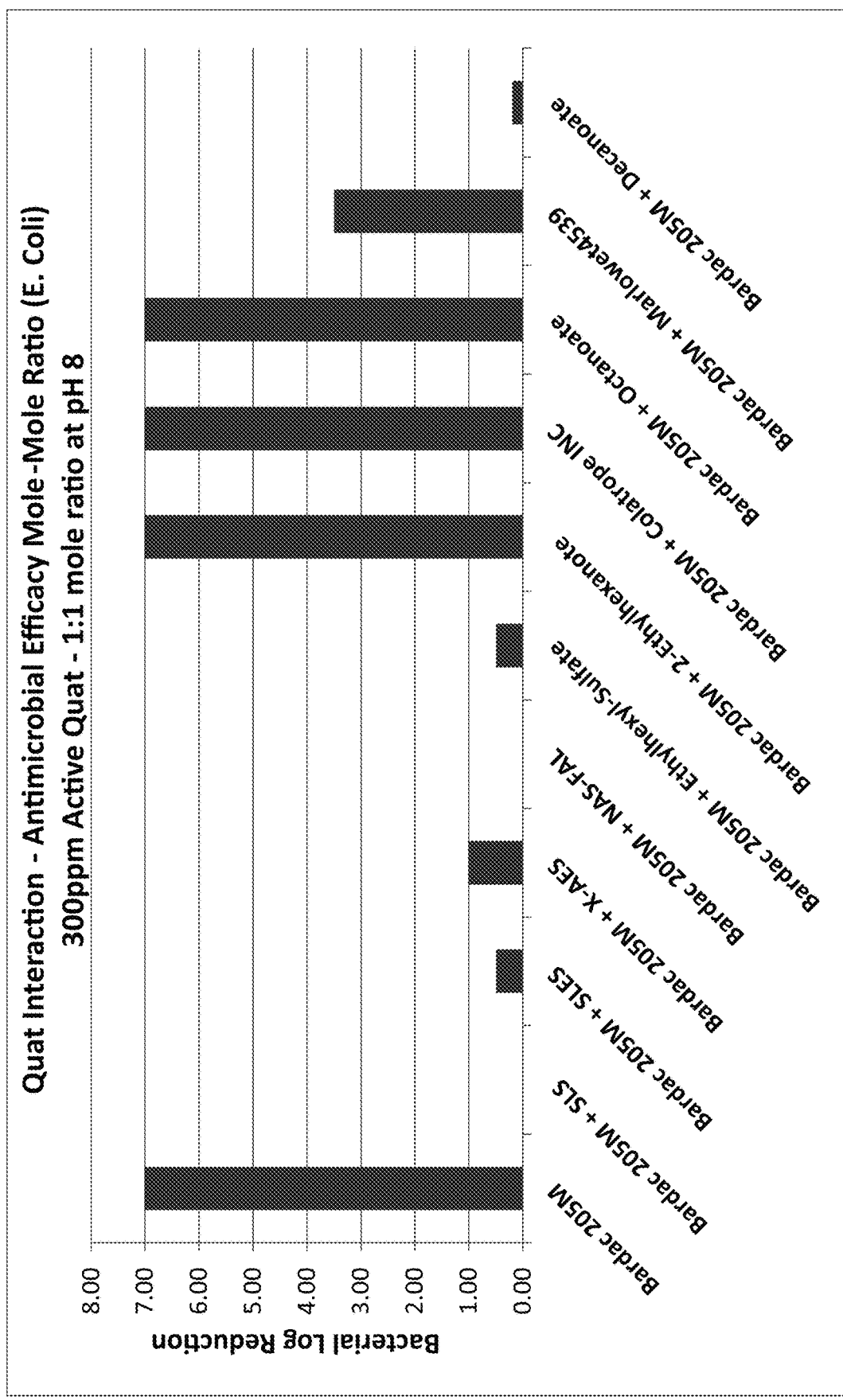
FIG. 7 is a plot showing the antimicrobial efficacy of different anionic surfactants in combination with quaternary ammonium Bardac 205M as evaluated according to embodiments of the invention.

The antimicrobial efficacy of compositions of the invention against *E. coli* is shown in FIG. 7. Compositions were tested with combinations of 300 ppm Bardac quaternary ammonium compound combined in a mole:mole ratio with each of SLS, SLES, X-AES, NAS-FAL, Ethylhexyl-Sulfate (EH-S), 2-Ethylhexanoate, Colatrope INC, Octanoate, Marlowet4539, and Decanoate. All test compositions were at pH 8.

Figure 8:
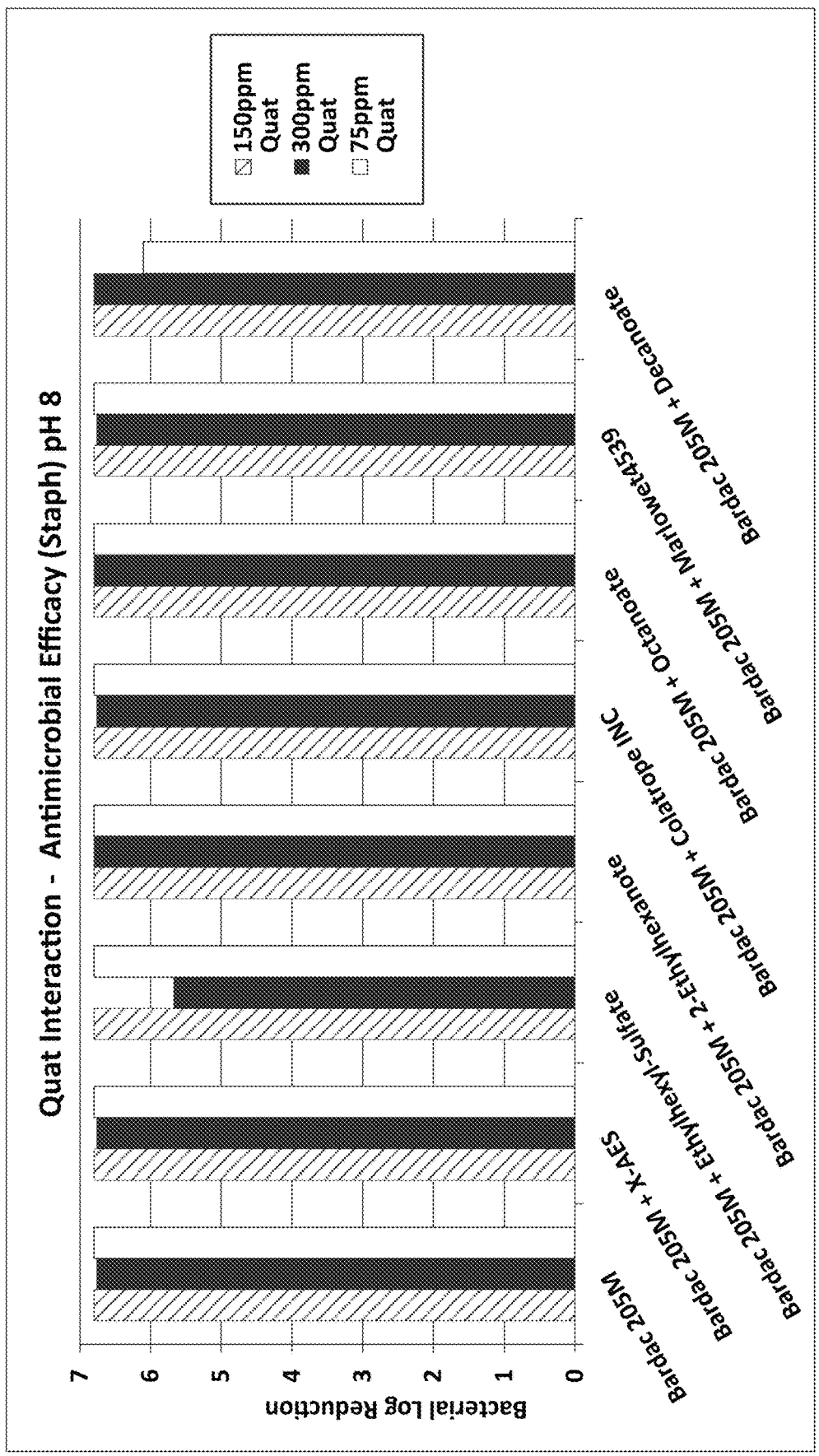
FIG. 8 is a plot illustrating the antimicrobial efficacy of compositions of the invention on *Staphylococcus*.

The results illustrated in FIG. 8 demonstrate that the highest log reduction of bacteria occurred with the combination of Bardac 205M with 2-Ethylhexanoate, Colatrope INC and Octanoate. The combination of Bardac 205M quaternary ammonium and Marlowet4539 demonstrated bacterial kill to a lesser extent than the others.

The results further demonstrate that rather than heightening the antimicrobial efficacy, some interactions serve to decrease the antimicrobial efficacy of the quaternary ammonium. In particular, with respect to kill of *E. coli*, the quaternary ammonium combined each with SLS, SLES, X-AES, NSA-FAL, Ethylhexyl-Sulfate and decanoate all serve to reduce the antimicrobial activity of the quaternary ammonium compound. The interactions between these anionic surfactants and quaternary ammonium compound is said to be destructive or demonstrate a 'deactivation' effect.

Without being bound by theory, the present invention demonstrates that a complex, or ion pair, between a quat and anionic surfactant, because of the charge neutralization, has very similar effective cross-sectional areas for both the hydrophile and hydrophobe, making stacking in interfaces very favorable, unless they are not soluble any more. The complex formation is so favorable that it can overcome the cohesive force between fatty acid molecules. This testing demonstrates the stronger ionic bonding as found in sulfates or sulfonates anionic surfactants work to neutralize, reduce solubility, and/or inactivate an antimicrobial quaternary ammonium compound. It is also believed that due to weaker ionic bonding, carboxylated anionic surfactants appear to enhance or activate an antimicrobial quaternary ammonium compound. It is likely that other weak acid anionic surfactants such as phosphate esters would also serve to activate antimicrobial activity.

Example 8

Antimicrobial Efficacy of Quaternary-Anionic Surfactant Compositions

The antimicrobial efficacy on *Staphylococcus* of a quaternary ammonium compound in association with an anionic surfactant at pH 8 is shown in FIG. 8. The combinations include a 7.5 to 1 mass ratio of 300 ppm, 150 ppm, and 75 ppm active Bardac 205M combined with each of X-AES, Ethylhexyl-Sulfate (EH-S), 2-Ethylhexanote, Colatrope INC, Octanoate, Marlowet4539, and Decanoate.

The results shown in FIG. 8 demonstrate that the 7.5:1 mass ratio of Bardac 205M to X-AES, Ethylhexyl-Sulfate (EH-S), 2-Ethylhexanote, Colatrope INC, Octanoate, Marlowet4539, and Decanoate at pH 8 all demonstrated excellent kill properties on *Staphylococcus* no matter the concentration of the quaternary ammonium compound. As noted above, sanitizing quaternary ammonium compounds are not very surface active themselves. The exemplary composition of the present invention, suggests the complexes of quat-anioinc surfactant become radically more surface active, while maintaining antimicrobial efficacy.

Example 9

Solubility of Quaternary Ammonium-Anionic Surfactant Compositions

Compositions of the invention were prepared using a 1 wt. % Bardac 205M solution and a mole:mole ratio of a sulfate-based anionic surfactants or a carboxylate-based anionic surfactant according to the table below and observed appearance behavior in a specimen cup (e.g. precipitation). Each of the resulting combination was observed to determine if a single phase resulted, whether or not the composition was clear or cloudy, and if precipitation occurred. Results are provided in the Table 3.

TABLE 3

| Type of Anionic Surfactant | Anionic Surfactant | Phase | Precipitation/ Type of precipitate | Appearance |
|---|---|---|---|---|
| Sulfate-based | 0.84 wt % SLS | Separated by precipitation | Solid precipitate | Very cloudy |
| Sulfate-based | 0.63 wt % NAS-FAL | Separated by precipitation | Flocculated precipitate | Clear |
| Sulfate-based | 1.2 wt. % SLES | Biphasic | None | Clear with oil phase on top |
| Sulfate-based | 0.68 wt % EH-sulfate | Single | None | Cloudy |
| Sulfate-based | 3.8 wt. % X-AES | Biphasic | None | Clear with oil phase on top |
| Carboxylate-based | 0.5 wt % ethylhexoic acid | Single | None | Slightly cloudy |
| Carboxylate-based | 1.2 wt % Marlowet4539 | Biphasic | None | Clear with oil phase on top |
| Carboxylate-based | 0.5 wt % Colatrope INC | Biphasic | None | Clear with oil phase on top |
| Carboxylate-based | 0.56 wt. % decanoic acid | Single | None | Cloudy |
| Carboxylate-based | 0.5 wt % octanoic acid | Single | None | Cloudy |
| Carboxylate-based | 0.65 wt % lauric acid | Single | Solid | Cloudy |

Example 10

Antimicrobial Efficacy—Suspension Test

Figure 9A:
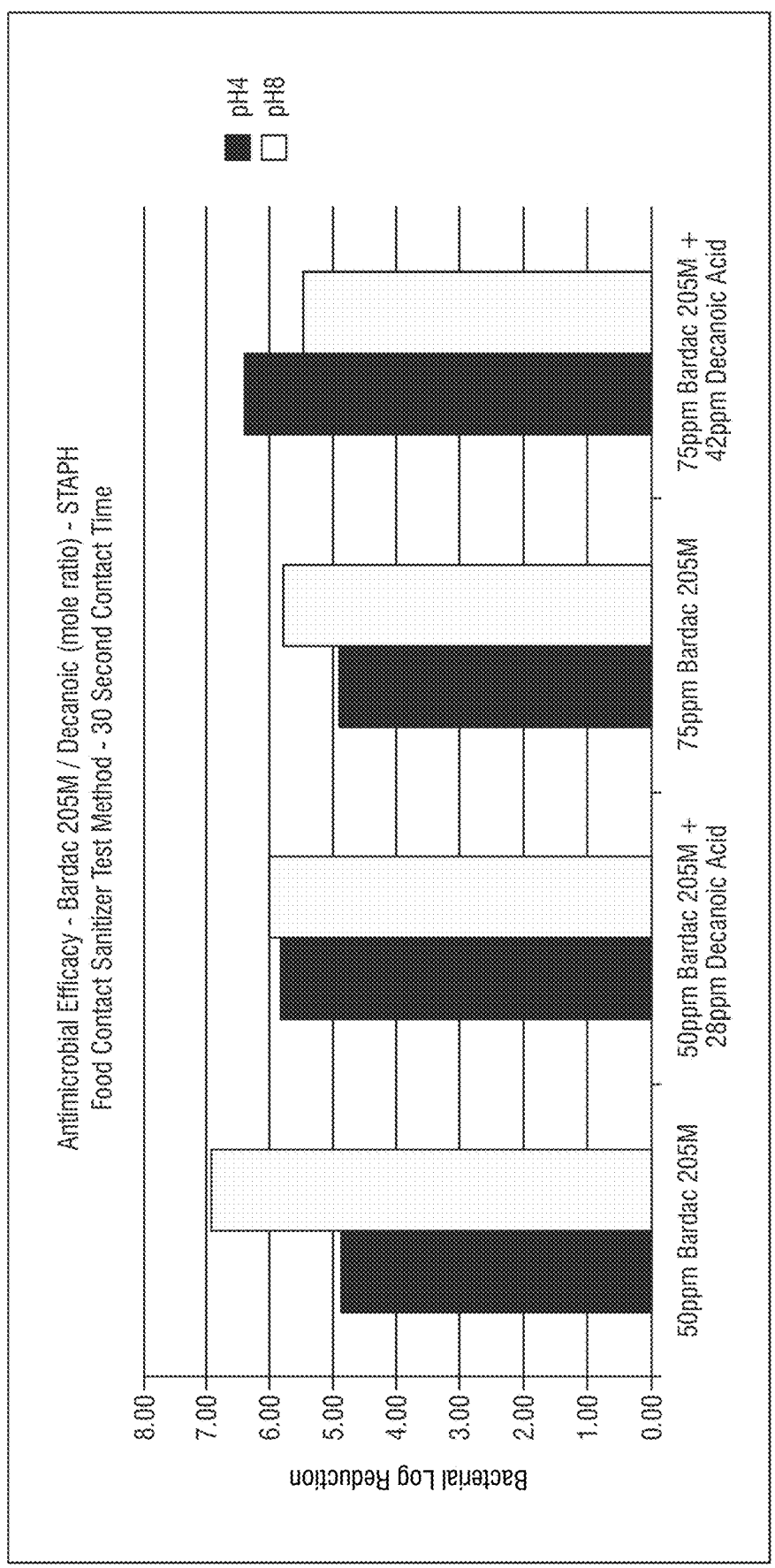
FIG. 9A is a graph illustrating the antimicrobial efficacy of compositions of the invention on *Staphylococcus* at pH 4.0 or pH 8.0.

The antimicrobial efficacy of Bardac 205M—Decanoic acid blend against *Staphylococcus* was assessed using the food contact sanitizer test method at pH 4.0 or pH 8.0 and under the outlined conditions in the tables 4A-4B. The following solutions were examined: 50 ppm Bardac 205M, 50 ppm Bardac 205M+28 ppm Decanoic acid, 75 ppm Bardac 205M, and 75 ppm Bardac 205M+42 ppm Decanoic acid. The results are provided in Table 4C and FIG. 9A.

TABLE 4A

| Test Method: | MS009: Food Contact Sanitizer |
|---|---|
| Test Organisms: | *E. coli* ATCC 11229 |
| Test Substance Diluent: | RTU solutions |
| Exposure Time: | 30 s |
| Exposure Temp: | 25 C. |
| Neutralizer: | 9 ml DE Broth |
| Subculture Medium: | TGE Agar |

TABLE 4B

| Test Systems: | *Pseudomonas aeruginosa* ATCC 15442 (0.206 A @ 620 nm) |
|---|---|
| Test Substance Diluent: | EN Synthetic Hard Water (approx. 375 ppm hardness), pH 6.95 |
| Interfering Substances: | EN Clean Soil Conditions |
| Exposure Time(s): | 5 minutes |
| Neutralizer: | 8 mL Chambers Broth + 1 mL sterile water |
| Test Temperature: | 20° C. |
| Plating Medium: | EN TSA |
| Incubation: | 35° C. for 48 hours |

TABLE 4C

| Organism Inoculum Numbers | Dilution 10e-6 Plate 1 | Dilution 10e-6 Plate 2 | Dilution 10e-7 Plate 1 | Dilution 10e-7 Plate 2 | Average Inoculum (CFU/mL) | Log Avg Inoc- ulum |
|---|---|---|---|---|---|---|
| *Escherichia coli* ATCC 11229 | 36 | 63 | 22 | 2 | 5.6E+07 | 7.75 |
| *Staphylococcus aureus* ATCC 6538 | 71 | 63 | 15 | 7 | 7.1E+07 | 7.85 |
| *Salmonella enterica* ATCC 10708 | 46 | 45 | 14 | 9 | 5.2E+07 | 7.71 |

Figure 9B:
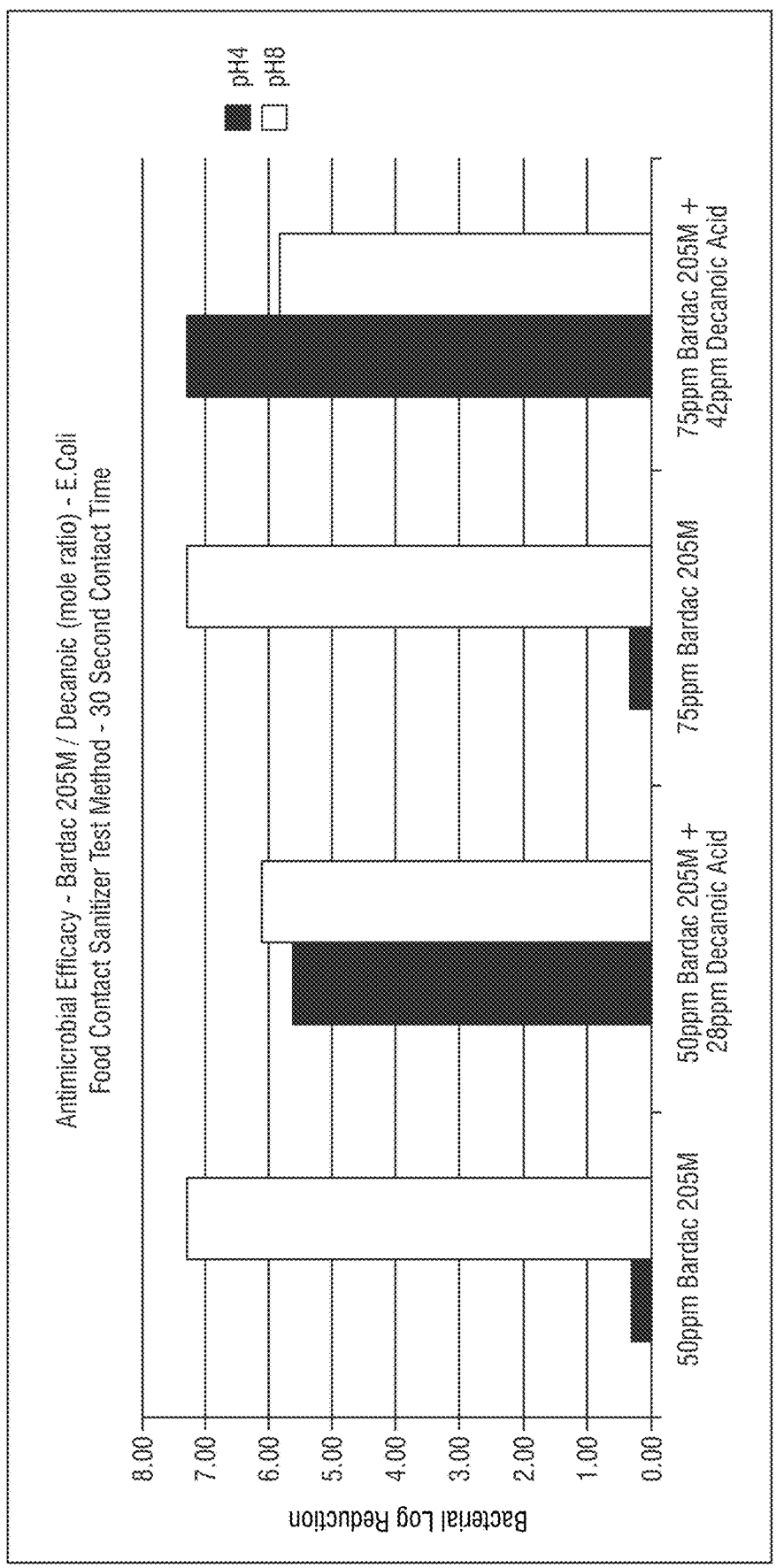
FIG. 9B is a graphical depiction the antimicrobial efficacy of compositions of the invention on *Escherichia coli* at pH 4.0 or pH 8.0.

Another test was preformed using the procedure described above to determine the antimicrobial efficacy of Bardac 205M-Decanoci acid blend against *E. coli*. The following solutions were examined: 50 ppm Bardac 205M, 50 ppm Bardac 205M+28 ppm Decanoic acid, 75 ppm Bardac 205M, and 75 ppm Bardac 205M+42 ppm Decanoic acid. The results are provided in FIG. 9B.

Quaternary ammonium compounds are known to have reduced efficacy in hard water compared to low water hardness conditions (DI, 5 gpg, 17 gpg). Quat/anionic synergy reduces quaternary ammonium concentration requirements for full EPA efficacy and under slightly acidic media (pH-5 and below). Without the presence of water hardness, quat/anionic synergy working at universal pH and at low concentration of quat (sub 50 ppm).

Example 11

Antimicrobial Efficacy-Hard Water

The antimicrobial efficacy of quaternary ammonium compounds and anionic surfactants against *S. aureus* and *E. coli* were evaluated as shown in Table 5A. A water control, 1% Bardac Quat control and 1% Formula #1 provided in Table 5B were examined at pH 7.0.

TABLE 5A

| Organism Inoculum Numbers |
|---|
| *Staphylococcus aureus* ATCC 6538 |
| *Escherichia coli* ATCC 11229 |

TABLE 5B

| Formula #1 | wt % |
|---|---|
| Bardac Quat | 13.75 |
| Decanoic Acid | 2.5 |
| Citric Acid | 30 |
| Water | 53.75 |

The results are provided in the Tables 6-7 below.

TABLE 6

| Sample | Formula | Water Hardness, ppm | Temp | pH | Concentration Quat, ppm Quat Control | Concentration Quat, ppm Formula #1 | Contact Time, sec. | *S. aureus* Survivors (CFU/mL) | *E. coli* Survivors (CFU/mL) | *S. aureus* Log Reduction | *E. coli* Log Reduction |
|---|---|---|---|---|---|---|---|---|---|---|---|
| 1 | Water Control | 250 | 120 F. | 7 | 0 | 0 | 30 | 304e5 | 468e5 | 0.30 | 0.14 |
| 2 | 1% Quat Control | 250 | 120 F. | 7 | 75 |  | 30 | 6e3 | 214e5 | 3.96 | 0.48 |
| 3 | 1% Quat Control | 250 | 120 F. | 7 | 100 |  | 30 | 175e1 | 40e5 | 4.50 | 1.20 |
| 4 | 1% Formula #1 | 250 | 120 F. | 7 |  | 75 | 30 | 345e3 | 252e5 | 2.20 | 0.40 |
| 5 | 1% Formula #1 | 250 | 120 F. | 7 |  | 100 | 30 | 329e1 | 131e5 | 4.22 | 0.69 |

TABLE 7

| Sample | Formula | Water Hardness, ppm | Temp | pH | Concentration Quat, ppm Quat Control | Concentration Quat, ppm Formula #1 | Contact Time, sec. | *S. aureus* Survivors (CFU/mL) | *E. coli* Survivors (CFU/mL) | *S. aureus* Log Reduction | *E. coli* Log Reduction |
|---|---|---|---|---|---|---|---|---|---|---|---|
| 1 | Water Control | 500 | 120 F. | 7 | 0 | 0 | 30 | 384e5 | 320e5 | 0.16 | 0.30 |
| 2 | 1% Quat Control | 500 | 120 F. | 7 | 75 |  | 30 | 101e3 | 368e5 | 2.74 | 0.24 |
| 3 | 1% Quat Control | 500 | 120 F. | 7 | 100 |  | 30 | 13e3 | 111e5 | 3.63 | 0.76 |
| 4 | 1% Formula #1 | 500 | 120 F. | 7 |  | 75 | 30 | 55e3 | 404e5 | 3.00 | 0.20 |
| 5 | 1% Formula #1 | 500 | 120 F. | 7 |  | 100 | 30 | 51e3 | 220e5 | 3.03 | 0.46 |

The results shown in the above Tables 6-7 confirm that when the microbes, especially *E. coli*, are in suspension, they are difficult for quat or quat/anionic blends to kill under hard water, and neutral pH conditions.

An additional test was preformed using the procedure from above, except the pH of the solutions were prepared at pH 7.0 or pH 4.5. The results are provided in Tables 8-9.

TABLE 8

| Sample | Formula | Water Hardness, ppm | pH | Temp | Concentration, ppm Quat | GLDA | Builder Citric Acid | Contact Time, sec | E. coli Survivors (CFU/mL) | E. coli Log Reduction |
|---|---|---|---|---|---|---|---|---|---|---|
| 7 | Bardac LF80 | 500 | 7.0 | 120 F. | 100 | | | 30 | 130e3 | 2.71 |
| 8 | Bardac LF80 | 500 | 4.5 | 120 F. | 100 | | | 30 | 50e1 | 5.15 |
| 9 | Sanitizing Formula #1 | 500 | 7.0 | 120 F. | 100 | 50 | | 30 | 243e3 | 0.46 |
| 10 | Sanitizing Formula #1 | 500 | 4.5 | 120 F. | 100 | 50 | | 30 | 1e1 | >6.85 |
| 11 | Sanitizing Formula #1 | 500 | 7.0 | 120 F. | 100 | | 50 | 30 | 154e3 | 2.66 |
| 12 | Sanitizing Formula #1 | 500 | 4.5 | 120 F. | 100 | | 50 | 30 | <1e1 | >6.85 |

TABLE 9

| Sample | Formula | Water Hardness, ppm | pH | Temp | Concentration, ppm Quat | Decanoic Acid | Contact Time, sec | E. coli Survivors (CFU/mL) Rep 1 | E. coli Survivors (CFU/mL) Rep 2 | E. coli Log Reduction |
|---|---|---|---|---|---|---|---|---|---|---|
| 7 | Bardac LF80 | 500 | 4.5 | 120 F. | 100 | | 30 | 375e1 | 164e1 | 4.27 |
| 8 | Bardac LF80 | 500 | 4.5 | 120 F. | 75 | | 30 | 47e5 | 56e5 | 0.99 |
| 9 | Bardac LF80 | 500 | 4.5 | 120 F. | 50 | | 30 | 272e5 | 200e5 | 0.33 |
| 10 | Sanitizing Formula #1 | 500 | 4.5 | 120 F. | 100 | 25 | 30 | 1e1 | 1e1 | >6.41 |
| 11 | Sanitizing Formula #1 | 500 | 4.5 | 120 F. | 75 | 18.75 | 30 | 1e1 | 1e1 | >6.41 |
| 12 | Sanitizing Formula #1 | 500 | 4.5 | 120 F. | 50 | 12.5 | 30 | 264e1 | 26e3 | 3.54 |

The results shown in Tables 8-9 show that the water hardness issue in suspension test is overcome by bringing the pH slightly acidic (pH about 4.5). The lower pH helps the quat/decanoic more than the quat alone. Even with 500 ppm water hardness, the efficacy of the quat/decanoic is radically improved at pH 4.5 compared to pH 7.0, demonstrating a synergistic quat/decanoic provides complete kill at 75 ppm quat level compared with less than 5 log kill (fail to sanitize) for 100 ppm quat alone.

Example 12

Third Sink Sanitizer

The antimicrobial efficacy of quaternary ammonium compounds and anionic surfactants for use as a third sink sanitizer were evaluated as shown in Table 10.

TABLE 10

Experimental 3$^{rd}$ Sink Formula

| Formula | wt % |
|---|---|
| Bardac Quat | 7.5 |
| Decanoic Acid | 0.5 |
| Citric Acid | 15 |
| Water | 77 |

The results are provided in Table 11 below.

| Sample | Water Hardness, ppm | pH | Concentration, ppm Quat | Decanoic Acid | Emulsogen CNO | Contact time, sec | S. aureus Survivors (CFU/mL) | E. coli Surivivors (CFU/mL) | S. aureus Log Reduction | E. coli Log Reduction |
|---|---|---|---|---|---|---|---|---|---|---|
| 1 | 500 | 7.0 | 200 | 0 | 0 | 30 | 46e1 | 1e1 | 5.06 | 6.81 |
| | | | | | | 60 | 1e1 | 1e1 | 6.72 | 6.81 |
| 2 | 500 | 4.5 | 200 | 0 | 0 | 30 | 1e1 | 1e1 | 6.72 | 6.81 |
| | | | | | | 60 | 1e1 | 1e1 | 6.72 | 6.81 |
| 3 | 500 | 7.0 | 200 | 75 | 0 | 30 | 12e1 | 256e5 | 5.64 | 0.40 |
| | | | | | | 60 | 1e1 | 312e5 | 6.72 | 0.31 |

-continued

| Sample | Water Hardness, ppm | pH | Quat | Concentration, ppm Decanoic Acid | Emulsogen CNO | Contact time, sec | S. aureus Survivors (CFU/mL) | E. coli Surivirors (CFU/mL) | S. aureus Log Reduction | E. coli Log Reduction |
|---|---|---|---|---|---|---|---|---|---|---|
| 4 | 500 | 4.5 | 200 | 75 | 0 | 30 | 1e1 | 5e1 | 6.72 | 6.11 |
|   |     |     |     |    |   | 60 | 1e1 | 1e1 | 6.72 | 6.81 |
| 5 | 500 | 7.0 | 200 | 0  | 75 | 30 | 1e1 | 59e1 | 6.72 | 5.04 |
|   |     |     |     |    |    | 60 | 1e1 | 1e1 | 6.72 | 6.81 |
| 6 | 500 | 4.5 | 200 | 0  | 75 | 30 | 1e1 | 1e1 | 6.72 | 6.81 |
|   |     |     |     |    |    | 60 | 1e1 | 1e1 | 6.72 | 6.81 |
| 7 | 500 | 7.0 | 200 | 75 | 75 | 30 | 7e1 | 532e5 | 5.87 | 0.08 |
|   |     |     |     |    |    | 60 | 1e1 | 340e5 | 6.72 | 0.28 |
| 8 | 500 | 4.5 | 200 | 75 | 75 | 30 | 1e1 | 39e1 | 6.72 | 5.22 |
|   |     |     |     |    |    | 60 | 16e1 | 16e1 | 5.51 | 6.81 |

These results confirm that under 500 ppm water hardness condition, decanoate (anionic form at neutral pH) "deactivates" quat, while decanoic acid (protonated form at pH 4.5) "synergizes" the quat. However, alcohol ethoxy carboxylate (Emulsogen CNO) does not deactivate the quat under neutral pH. Without being bound by theory, we believe at neutral pH, the carboxyl groups on the outer wall of microbes such as E. coli are the main attraction sites for quat (opposite charge attraction). However, the water hardness cations ($Ca^{++}$ and $Mg^{++}$) are even more attracted to them, effectively "blocking" the quaternary ammonium compounds. The quat/carboxylic combinations according to the invention provide still further inactivation since the decanoate can be attracted to the $Ca^{++}$ and $Mg^{++}$ that are attached to the microbe outer walls, making them more hydrophobic (e.g. similar to soap scum). In an aspect, this further confirms why alcohol ethoxy carboxylates fare better than decanoate as they are not prone to form lime soaps. However, when pH is lowered to about 4.5, some of the carboxyl groups on the outer wall of the microbes are protonated, opening them to quat, and even more so to the quat/decanoic which is radically more surface active.

Example 13

Food Contact Sanitizing—Hard Water pH Study

Additional testing was done analyzing the antimicrobial efficacy of the Quat-Anioinc surfactant blend in various pH conditions. The compositions according to the invention (and control without both the quaternary ammonium compound and anionic surfactant) and results are provided in Tables 12-13.

TABLE 12

| Sample | Formula | Water Hardness, ppm | pH | Temp | Concentration Quat ppm | Anionic ppm | Contact Time, sec | E. coli Survivors CFU/mL | E. coli Log Reduction |
|---|---|---|---|---|---|---|---|---|---|
| 1 | Bardac 205M | 500 | 7.0 | 77 F. | 200 |    | 30 | <1e1 | >6.85 |
| 2 | Bardac 205M + DA | 500 | 7.0 | 77 F. | 200 | 75 | 30 | 28e5 | 1.40 |
| 3 | Bardac 205M + DA | 500 | 6.5 | 77 F. | 200 | 75 | 30 | 34e5 | 1.31 |
| 4 | Bardac 205M + DA | 500 | 6.0 | 77 F. | 200 | 75 | 30 | 36e5 | 1.29 |
| 5 | Bardac 205M + DA | 500 | 5.5 | 77 F. | 200 | 75 | 30 | >300e5 | NA |
| 6 | Bardac 205M+ | 500 | 5.0 | 77 F. | 200 | 75 | 30 | 21e1 | 5.52 |

These data pinpoint the pH cut off at approximately pH of 5.

TABLE 13

| Sample | Formula | Water Hardness, ppm | pH | Temp | Concentration Quat ppm | Anionic ppm | Contact Time, sec | E. coli Survivors (CFU/mL) Rep1 | E. coli Survivors (CFU/mL) Rep2 | E. coli Log Reduction |
|---|---|---|---|---|---|---|---|---|---|---|
| 1 | Quat 2080 | 500 | 4.3 | 77 F. | 75 |   | 30 | 44e5 | 3e5 | 1.33 |
| 2 | Quat 2080 + DA | 500 | 4.6 | 77 F. | 75 | 12.5 | 30 | 1e1 | 18e1 | 5.72 |

These data clearly showed the quat/decanoic synergy at acidic pH at lower quat level.

Example 14

Hard Surface Sanitizing—Hard Water pH Study

Additional testing was done analyzing the antimicrobial efficacy of the Quat-Anioinc surfactant blend in various pH conditions with hard water. The compositions (and control without both the quaternary ammonium compound and anionic surfactant), evaluated conditions and results are provided in Tables 14-18.

TABLE 14

| Inoculum Numbers (CFU/mL) | Plate 1 | Plate 2 | Average |
|---|---|---|---|
| *Escherichia coli* ATCC 11229 | 125e6 | 168e6 | 1.50E+08 |

TABLE 15

| Sanitizing Formula #1 | |
|---|---|
| Material | Wt % |
| Bardac LF80 | 13.75 |
| Decanoic Acid | 2.5 |
| Emulsogen CNO | 4 |
| Plurafac SLF180 | 11 |
| HEDP, 60% | 2.7 |
| DI Water | 66.05 |

TABLE 16

| Sanitizing Formula #2 | |
|---|---|
| Material | Wt % |
| Bardac LF80 | 13.75 |
| NAS-FAL | 3.5 |
| Emulsogen CNO | 4 |
| Plurafac SLF180 | 11 |
| HEDP, 60% | 2.7 |
| DI Water | 65.05 |

TABLE 17

| | | | | | | | |
|---|---|---|---|---|---|---|---|
| | | Swabs from glasses: | | | | | |
| Test | Test Substance | Rinse Volume | Rinse Temp. | CFU/mL | CFU/swab (CFU/mL × 5) | Log10 Growth | Log10 Reduction |
| 1 | 50 ppm Formula #1 | 1.7 gal/rack | 118-120° F. | 107e0 | 5.4E+02 | 2.73 | 3.38 |
| | | | | <1e0 | <5 | <0.70 | >5.41 |
| 2 | 100 pppm Formula #1 | | | <1e0 | <5 | <0.70 | >5.51 |
| | | | | <1e0 | <5 | <0.70 | >5.51 |
| 3 | 50 ppm Formula #2* | | | 50e2 | 2.5E+04 | 4.40 | 1.92 |
| | | | | 16e0 | 8.08E+01 | 1.90 | 4.42 |
| 4 | 100 pppm Formula #2 | | | <1e0 | <5 | <0.70 | >5.62 |
| | | | | <1e0 | <5 | <0.70 | >5.62 |
| | Untreated Control Counts | | 1 | 25e4 | 1.3E+06 | 6.11 | NA |
| | | | 2 | 32e4 | 1.6E+06 | 6.20 | NA |
| | | | 3 | NT | NT | NT | NA |
| | | | 4 | 41e4 | 2.10E+06 | 6.32 | NA |
| | Swab from Uninoculated Control Glass | | | <1e0 | <5 | <0.70 | NA |

TABLE 18

| | | | | | | |
|---|---|---|---|---|---|---|
| | | Sampling from the sump: | | | | |
| Test | Test Substance | Rinse Volume | Rinse Temp. | CFU/mL | CFU/sample (CFU/mL × 5) | Log10 Growth |
| | | *Escherichia coli* ATCC 11229 | | | | |
| 1 | 50 ppm Formula #1 | 1.7 gal/rack | 118-120° F. | <1e0 | <5 | <0.70 |
| 2 | 100 ppm Formula #1 | | | <1e0 | <5 | <0.70 |
| 3 | 50 ppm Formula #2 | | | <1e0 | <5 | <0.70 |

As shown in Tables 17-18 the unexpected results show that even at very hard water condition (15 grains per gallon, or 2565 ppm water hardness) the combination of the quat/anionic compositions, as shown the quat/decanoic, provides 5 log kill of the more challenging *E. coli*, at as low as 50 ppm di-octyl quat level. This confirms that quat/anionic is very efficacious vs. microbes that are deposited on hard surfaces, even under very hard water condition, and at pH neutral or above. The sampling from the sump confirms that the microbes are killed, not just removed from the surfaces.

Example 15

High Foaming Non-Molar Ratio Study

Additional testing was done analyzing non-molar ratios of the compositions on the present invention. The evaluated compositions, conditions and results are provided in Table 19.

TABLE 19

| Sample | Water Hardness, ppm | pH | Concentration, ppm | | | | Contact Time, sec | E. coli Survivors (CFU/mL) | E. coli Log reduction |
|---|---|---|---|---|---|---|---|---|---|
| | | | Quat | Decanoic Acid | NAS-FAL | Emulsogen CNO | | | |
| 1 | 500 | 7 | 200 | 0 | | | 30 | 1e1 | 7.01 |
| | | | | | | | 15 | 1e1 | 7.01 |
| 2 | 500 | 4.5 | 200 | 0 | | | 30 | 1e1 | 7.01 |
| | | | | | | | 15 | 1e1 | 7.01 |
| 3 | 500 | 7 | 200 | 25 | | | 30 | 56e1 | 5.26 |
| | | | | | | | 15 | 39e3 | 3.42 |
| 4 | 500 | 4.5 | 200 | 25 | | | 30 | 1e1 | 7.01 |
| | | | | | | | 15 | 1e1 | 7.01 |
| 5 | 500 | 7 | 200 | 10 | | | 30 | 1e1 | 7.01 |
| | | | | | | | 15 | 43e1 | 5.37 |
| 6 | 500 | 4.5 | 200 | 10 | | | 30 | 1e1 | 7.01 |
| | | | | | | | 15 | 1e1 | 7.01 |
| 7 | 500 | 7 | 200 | | 25 | | 30 | 27e1 | 5.58 |
| | | | | | | | 15 | 7e1 | 6.16 |
| 8 | 500 | 4.5 | 200 | | 25 | | 30 | 7e1 | 6.16 |
| | | | | | | | 15 | 13e1 | 5.89 |
| 9 | 500 | 7 | 200 | | | 50 | 30 | 1e1 | 7.01 |
| | | | | | | | 15 | 22e1 | 5.67 |
| 10 | 500 | 4.5 | 200 | | | 50 | 30 | 1e1 | 7.01 |
| | | | | | | | 15 | 158e1 | 4.81 |

These results confirm the molar ratios according to compositions of the invention, namely that many non-molar quat/anionic combos (more quat than anionic) pass the 500 ppm water hardness suspension tests at both neutral and acidic pH. However, the further the compositions are from a molar ratio, the surface activity benefit becomes less and less demonstrating the trade-off of pH dependence vs. desired surface activity/wetting.

Example 16

Dynamic Surface Tension of Bardac LF80 and Anionic Polymers

The SITA science line t60 measures the dynamic surface tension of liquids up to the semi-static range. Air bubbles are generated from a capillary with known radius. The bubble pressure is measured as a function of bubble life time, which can be correlated to the surface tension according to the Young-Laplace equation. Dynamic surface tension provides insight in to the dynamic behavior of surfactants and other surface active compounds under dynamic conditions, i.e. how quick surfactants can reach a surface. The dynamic surface tension behavior of surfactants is particularly important in applications where a quick response of surfactant is required, for example, in short rinse cycles of automated dishwashing.

Apparatus and Materials
1. SITA T60 (Sita Messtechnik, Germany)
2. Oil bath with stir bar
3. Heating and stirring plate
4. Glass beakers
5. Glass vials (20 mL)

The SITA science line t60 was calibrated with DI water. Clean water samples after calibration should have a surface tension of 72.0±1.0 mN/m (depending on the quality and temperature). Following calibration, the SITA was programmed to take readings at the desired time intervals (i.e., 0.3, 1.6, 3.0, 9.1 seconds). In order to determine the effects on the dynamic surface tension of Bardac LF80 and varying concentrations of Acusol 445 the following five solutions were analyzed at pH 7.0; 100 ppm Bardac LF80; 10 ppm Acusol 445; 100 ppm Bardac LF80+10 ppm Acusol 445; 100 ppm Bardac LF80+30 ppm Acusol 445; and 100 ppm Bardac LF80+75 ppm Acusol 445.

10-15 mL were transferred into 20 mL vials and immersed in a heated oil bath to 72° C. (160° F.)±2° C. The samples were equilibrated for 10-15 minutes. The samples were individually removed from the oil bath and tested in the SITA. After each sample was tested the SITA's cleaning procedure was run, then the surface tension of DI water was checked to ensure the SITA was adequately clean. If the DI water measurements were not within 72.0±1.0 mN/m, then the cleaning procedure was run again. The surface tension (mN/m) versus bubble life time at 160° F. was recorded and shown in FIG. 10.

The data from these experiments demonstrate Bardac LF80 itself shows slow dynamic surface activity. Likewise, Acusol 445 alone shows very little surface activity. However, the combination of Bardac LF80 and Acusol 445 are more dynamically active than either of the individuals. Furthermore, increasing synergy between Bardac LF80 and increasing levels of Acusol 445 can be seen, but the synergy levels off between 30 ppm and 75 ppm of Acusol 445.

Further testing of the dynamic surface activity was preformed to assess the synergy of other Bardac LF80 and polymer combinations. According to the procedure outlined above, the surface activity of the following five solutions at pH 7.0 were determined; 100 ppm Bardac LF80; 100 ppm Bardac LF80+75 ppm PSO; 100 ppm Bardac LF80+75 ppm Acusol 445; and 100 ppm Bardac LF80+75 ppm AR-801. These results are provided in FIG. 11.

Figure 10:
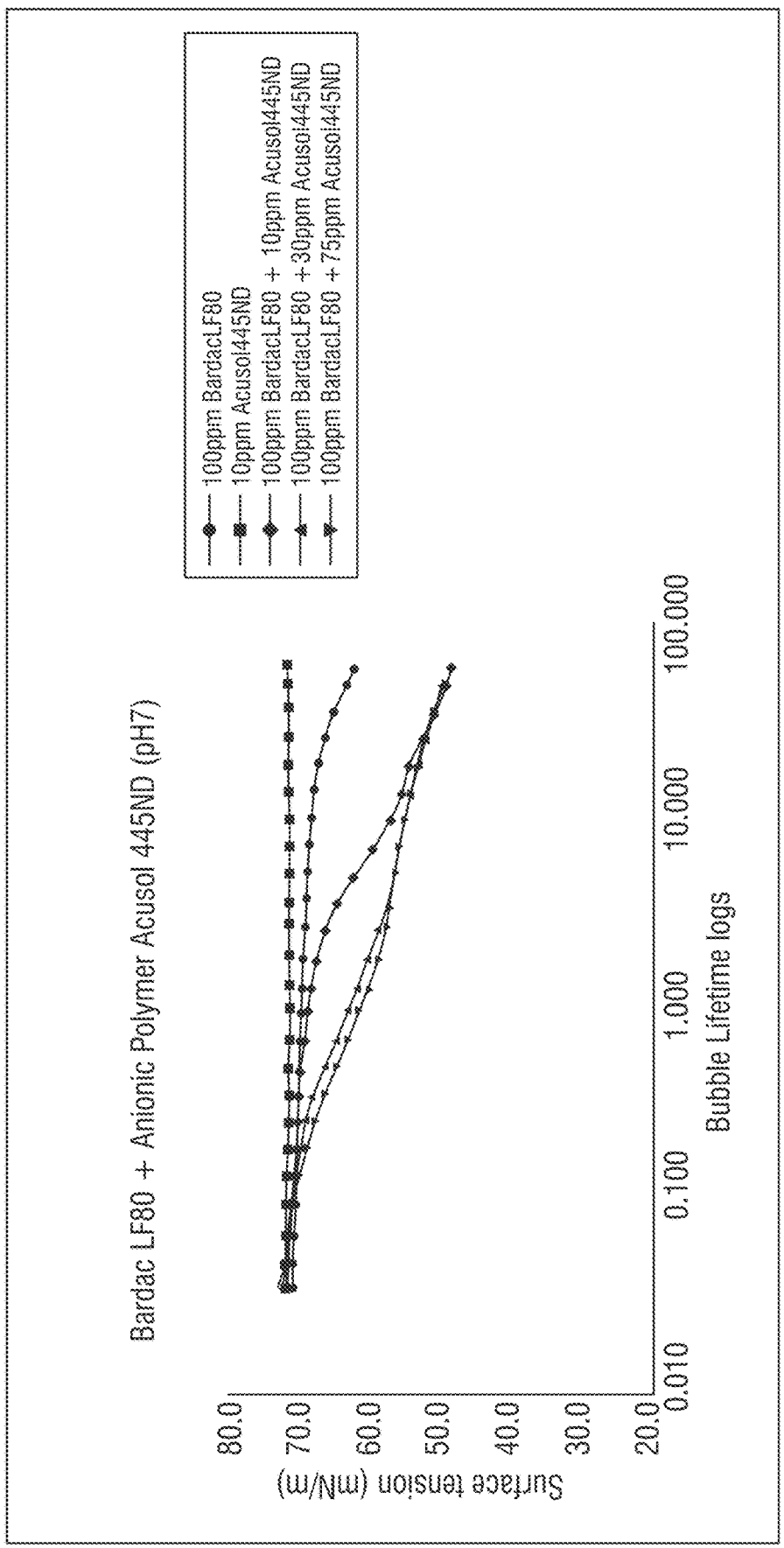
FIG. 10 shows a graphical representation of the average dynamic surface tension of Bardac LF80 and anionic polymers as described in Example 16.
Figure 11:
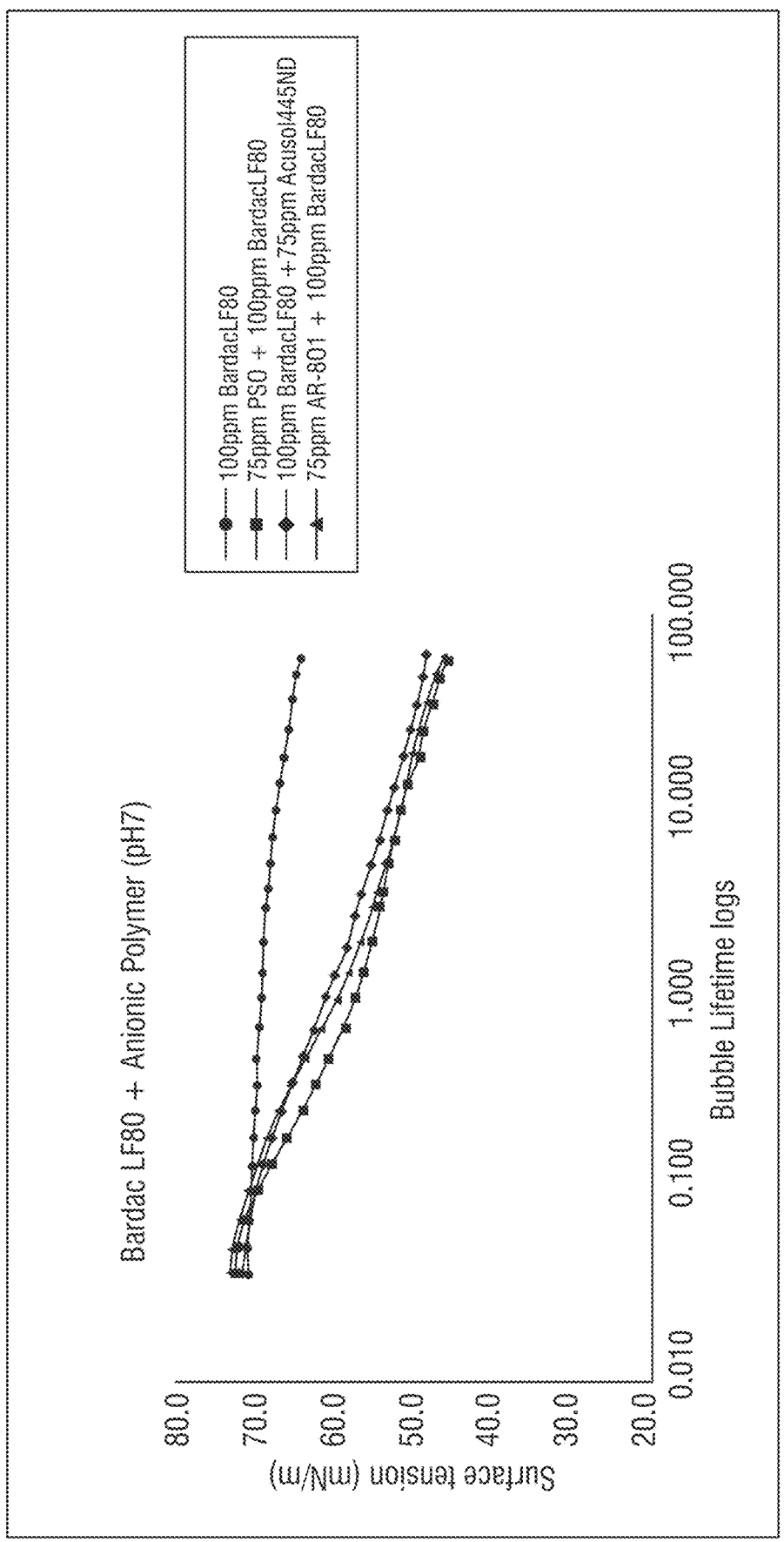
FIG. 11 shows a graphical depiction of the average dynamic surface tension of Bardac LF80 and varying concentrations of polymer at pH 7.0 as described in Example 16.
Figure 12:
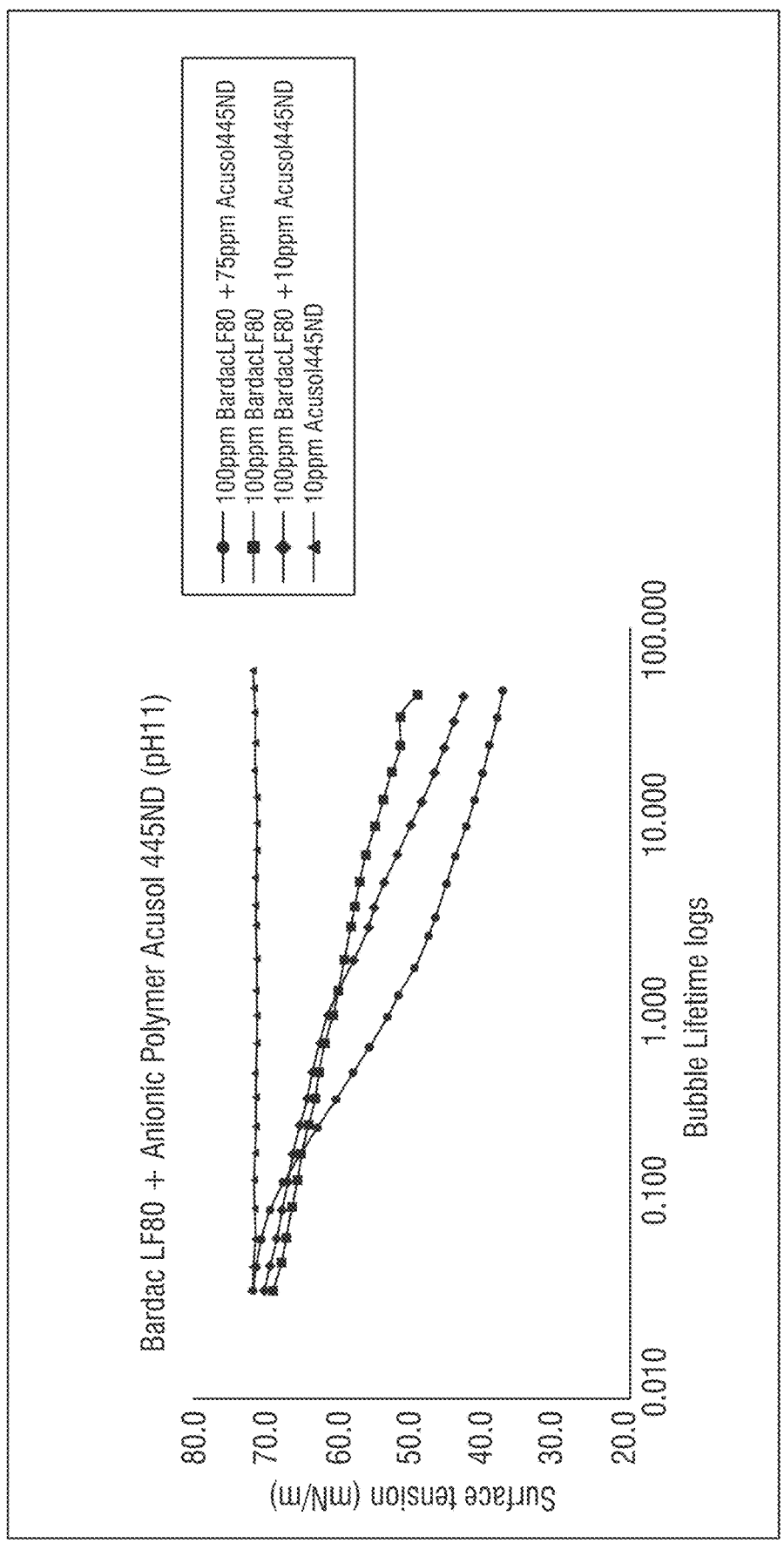
FIG. 12 shows a graph of the average dynamic surface tension of Bardac LF80 and varying concentrations of polymer at pH 11 as described in Example 16.

Consistent with the results provided in FIG. 10, the data in FIG. 11 clearly shows synergy between Bardac LF80 and the anionic polymers tested (Acusol 445, PSO, and AR-801). The Quat-Anionic polymer solutions increased the dynamic surface activity compared to the Quat solution alone. All three polymers at the concentrations tested were able to increase the dynamic surface activity of Bardac LF80 at comparable rates.

In order to determine if the observed boost in surface activity in Bardac LF80-Anioninc polymer solutions was dependent on pH the following solutions were tested according to the procedure above at pH 11.0; 100 ppm Bardac LF80; 10 ppm Acusol 445; 100 ppm Bardac LF80+10 ppm Acusol 445; 100 ppm Bardac LF80+75 ppm Acusol 445. The results of this experiment are provided in FIG. 123.

As can be seen by this data, a change to pH 11.0 has no observable influence on the surface activity of Acusol 445 alone. While, the surface activity of Bardac LF80 alone appears to be increased at pH 11.0 when viewed in combination with the results of FIG. 11. However, synergy between the anionic polymer and quat is still observed indicating that the synergistic increase in surface activity is independent of pH.

Example 17

Dynamic Surface Tension of Quat and Anionic Polymers

Figure 13:
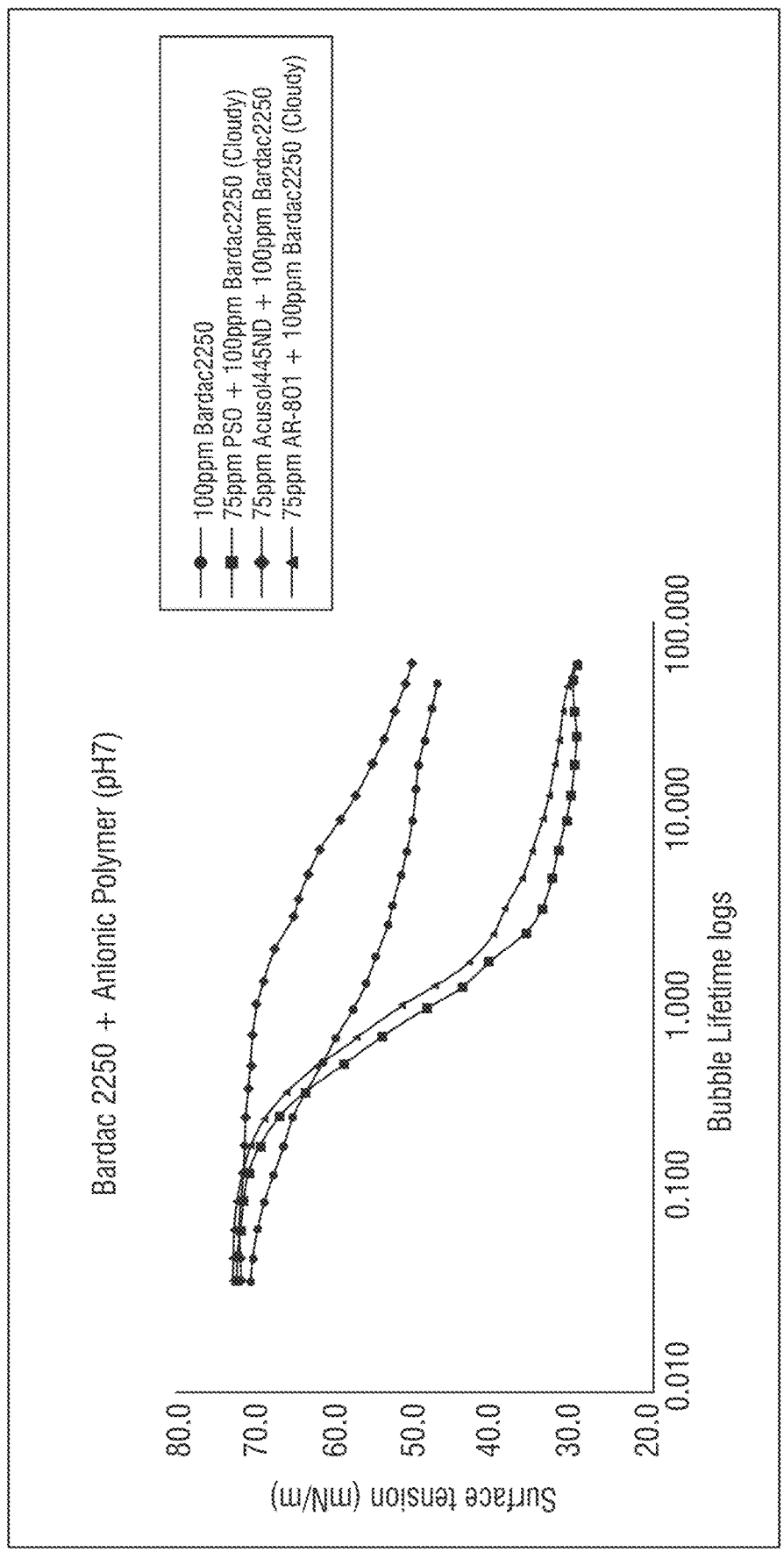
FIG. 13 is a graphical representation of the average dynamic surface tension of Bardac 2250 and Anionic polymers as described in Example 17.

Investigation of the dynamic surface tension of Quat-Anionic polymer pairs continued as described in Example 16 at pH 7.0 for the following solutions; 100 ppm Bardac 2250; 100 ppm Bardac 2250+75 ppm PSO; 100 ppm Bardac 2250+75 ppm Acusol 445; 100 ppm Bardac 2250+75 ppm AR-801. The data from this experiment is provided in FIG. 13. The results in FIG. 13 show a radical difference for Bardac 2250 when viewed in combination with the data from FIG. 10, demonstrating different in surface activity between a C10 versus C8 quaternary ammonium compound in combination with the anionic polymer. While Bardac 2250 appears to be synergized by the smaller PSO and AR-801, it is clear that it becomes in-activated by the larger anionic polymer Acusol 445.

Figure 14:
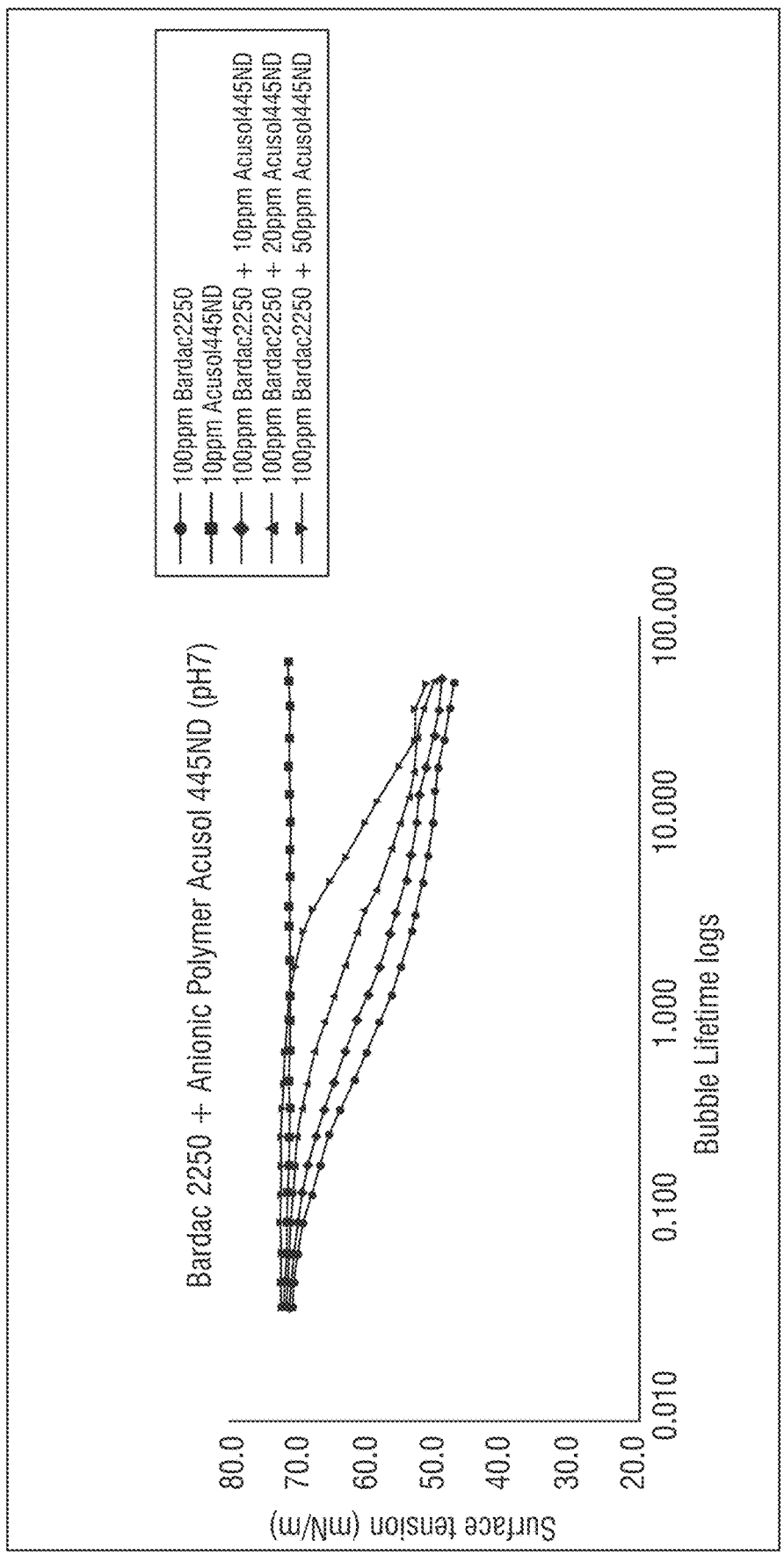
FIG. 14 is a graphical depiction of the average dynamic surface tension of Bardac 2250 and varying concentrations of polymer at pH 7.0 as described in Example 17.

To further test the in-activation of Bardac 2250 by Acusol 445 the procedure from Example 16 was used for the following solutions at pH 7.0; 100 ppm Bardac 2250; 10 ppm Acusol 445; 100 ppm Bardac 2250+10 ppm Acusol 445; 100 ppm Bardac 2250+20 ppm Acusol 445; and 100 ppm Bardac 2250+50 ppm Acusol 445. The results are provided in FIG. 14. As can be seen from this data Acusol 445 shows a dose-dependent in-activation of Bardac 2250 in regards to dynamic surface activity. As the concentration of Acusol 445 increases the rate at which the surface tension decreases for Bardac 2250 over the bubble lifetime is decreased.

Figure 15:
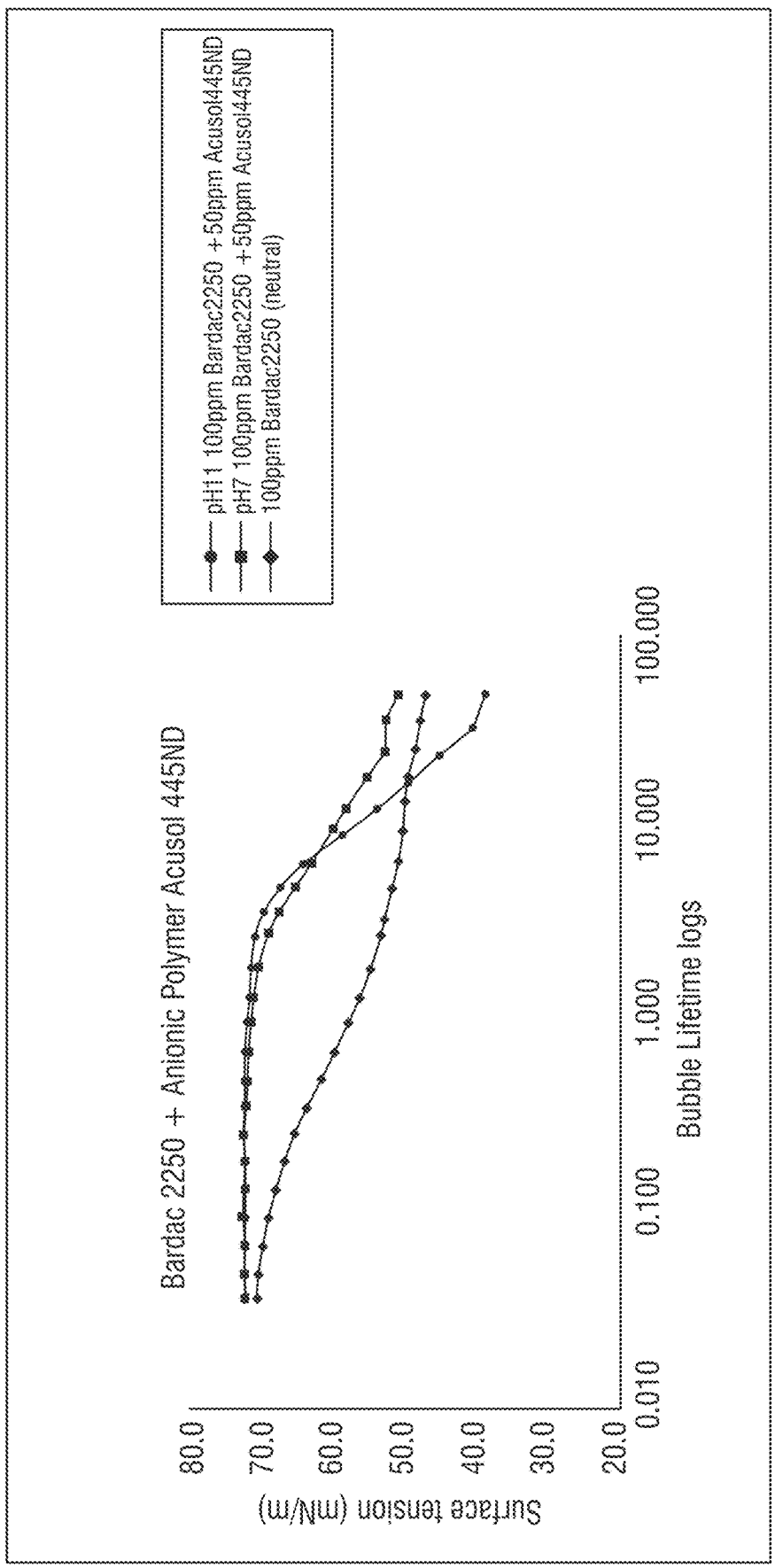
FIG. 15 is a graph showing the average dynamic surface tension of Bardac 2250 and varying concentrations of polymer at pH 11 and pH 7.0 as described in Example 17.

In order to determine if the Acusol 445 mediated in-activation of Bardac 2250 dynamic surface tension is dependent on the pH of the solution, further testing according to the procedure outlined in Example 16 was used except the solutions at a pH 7.0 and pH 11.0 were compared side-by-side. Specifically, the following three solutions were analyzed; 100 ppm Bardac 2250; 100 ppm Bardac 2250+50 ppm Acusol 445 at pH 7.0; and 100 ppm Bardac 2250+50 ppm Acusol 445 at pH 11.0. The results are provided in FIG. 15. The data demonstrates the in-activation of Bardac 2250 by Acusol 445 is maintained at pH 11.0. The surface tension of the solutions of Bardac 2250 in combination with Acusol 445 decrease at comparable rates regardless of pH. While the surface tension of Bardac 2250 alone decreases quickly over the bubble lifetime.

Figure 16:
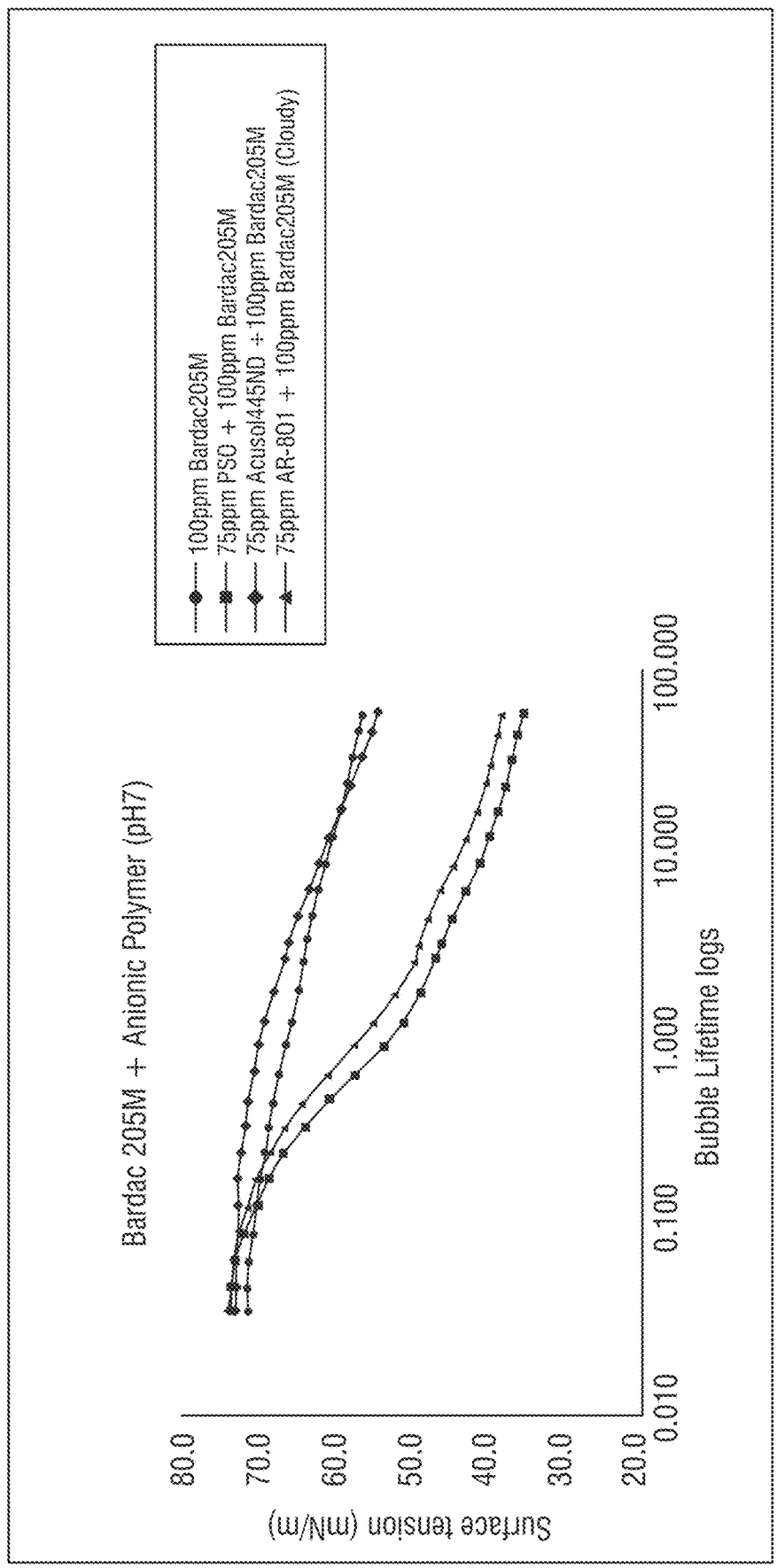
FIG. 16 shows a graphical representation of the average dynamic surface tension of Bardac 205M and anionic polymers as described in Example 17.
Figure 17:
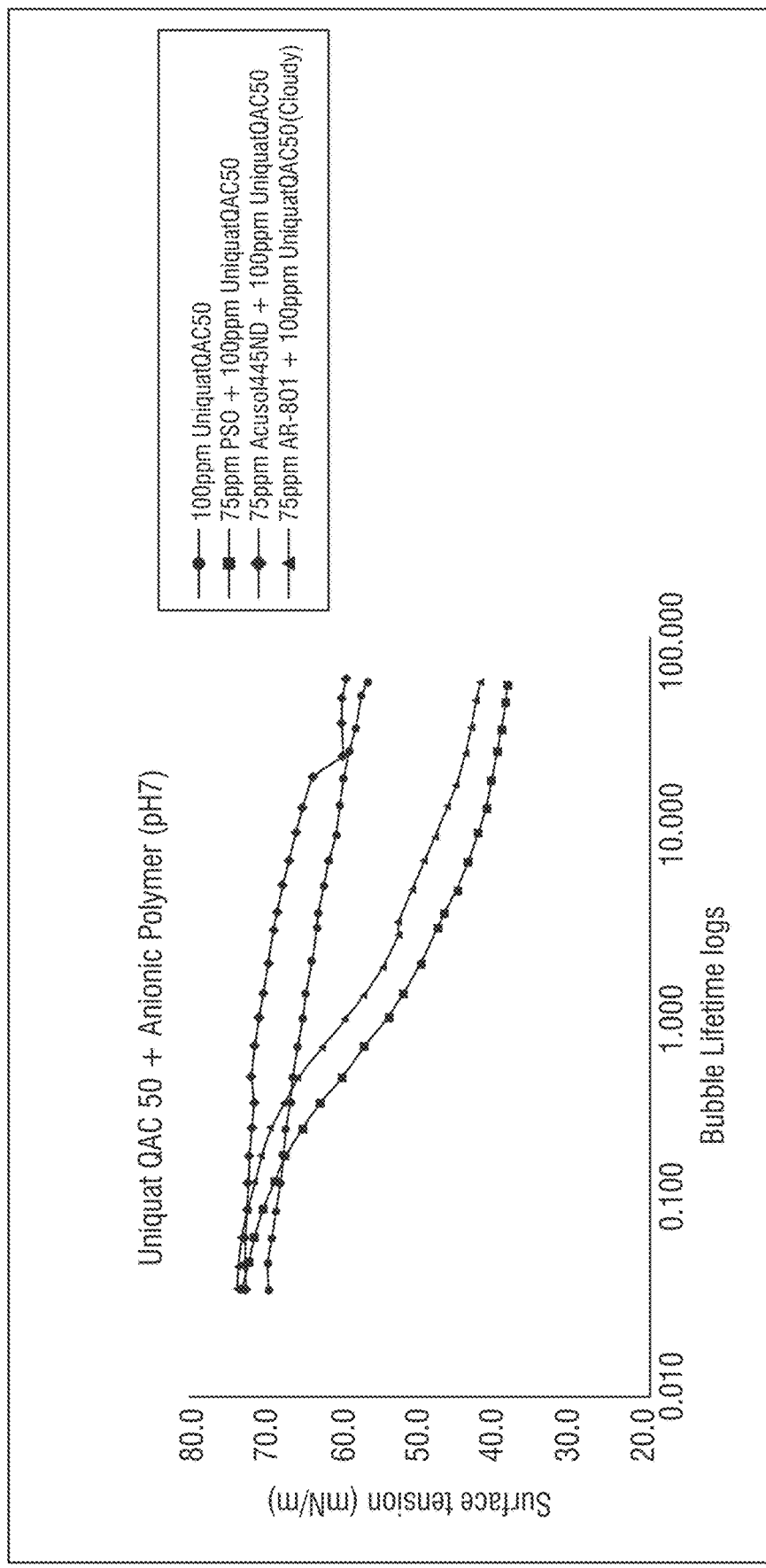
FIG. 17 shows a graphical depiction of the average dynamic surface tension of Uniquat QAC50 and anionic polymers as described in Example 17.

The dynamic surface tension of Quat-Anionic polymer pairs was further evaluated using the procedure described in Example 16 to assess the impact of a combination of C8-C10 quaternary ammonium compounds has on activation or in-activation. For these experiments the following solutions were prepared at pH 7.0; 100 ppm Bardac 205M; 100 ppm Bardac 205M+75 ppm PSO; 100 ppm Bardac 205M+75 ppm Acusol 445; and 100 ppm Bardac 205M+75 ppm AR-801 (FIG. 16) or 100 ppm Uniquat QAC50; 100 ppm Uniquat QAC50+75 ppm PSO; 100 ppm Uniquat QAC50+75 ppm Acusol 445; and 100 ppm Uniquat QAC50+75 ppm AR-801 (FIG. 17). The data examining Bardac 205M-Anionic polymer pairs are provided in FIG. 16 and the results of Uniquat QAC50-Anioinc polymer pairs are provided in FIG. 17.

Consistent with the results of FIG. 13, the mixture of Bardac 205M is also synergized by the smaller anionic polymers, PSO and AR-801. As both PSO and AR-801 in combination with Bardac 205M display a decrease in dynamic surface tension compared to Bardac 205M alone. While the larger anionic polymer, Acusol 445, had an in-activating effect on the dynamic surface tension of Bardac 205M, albeit mildly in-activating compared to FIG. 13. Moreover, the Uniquat QAC50 solutions followed a similar trend, where the smaller anionic polymers, PSO and AR-801 show synergistic surface activity. However, the mixture of Acusol 445 and Uniquat QAC50 show mildly in-activated surface activity (FIG. 17).

The results of Example 16 and Example 17, when viewed in combination, show that Bardac LF80 (C8) and anionic polymer combinations display synergistic surface activity boosting properties independent of pH or polymer size. Whereas, Bardac 2250, Bardac 205M, and Uniquat QAC50, also show synergistic surface activity boosting effects when mixed with the smaller anionic polymers (PSO and AR-801) but show antagonistic trends (i.e. in-activation) as a function of polymer concentration and pH when mixed with the larger anionic polymer, Acusol 445.

Example 18

Dynamic Surface Tension of Quat-Chelant Solutions

Figure 18:
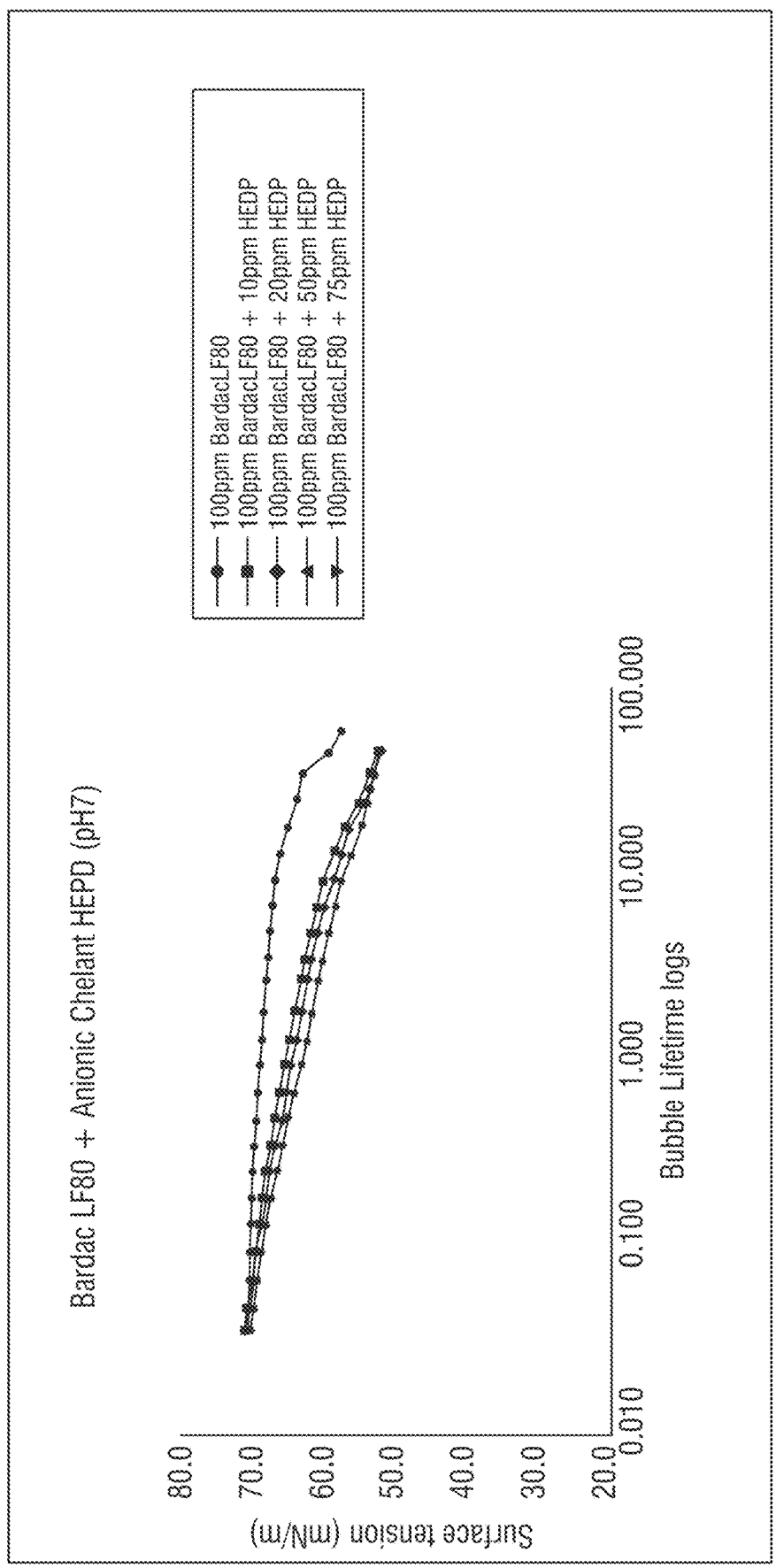
FIG. 18 is a graphical representation of the average dynamic surface tension of Bardac LF80 and anionic chelant HEDP at varying concentrations as described in Example 18.

Using the SITA science line t60 system and the procedure described in Example 16, combinations of Quat-Anionic chelant solutions were analyzed. Specifically, the following solutions were analyzed at pH 7.0; 100 ppm Bardac LF80; 100 ppm Bardac LF80+10 ppm HEDP; 100 ppm Bardac LF80+20 ppm HEDP; 100 ppm Bardac LF80+50 ppm HEDP; and 100 ppm Bardac LF80+75 ppm HEDP. These results are shown in FIG. 18. These results indicate an increase in dynamic surface activity of Bardac LF80 in combination with HEDP. The synergistic trend appears to be a function of chelant concentration, although this is a subtle trend.

Additional Quaternary ammonium compounds were tested in combination with anionic chelants according to the procedure outlined in Example 16. The following solutions were prepared to be tested; 100 ppm Bardac 2250; 100 ppm Bardac 2250+75 ppm Dequest 2000; and 100 ppm Bardac 2250+75 ppm Trilon M (FIG. 19) or 100 ppm Uniquat QAC50; 100 ppm Uniquat QAC50+75 ppm Dequest 2000; and 100 ppm Uniquat QAC50+75 ppm Trilon M (FIG. 20). The results from the Bardac 2250-Anionic chelant combinations are provided in FIG. 19 and results from the Uniquat QAC50-Anionic chelant combinations are provided in FIG. 20.

The data from this experiment shows synergistic surface activity boosting properties of the quat-anionic chelant solutions. For both Bardac 2250 and Uniquat QAC50, an increase in surface activity was observed when combined with Dequest 2000 or Trilon M. While, both of the anionic chelants are capable of decreasing the surface tension of all three Quaternary ammonium compounds tested (Bardac LF80, Bardac 2250, and Uniquat QAC50), Trilon M consistently produced lower surface tension over bubble lifetime when compared to the Quat-Dequest 2000 combinations.

Figure 21:
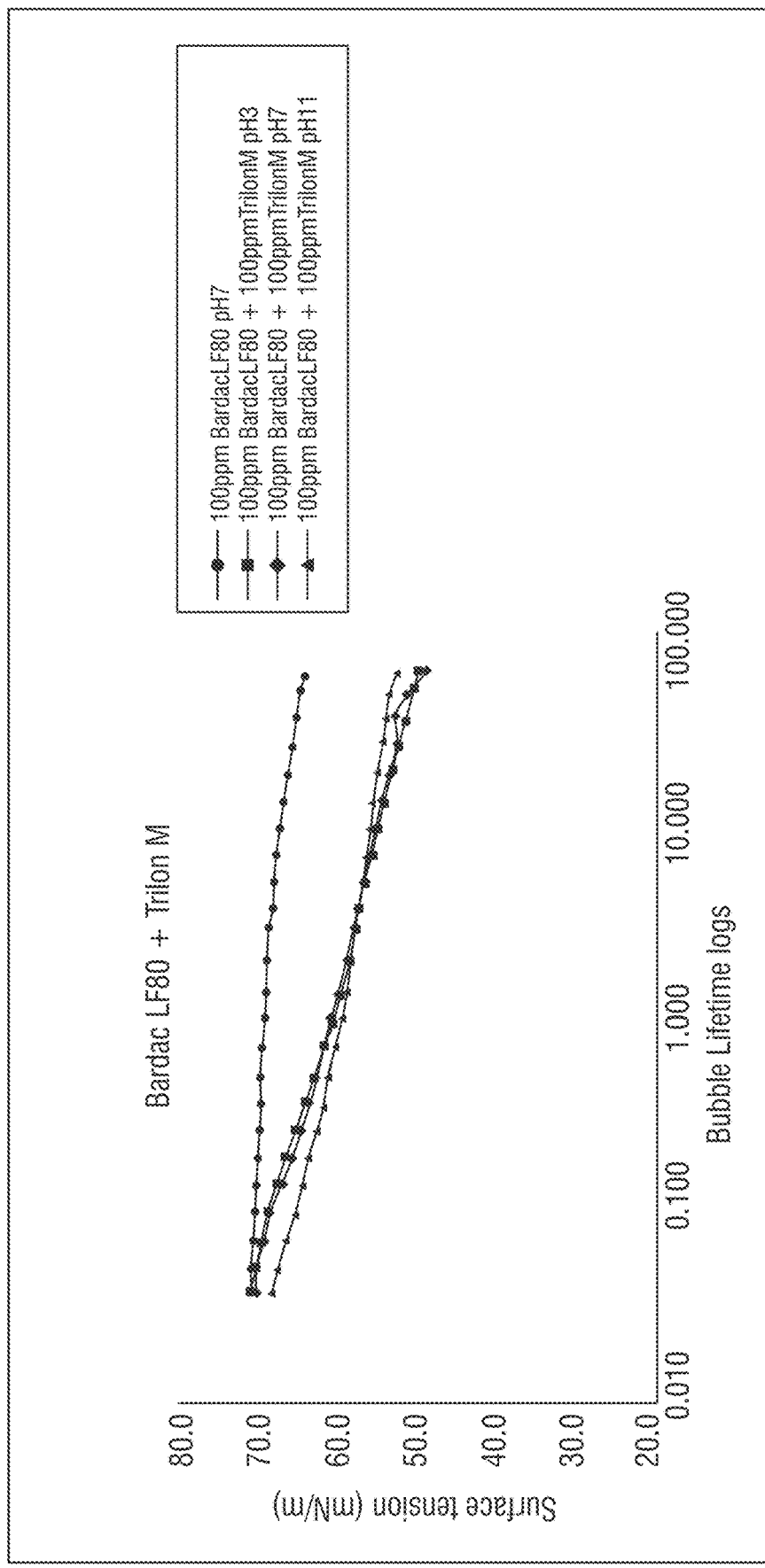
FIG. 21 shows a graphical representation of the average dynamic surface tension of Bardac LF80 and anionic chelant Trilon M as a function of pH as evaluated according to embodiments of the invention.

In order to determine the observed synergy of the quat-anionic chelant combinations is dependent on the pH of the solution, further testing according to the procedure outlined in Example 16 was used except at varying pH. The following solutions were analyzed; 100 ppm Bardac LF80 pH 7.0; 100 ppm Bardac LF80+100 ppm Trilon M pH 3.0; 100 ppm Bardac LF80+100 ppm Trilon M pH 9.0; and 100 ppm Bardac LF80+Trilon M pH 11.0. The data from this experiment is shown in FIG. 21. As can be seen for these results, the synergistic trends between Bardac LF80 and Trilon M appear to be independent of pH, as the pH of the solution had little to no influence on the dynamic surface activity of the solutions tested.

Figure 19:
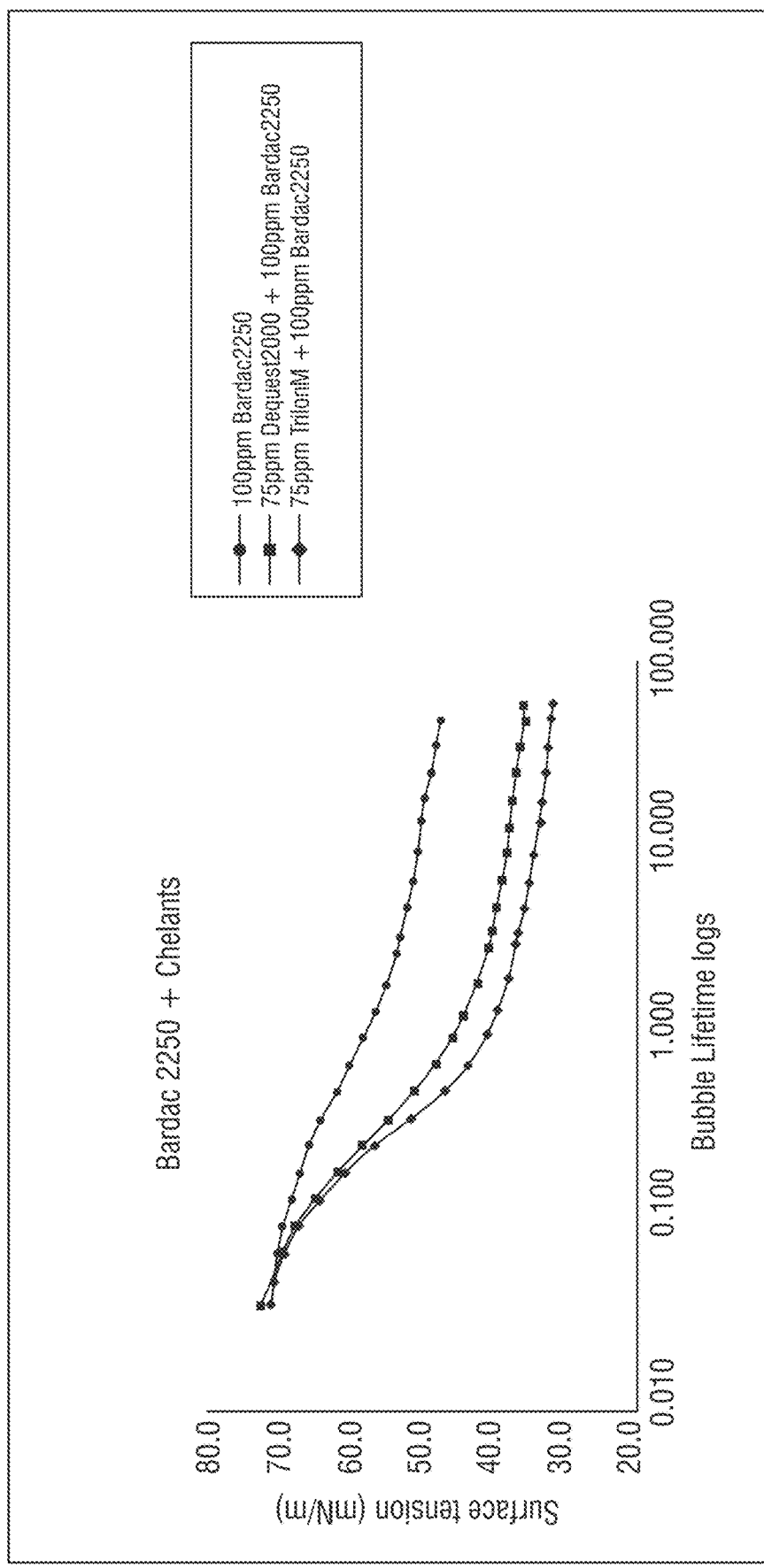
FIG. 19 is a graphical depiction of the average dynamic surface tension of Bardac 2250 and anionic chelant pairs as described in Example 18.
Figure 20:
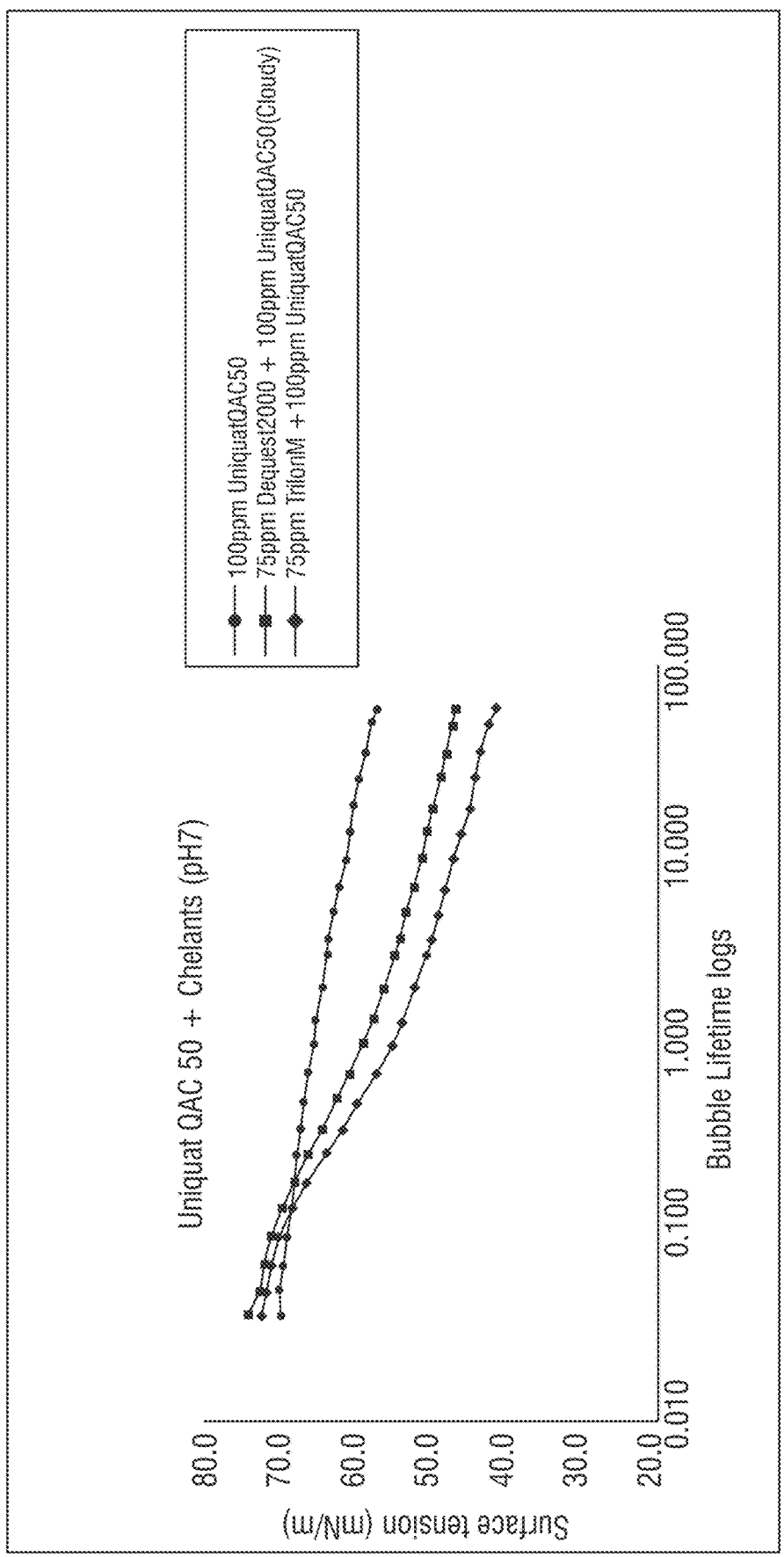
FIG. 20 is a graph showing the average dynamic surface tension of Uniquat QAC50 and anionic chelant pairs as described in Example 18.

When the results of the experiments of Example 18 are viewed in combination it can be seen that Quat (Bardac LF80, Bardac 2250, and Uniquat QAC50) and anionic chelant (Dequest 2000 and Trilon M) show synergistic surface activity boosting properties when combined, compared to Quat solutions alone, as seen in FIG. 18-20. In addition, the Quat and anionic chelant synergistic trends are as a function of chelant concentration and appear to be independent of pH, as shown in FIG. 18 and FIG. 21 respectively.

Example 19

Solubility of Quat-Anionic Polymer Solutions

A general solution behavior using 1% quat and 100 ppm polymer was analyzed. The results are provided in Table 20.

TABLE 20

Solution stability with Quaternary ammonium and Polymers

| | Quat | Acusol 445 | Results |
|---|---|---|---|
| Bardac 205M | 10,000 ppm | 100 ppm | Cloudy Soln. |
| Bardac 2250 | 10,000 ppm | 100 ppm | Cloudy Soln. |
| Bardac LF80 | 10,000 ppm | 100 ppm | Cloudy Soln. |

Further solution behavior using 500 ppm quat and the maximum addition of polymer before phase change (precipitation point) was analyzed. The polymer was added to a maximum concentration (insolubility point). The results are provided in Table 21.

TABLE 21

Solution stability with Quaternary ammonium and Polymers

| | Quat | Acusol 445 | Results |
|---|---|---|---|
| Bardac 205M | 500 ppm | 90 ppm | Hazy |
| Bardac 2250 | 500 ppm | 160 ppm | Hazy |
| Bardac LF80 | 500 ppm | 1500 + ppm | Transparent |

The results from these experiments show the shorter chain length on the quaternary ammonium, favored higher levels of polymer incorporation.

Example 20

Mineral Deposit Removal

Figure 22:
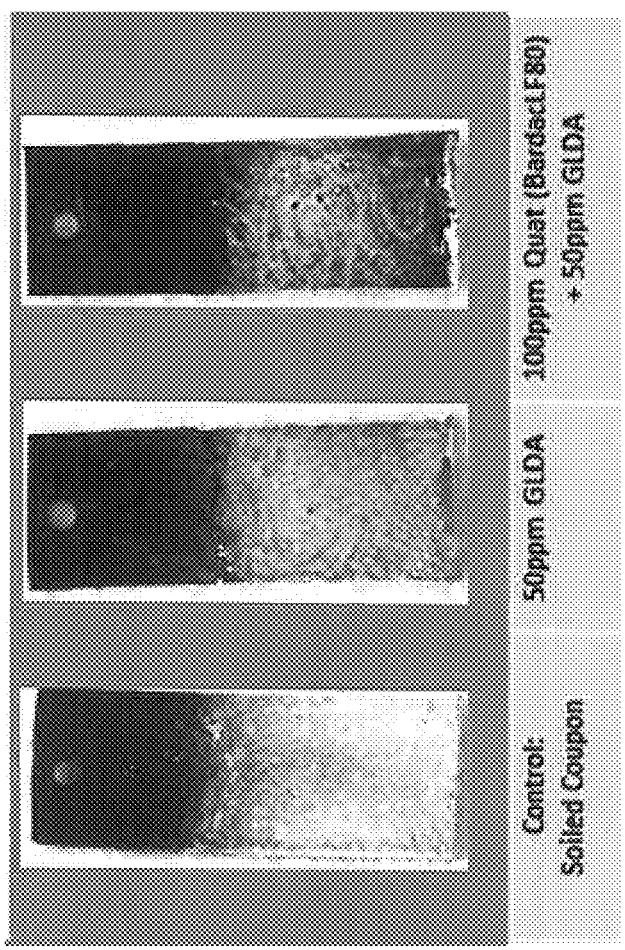
FIG. 22 shows representative images of the removal of mineral deposits from polypropylene surface and chelant activation as evaluated according to embodiments of the invention.

To determine the efficacy of Quat-anionic chelant and Quat-anionic polymer combinations to remove soil from the surface of an object the following procedure was used. Using an automated dip tester unit, pre-soiled polypropylene coupons (mineral deposit) were dipped into a solutions of water, 50 ppm Chelant (GLDA), and 100 ppm Bardac LF80+50 ppm Chelant (GLDA). The solutions were prepared and stirred in separate beakers. The soiled tiles were submerged into beakers of the various cleaning compositions for a period of time 10 minutes. Thereafter the tile was visually analyzed to assess the cleanliness of the tile, namely the mineral deposit removal. Visual observation of this scale removal for the Quat-anionic chelant solutions and the Quat-anionic polymer solutions are shown in FIG. 22.

Figure 23:
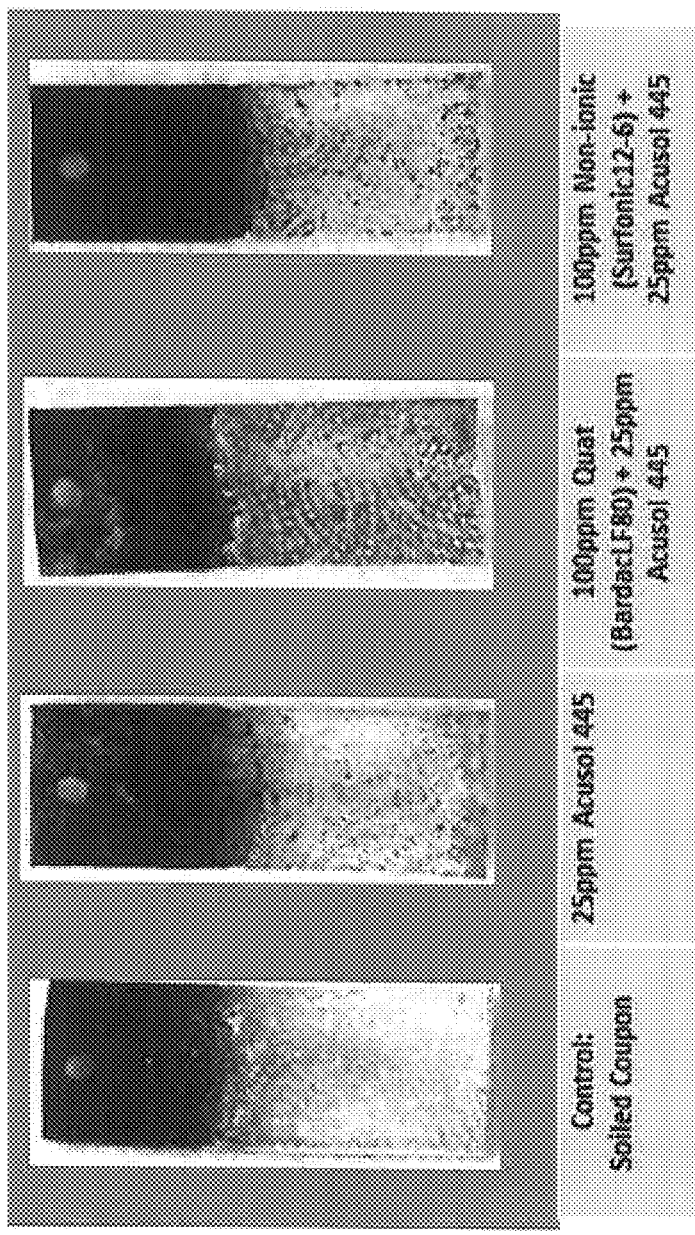
FIG. 23 shows representative images of the removal of mineral deposits from polypropylene surface and polymer activation as evaluated according to embodiments of the invention.

Using the same automated dip tester unit, pre-soiled polypropylene coupons (mineral deposit) were dipped into a solutions of water, 25 ppm Acusol 445, 100 ppm Bardac LF80+25 ppm Acusol 445, and 100 ppm nonionic surfactant (Surfonic 12-6)+25 ppm Acusol 445. Visual observation of scale removal for the Quat-anionic chelant solutions and the Quat-anionic polymer solutions are shown in FIG. 23.

The results show a benefit of using a synergistic combination of the quat and anionic polymer/chelant according to embodiments of the invention. The combination enhances the soil removal power of the chelants and polymers, more than a non-synergistic nonionic surfactant in combination with the anionic polymer (as shown by 100 ppm nonionic surfactant (Surfonic 12-6)+25 ppm Acusol 445). Without being bound by a particular mechanism of action or theory of the invention, the quat and anionic polymer/chelant forms a more surface active complex with the chelating agent or polymer, which effectively seeks out the scales on a surface through surface excess and/or less charge repulsion mechanism. Although the non-synergistic surfactants (i.e. nonionic surfactant) can improve wetting, no surface excess and/or less charge repulsion of the chelating agent and/or polymer exists.

The inventions being thus described, it will be obvious that the same may be varied in many ways. Such variations are not to be regarded as a departure from the spirit and scope of the inventions and all such modifications are intended to be included within the scope of the following claims. The above specification provides a description of the manufacture and use of the disclosed compositions and methods. Since many embodiments can be made without departing from the spirit and scope of the invention, the invention resides in the claims.

What is claimed is:

1. An antimicrobial composition, comprising:
a quaternary ammonium compound having the formula:

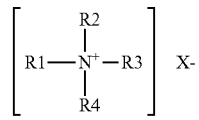

wherein groups R1, R2, R3, and R4 are alkyl groups that are substituted, unsubstituted, saturated, unsaturated, branched, unbranched, cyclic, acyclic, and/or aromatic, each having less than a C20 chain length, and wherein X— is an anionic counterion; and
an anionic sulfate or sulfonate-based surfactant having C6-C18 chain length;
wherein the molar ratio of anionic surfactant to quaternary ammonium is from about 2 moles anionic surfactant to about 1 mole of quaternary ammonium to about 1 mole anionic surfactant to about 2 moles of quaternary ammonium; and
wherein the composition is a ready to use solution, or a solid or liquid concentrate that is soluble in water, has a pH of about 4.5 to about 10 and is substantially free of silanes, and oxidants.

2. The antimicrobial composition of claim 1, wherein the anionic surfactant is a sulfonated fatty acid, and wherein the quaternary ammonium compound is selected from the group consisting of monoalkyltrimethyl ammonium salts, monoalkyldimethylbenzyl ammonium salts, dialkyldimethyl ammonium salts, heteroaromatic ammonium salts, polysubstituted quaternary ammonium salts, bis-quaternary ammonium salts, polymeric quaternary ammonium salts, and combinations thereof.

3. The antimicrobial composition of claim 1, wherein the pH is between about 7 and about 8, and wherein the composition further comprises an acidulant, anionic polymer and/or an anionic chelant.

4. The antimicrobial composition of claim 3, wherein the anionic polymer or anionic chelant is polyacrylic acid polymer having a molecular weight greater than about 4000.

5. The antimicrobial composition of claim 3, wherein the anionic chelant or polymer is an aminocarboxylate or derivative thereof, a phosphonic acid or phosphonate salt.

6. The antimicrobial composition of claim 1, wherein the molar ratio of anionic surfactant to quaternary ammonium is from about 1 mole anionic surfactant to about 1 mole of quaternary ammonium.

7. The antimicrobial composition of claim 1, wherein the quaternary ammonium compound is comprised of one or more of dialkyl quaternary ammonium and alkyl benzyl quaternary ammonium and wherein the anionic surfactant is sulfonated oleic acid.

8. The antimicrobial composition of claim 1, wherein the quaternary ammonium has a carbon chain length of 8 to 20 carbon atoms, and wherein the quaternary ammonium compound groups R1, R2, R3, and R4 each have less than a C10 chain length.

9. The antimicrobial composition of claim 8, wherein the quaternary ammonium compound is a dioctyl (C8) dimethyl ammonium chloride, didecyl (C10) dimethyl ammonium chloride, dialkyl benzyl ammonium chloride and/or alkyl benzyl ammonium chloride.

10. The antimicrobial composition of claim 1, wherein the composition provides in a use solution from about 50 ppm to about 400 ppm quaternary ammonium compound and at least about 10 ppm anionic surfactant.

11. The antimicrobial composition of claim 1, further comprising an additional functional ingredient selected from the group consisting of additional surfactants, thickeners and/or viscosity modifiers, solvents, solubility modifiers, humectants, metal protecting agents, stabilizing agents, corrosion inhibitors, sequestrants and/or chelating agents, solidifying agent, sheeting agents, pH modifying components (acidulant), fragrances and/or dyes, hydrotropes or couplers, buffers, and combinations thereof.

12. A method of killing microbes comprising:
applying to a substrate the antimicrobial composition of claim 1;
wherein the composition provides at least 5 log kill and/or decreases scale deposits on treated surfaces; and
wherein the microbes comprise *Escherichia coli, Salmonella typhimurium, Staphylococcus aureus, Salmonella choleraesurus, Pseudomonas aeruginosa, Listeria monocytogenes*, or a combination thereof.

13. The method of claim 12, wherein the pH of the composition is between about 7 and about 8, and wherein the use solution conditions have a water hardness of greater than 5 grains per gallon (gpg).

* * * * *